(12) United States Patent
Suzuki et al.

(10) Patent No.: US 10,590,395 B2
(45) Date of Patent: Mar. 17, 2020

(54) MUTEIN, METHOD FOR PRODUCING SAID MUTEIN, GENE ENCODING SAID MUTEIN, RECOMBINANT VECTOR AND PLANT BEARING SAID GENE, METHOD FOR CONTROLLING AMOUNT OF MEVALONIC ACID PRODUCED AND AMOUNT OF ISOPRENOID PRODUCED, METHOD FOR CONTROLLING 3-HYDROXY-3-METHYLGLUTARYL-COA REDUCTASE ACTIVITY

(71) Applicants: OSAKA UNIVERSITY, Suita-shi, Osaka (JP); SUMITOMO RUBBER INDUSTRIES, LTD., Kobe-shi, Hyogo (JP)

(72) Inventors: Keiko Suzuki, Suita (JP); Jekson Robertlee, Suita (JP); Toshiya Muranaka, Suita (JP); Keiji Takagi, Kobe (JP); Yukino Inoue, Kobe (JP); Kazuhisa Fushihara, Kobe (JP)

(73) Assignees: OSAKA UNIVERSITY, Osaka (JP); SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 24 days.

(21) Appl. No.: 15/313,050

(22) PCT Filed: May 22, 2015

(86) PCT No.: PCT/JP2015/064821
§ 371 (c)(1),
(2) Date: Nov. 21, 2016

(87) PCT Pub. No.: WO2015/178493
PCT Pub. Date: Nov. 26, 2015

(65) Prior Publication Data
US 2017/0204377 A1 Jul. 20, 2017

(30) Foreign Application Priority Data
May 23, 2014 (JP) ................................ 2014-107508

(51) Int. Cl.
| | | |
|---|---|---|
| C12N 15/82 | (2006.01) | |
| C12N 15/00 | (2006.01) | |
| C12N 15/09 | (2006.01) | |
| C12N 9/04 | (2006.01) | |
| A01H 5/00 | (2018.01) | |
| A01N 37/18 | (2006.01) | |
| C12P 5/02 | (2006.01) | |
| C12P 7/40 | (2006.01) | |

(52) U.S. Cl.
CPC ............. *C12N 9/0006* (2013.01); *A01H 5/00* (2013.01); *A01N 37/18* (2013.01); *C12N 15/00* (2013.01); *C12N 15/09* (2013.01); *C12N 15/8243* (2013.01); *C12Y 101/01034* (2013.01); *C12P 5/02* (2013.01); *C12P 7/40* (2013.01)

(58) Field of Classification Search
CPC ................... C12N 15/8243; C12Y 101/01034
See application file for complete search history.

(56) References Cited

U.S. PATENT DOCUMENTS

| | | | |
|---|---|---|---|
| 6,998,471 B2 * | 2/2006 | Hallahan ................ | C12N 15/52 435/252.3 |
| 7,238,514 B2 * | 7/2007 | Matsuda .............. | C12N 9/1085 435/193 |
| 2004/0072323 A1 | 4/2004 | Matsuda et al. | |

FOREIGN PATENT DOCUMENTS

| | | |
|---|---|---|
| WO | WO 01/31043 A1 | 5/2001 |
| WO | WO 2013/039378 A1 | 3/2013 |
| WO | WO 2013/106868 A1 | 7/2013 |

OTHER PUBLICATIONS

Skinner, Mathew M., and Thomas C. Terwilliger. "Potential use of additivity of mutational effects in simplifying protein engineering." Proceedings of the National Academy of Sciences 93.20 (1996): 10753-10757. (Year: 1996).*
Supplementary Partial European Search Report issued in European Patent Application No. 15795799.4 dated Oct. 5, 2017.
Ching et al., "Analysis of the Specificity of the AMP-activated Protein Kinase by Site-directed Mutagenesis of Bacterially Expressed 3-hydroxy 3-methylglutaryl-CoA Reductase, Using a Single Primer Variant of the Unique-site-elimination . . . ," Eur. J. Biochem., vol. 237, No. 3, 1996, pp. 800-808.
Chye et al., "3-hydroxy-3-methylglutaryl-coenzyme A reductase [*Hevea brasiliensis*]," GenBank Accession No. AAA33360.1, https://www.ncbi.nlm.nih.gov/protein/AAA33360.1, Apr. 27, 1993, pp. 1-2 (Total 3 pages).

(Continued)

*Primary Examiner* — Weihua Fan
(74) *Attorney, Agent, or Firm* — Birch, Stewart, Kolasch & Birch, LLP

(57) ABSTRACT

Provided is a mutant protein obtained by mutating a specific amino acid residue of HMGR, a rate-limiting enzyme of isoprene monomer biosynthesis in the polyisoprenoid biosynthesis pathway. The present invention relates to a mutant protein, wherein at least one amino acid residue selected from the group consisting of amino acid residues at positions 91, 225, 257, 287, 339, 411, 470, 509 and 574 of the *Arabidopsis thaliana* 3-hydroxy-3-methylglutaryl CoA reductase shown by SEQ ID NO:1 and amino acid residues at positions corresponding to the foregoing in 3-hydroxy-3-methylglutaryl CoA reductase is deleted or replaced with another amino acid residue.

14 Claims, 1 Drawing Sheet
Specification includes a Sequence Listing.

(56) References Cited

OTHER PUBLICATIONS

Chye et al., "hydroxymethylglutaryl-CoA reductase [*Hevea brasiliensis*]," GenBank Accession No. CAA38469.1, https://www.ncbi.nlm.nih.gov/protein/CAA38469.1, Apr. 18, 2005, pp. 1-2 (Total 4 pages).

Dale et al., "Bacterial Expression of the Catalytic Domain of 3-hydroxy-3-methylglutaryl-CoA Reductase (isoform HMGR1) from *Arabidopsis thaliana*, and its Inactivation by Phosphorylation at Ser577 by Brassica oleracea . . . ," Eur. J. Biochem., vol. 233, 1995, pp. 506-513.

International Search Report (form PCT/ISA/210), dated Aug. 25, 2015, for International Application No. PCT/JP2015/064821, with an English translation.

Omkumar et al., "Modulation of Syrian Hamster 3-Hydroxy-3-methylglutaryl-CoA Reductase Activity by Phosphorylation," J. Biol. Chem., vol. 269, No. 9, Mar. 4, 1994, pp. 6810-6814.

Sando et al., "hydroxymethylglutaryl-CoA reductase [*Hevea brasiliensis*]," GenBank Accession No. BAF98280.1, https://www.ncbi.nlm.nih.gov/protein/BAF98280, Sep. 13, 2008, pp. 1-2 (Total 4 pages).

Sando et al., "hydroxymethylglutaryl-CoA reductase [*Hevea brasiliensis*]," GenBank Accession No. BAF98281.1, https://www.ncbi.nlm.nih.gov/protein/BAF98281.1, Sep. 13, 2008, pp. 1-2 (Total 4 pages).

Cao et al., "Euphorbia pekinensis HMGR protein sequence, SEQ ID 4, Medicinal plant radix euphorbiae pekinensis 3-hydroxy-3-methyl glutaryl coenzyme A reductase protein coding sequence", Database Geneseq [Online], ARL00254, May 15, 2008, 1 page, XP002776668.

Database Geneseq [Online], "HMG-CoA reductase polypeptide #17," EBI accession No. ADM98764, Jul. 1, 2004, 1 page.

Database Geneseq [Online], "HMG-CoA reductase polypeptide #61," EBI accession No. ADM98808, Jul. 1, 2004, 1 page.

Database Geneseq [Online], "HMG-CoA reductase polypeptide #74," EBI accession No. ADM98821, Jul. 1, 2004, 1 page.

Database Geneseq [Online], "Oryza sativa HMG CoA reductase Seq ID No. 2," EBI accession No. BAQ55714, Sep. 12, 2013, 1 page.

\* cited by examiner

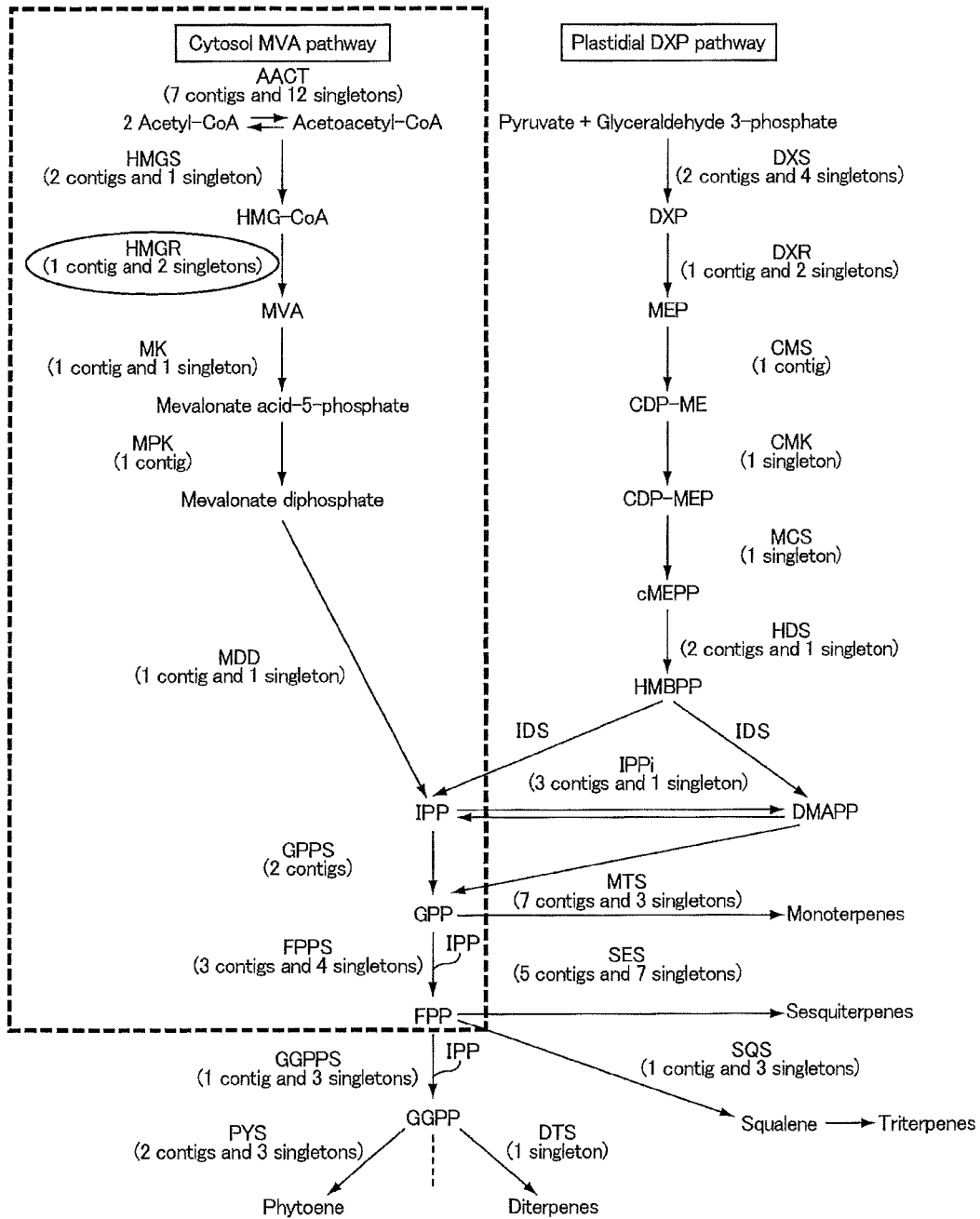

MUTEIN, METHOD FOR PRODUCING SAID MUTEIN, GENE ENCODING SAID MUTEIN, RECOMBINANT VECTOR AND PLANT BEARING SAID GENE, METHOD FOR CONTROLLING AMOUNT OF MEVALONIC ACID PRODUCED AND AMOUNT OF ISOPRENOID PRODUCED, METHOD FOR CONTROLLING 3-HYDROXY-3-METHYLGLUTARYL-COA REDUCTASE ACTIVITY

TECHNICAL FIELD

The present invention relates to a mutant protein, to a method for producing the mutant protein, to a gene coding for the mutant protein, to a recombinant vector and plant carrying the gene, to methods for controlling mevalonic acid yield and isoprenoid yield, and to a method for controlling 3-hydroxy-3-methylglutaryl CoA reductase activity.

BACKGROUND ART

In the polyisoprenoid biosynthesis pathway, 3-hydroxy-3-methylglutaryl CoA reductase (hereunder also referred to as HMGR or HMG-CoA reductase) is a rate-limiting enzyme in isoprene monomer (isopentenyl diphosphate) biosynthesis. It is known that the enzyme activity of HMGR is controlled by reversible post-translational phosphorylation, and specifically, inactivation of enzyme activity by C-terminal serine phosphorylation is well known as a post-translational regulatory mechanism of HMGR in animals. This has also been confirmed in plants, and in Non Patent Literature 1 in particular, reduced enzyme activity due to phosphorylation of the residue serine 577 corresponding to the C-terminal serine is confirmed in Arabidopsis thaliana.

Methods also exist for increasing polyisoprenoid yield without genetic recombination, such as methods of increasing polyisoprenoid yield using cholesterol biosynthesis inhibitors, but there is still room for improvement in methods for increasing polyisoprenoid yield and the like and there is a need for the development of further technologies.

CITATION LIST

Non Patent Literature

Non Patent Literature 1: Dale S., et al., Eur. J. Biochem. 233(2), 506-513 (1995)

SUMMARY OF INVENTION

Technical Problem

It is an object of the present invention to resolve these problems and provide a mutant protein obtained by mutating a specific amino acid residue of HMGR, a rate-limiting enzyme of isoprene monomer biosynthesis in the polyisoprenoid biosynthesis pathway. Other objects are to provide a method for producing the mutant protein, a gene coding for the mutant protein, and a recombinant vector and plant carrying the gene, and to provide a method for controlling 3-hydroxy-3-methylglutaryl CoA reductase activity. Even another object is to provide a method for controlling mevalonic acid yield and isoprenoid yield.

Solution to Problem

The present invention relates to a mutant protein, wherein at least one amino acid residue selected from the group consisting of amino acid residues at positions 91, 225, 257, 287, 339, 411, 470, 509 and 574 of the Arabidopsis thaliana 3-hydroxy-3-methylglutaryl CoA reductase shown by SEQ ID NO:1 and amino acid residues at positions corresponding to the foregoing in 3-hydroxy-3-methylglutaryl CoA reductase is deleted or replaced with another amino acid residue.

The amino acid residues at positions corresponding to the amino acid residues at positions 91, 225, 257, 287, 411, 470, 509 and 574 of the Arabidopsis thaliana 3-hydroxy-3-methylglutaryl CoA reductase are preferably amino acid residues at positions 70, 214, 246, 276, 400, 459, 498 and 563, respectively, of the Hevea brasiliensis 3-hydroxy-3-methylglutaryl CoA reductase shown by SEQ ID NO:10.

The amino acid residues at positions corresponding to the amino acid residues at positions 411, 470, 509 and 574 of the Arabidopsis thaliana 3-hydroxy-3-methylglutaryl CoA reductase are preferably amino acid residues at positions 35, 94, 133 and 198, respectively, of the Hevea brasiliensis 3-hydroxy-3-methylglutaryl CoA reductase shown by SEQ ID NO:70.

The amino acid residues at positions corresponding to the amino acid residues at positions 91, 225, 257, 287, 339, 411, 470, 509 and 574 of the Arabidopsis thaliana 3-hydroxy-3-methylglutaryl CoA reductase are preferably amino acid residues at positions 81, 225, 257, 287, 339, 411, 470, 509 and 574, respectively, of the Hevea brasiliensis 3-hydroxy-3-methylglutaryl CoA reductase shown by SEQ ID NO:71.

The amino acid residues at positions corresponding to the amino acid residues at positions 225, 257, 287, 339, 411, 470, 509 and 574 of the Arabidopsis thaliana 3-hydroxy-3-methylglutaryl CoA reductase are preferably amino acid residues at positions 243, 275, 305, 357, 429, 488, 527 and 592, respectively, of the Hevea brasiliensis 3-hydroxy-3-methylglutaryl CoA reductase shown by SEQ ID NO:72.

The amino acid residues at positions corresponding to the amino acid residues at positions 91, 225, 287, 339, 411, and 470 of the Arabidopsis thaliana 3-hydroxy-3-methylglutaryl CoA reductase are preferably amino acid residues at positions 73, 243, 305, 357, 429 and 488, respectively, of the Hevea brasiliensis 3-hydroxy-3-methylglutaryl CoA reductase shown by SEQ ID NO:73.

At least one amino acid residue selected from the group consisting of the amino acid residues at positions 91 and 339 of SEQ ID NO:1 and the amino acid residues at positions corresponding to the foregoing is preferably replaced with aspartic acid or glutamic acid.

At least one amino acid residue selected from the group consisting of the amino acid residues at positions 225, 257, 287, 411, 470, 509 and 574 of SEQ ID NO:1 and the amino acid residues at positions corresponding to the foregoing is preferably deleted or replaced with alanine, phenylalanine or cysteine.

At least one amino acid residue selected from the group consisting of the amino acid residues at positions 91 and 339 of SEQ ID NO:1 and the amino acid residues at positions corresponding to the foregoing is preferably deleted or replaced with alanine or phenylalanine.

At least one amino acid residue selected from the group consisting of the amino acid residues at positions 225, 257, 287, 411, 470, 509 and 574 of SEQ ID NO:1 and the amino acid residues at positions corresponding to the foregoing is preferably replaced with aspartic acid or glutamic acid.

The present invention also relates to a method for controlling isoprenoid yield using the mutant protein.

It also relates to a method for controlling mevalonic acid yield using the mutant protein.

The present invention relates to a gene, coding for the mutant protein.

It also relates to a method for controlling isoprenoid yield using the gene.

It also relates to a method for controlling mevalonic acid yield using the gene.

It also relates to a recombinant vector, carrying the gene.

The present invention relates to a plant, carrying the gene.

It also relates to a method for controlling isoprenoid yield using the plant.

It also relates to a method for controlling mevalonic acid yield using the plant.

The present invention also relates to an isoprenoid-producing plant, carrying the gene.

It also relates to a method for controlling isoprenoid yield using the isoprenoid-producing plant.

It also relates to a method for controlling mevalonic acid yield using the isoprenoid-producing plant.

The present invention relates to a method for controlling 3-hydroxy-3-methylglutaryl CoA reductase activity, wherein at least one amino acid residue selected from the group consisting of amino acid residues at positions 91, 225, 257, 287, 339, 411, 470, 509 and 574 of the *Arabidopsis thaliana* 3-hydroxy-3-methylglutaryl CoA reductase shown by SEQ ID NO:1 and amino acid residues at positions corresponding to the foregoing in 3-hydroxy-3-methylglutaryl CoA reductase is deleted or replaced with another amino acid residue.

At least one amino acid residue selected from the group consisting of the amino acid residues at positions 91 and 339 of SEQ ID NO:1 and the amino acid residues at positions corresponding to the foregoing is preferably replaced with aspartic acid or glutamic acid.

At least one amino acid residue selected from the group consisting of the amino acid residues at positions 225, 257, 287, 411, 470, 509 and 574 of SEQ ID NO:1 and the amino acid residues at positions corresponding to the foregoing is preferably deleted or replaced with alanine, phenylalanine or cysteine.

At least one amino acid residue selected from the group consisting of the amino acid residues at positions 91 and 339 of SEQ ID NO:1 and the amino acid residues at positions corresponding to the foregoing is preferably deleted or replaced with alanine or phenylalanine.

At least one amino acid residue selected from the group consisting of the amino acid residues at positions 225, 257, 287, 411, 470, 509 and 574 of SEQ ID NO:1 and the amino acid residues at positions corresponding to the foregoing is preferably replaced with aspartic acid or glutamic acid.

The present invention relates to a method for producing a mutant protein, the method including a step of deleting, or replacing with another amino acid residue, at least one amino acid residue selected from the group consisting of amino acid residues at positions 91, 225, 257, 287, 339, 411, 470, 509 and 574 of the *Arabidopsis thaliana* 3-hydroxy-3-methylglutaryl CoA reductase shown by SEQ ID NO:1 and amino acid residues at positions corresponding to the foregoing in 3-hydroxy-3-methylglutaryl CoA reductase.

At least one amino acid residue selected from the group consisting of the amino acid residues at positions 91 and 339 of SEQ ID NO:1 and the amino acid residues at positions corresponding to the foregoing is preferably replaced with aspartic acid or glutamic acid.

At least one amino acid residue selected from the group consisting of the amino acid residues at positions 225, 257, 287, 411, 470, 509 and 574 of SEQ ID NO:1 and the amino acid residues at positions corresponding to the foregoing is preferably deleted or replaced with alanine, phenylalanine or cysteine.

At least one amino acid residue selected from the group consisting of the amino acid residues at positions 91 and 339 of SEQ ID NO:1 and the amino acid residues at positions corresponding to the foregoing is preferably deleted or replaced with alanine or phenylalanine.

At least one amino acid residue selected from the group consisting of the amino acid residues at positions 225, 257, 287, 411, 470, 509 and 574 of SEQ ID NO:1 and the amino acid residues at positions corresponding to the foregoing is preferably replaced with aspartic acid or glutamic acid.

Advantageous Effects of Invention

The mutant protein of the present invention is a mutant protein obtained by deleting, or replacing with another amino acid residue, a specific amino acid residue of HMGR, a rate-limiting enzyme of isoprene monomer biosynthesis in the polyisoprenoid biosynthesis pathway. Consequently, HMGR enzyme activity and therefore mevalonic acid and isoprenoid yields can be controlled by preparing this mutant protein or a transformant having introduced therein a gene coding for this mutant protein.

BRIEF DESCRIPTION OF DRAWINGS

FIG. 1 shows a part of the polyisoprenoid biosynthesis pathway.

DESCRIPTION OF EMBODIMENTS

The inventors conducted various researches aimed at increasing the amount of polyisoprenoids biosynthesized in the polyisoprenoid biosynthesis pathway. A part of the polyisoprenoid biosynthesis pathway is shown in FIG. 1. As shown in FIG. 1, various enzymes are involved in the polyisoprenoid biosynthesis pathway, but of these the inventors focused on 3-hydroxy-3-methylglutaryl CoA reductase (HMGR), a rate-limiting enzyme in the biosynthesis of isoprene monomer, which forms the basic skeleton of polyisoprenoids.

It is well known that a serine at the C-terminal of HMGR, e.g. serine 577 of HMGR from *Arabidopsis thaliana*, is involved in controlling its activity. Specifically, the activity of HMGR is lost when the serine at the C-terminal is phosphorylated. For this reason, a mutant (see for example Non Patent Literature 1) having this serine replaced with alanine in order to prevent serine phosphorylation is well known. It has also been widely believed that the activity of this mutant cannot then be controlled by phosphorylation. Thus, at the time of filing the present application it has been generally thought that the activity of HMGR is no longer controllable by phosphorylation when the C-terminal serine has been replaced by alanine.

Despite such technical common knowledge, the inventors discovered as a result of further research into phosphorylation of HMGR amino acid residues that new amino acid residues other than the known serine residue are involved in controlling enzyme activity.

Specifically, it was discovered that in an *Arabidopsis thaliana* plant transformant expressing a mutant HMGR known from Non Patent Literature 1, in which the HMGR C-terminal serine has been replaced with alanine so that the enzyme activity of the HMGR is not inactivated by phosphorylation of the serine, the enzyme activity of the mutant HMGR is increased by further phosphatase treatment. This suggests that there is an amino acid residue other than the known serine residue that is involved as a phosphorylation site in controlling HMGR enzyme activity. This is an extremely significant discovery contradicting the technical common knowledge described above, and could not have been predicted by a person skilled in the art. In living *Arabidopsis thaliana*, phosphorylation is performed as necessary by a phosphorylation enzyme (kinase).

Based on this suggestion, the inventors next searched for new phosphorylation sites for controlling HMGR enzyme activity. Specifically, we screened amino acid residues other than the known serine residue (corresponding to serine 577 described above) involved in controlling HMGR enzyme activity, and out of the amino acid residues contained in highly conserved sequences or in other words conserved regions of various types of HMGR, we identified 9 amino acid residues capable of controlling HMGR activity. We then demonstrated that by preparing mutant proteins in which each of the 9 identified specific amino acid residues is deleted or substituted, it is possible to raise, lower or maintain HMGR enzyme activity, or in other words to control HMGR enzyme activity.

Examples of amino acid residues capable of serving as phosphorylation sites include serine, threonine, tyrosine, histidine, arginine and lysine.

Thus, by preparing a transformant having an introduced gene coding for the mutant protein prepared in the present invention as described above, it is possible to control the HMGR enzyme activity of the transformant, and therefore to control mevalonic acid yield and isoprenoid yield.

Specifically, mutant HMGRs produced by replacing a threonine residue corresponding to position 91 and a serine residue corresponding to position 339 in the *Arabidopsis thaliana* HMGR shown by SEQ ID NO:1 by other amino acid residues and preferably by aspartic acid or glutamic acid have enhanced enzyme activity.

Moreover, mutant HMGRs produced by replacing a tyrosine residue corresponding to position 225, a tyrosine residue corresponding to position 257, a serine residue corresponding to position 287, a serine residue corresponding to position 411, a threonine residue corresponding to position 470, a threonine residue corresponding to position 509 and a tyrosine residue corresponding to position 574 in the *Arabidopsis thaliana* HMGR shown by SEQ ID NO:1 by other amino acid residues and preferably by alanine, phenylalanine or cysteine also have enhanced enzyme activity.

Thus, enzyme activity is enhanced and the amount of downstream metabolites can be increased in plants having introduced genes coding for these mutant HMGRs. Consequently, by introducing a gene coding for such a mutant HMGR into *Hevea brasiliensis*, for example, it is possible to enhance enzyme activity in the *Hevea brasiliensis* and increase the amount of natural rubber biosynthesized as a downstream metabolite.

On the other hand, mutant HMGRs produced by replacing a threonine residue corresponding to position 91 and a serine residue corresponding to position 339 in the *Arabidopsis thaliana* HMGR shown by SEQ ID NO:1 by other amino acid residues and preferably by alanine or phenylalanine have reduced enzyme activity.

Moreover, mutant HMGRs produced by replacing a tyrosine residue corresponding to position 225, a tyrosine residue corresponding to position 257, a serine residue corresponding to position 287, a serine residue corresponding to position 411, a threonine residue corresponding to position 470, a threonine residue corresponding to position 509 and a tyrosine residue corresponding to position 574 in the *Arabidopsis thaliana* HMGR shown by SEQ ID NO:1 by other amino acid residues and preferably by aspartic acid or glutamic acid have reduced enzyme activity.

Thus, enzyme activity is reduced and the amount of downstream metabolites can be reduced in plants having introduced genes coding for these mutant HMGRs. Consequently, by introducing a gene coding for such mutant HMGR into a plant that accumulates a harmful substance or bitter substance in the edible part of the plant, such as a potato (solanine), tomato (tomatine), lettuce (lactucin) or soy bean (group A soya saponin), it is possible to reduce HMGR enzyme activity in the edible part of the plant and reduce the amount of harmful steroid alkaloid or sesquiterpenoid as a downstream metabolite.

The conventional methods for enhancing HMGR function in plants have been mostly by gene overexpression, and no one imagined that multiple amino acids of the enzyme were involved in its activity. Gene overexpression is predicated on gene recombination, but in the present invention the activity can be controlled by amino acid substitution. This means that modification is possible without recombination, allowing for much easier handling than with a recombinant, and greater industrial applicability.

In the Description, HMGR refers to an enzyme that catalyzes the reduction of hydroxymethylglutaryl-CoA (HMG-CoA) to mevalonic acid (MVA), the enzyme activity of HMGR denotes the activity of this reduction reaction, and the enzyme is possessed by various biological species. Moreover, multiple types of HMGR may be present in one biological species.

Phosphorylation is a reaction performed as necessary in vivo by kinases possessed by living organisms; in proteins that function as enzymes and the like in vivo, the presence or absence, the strength and the like of these functions are controlled by phosphorylation and dephosphorylation.

(Mutant Protein)

The mutant protein of the present invention is obtained by deleting, or replacing with another amino acid residue, at least one amino acid residue selected from the group consisting of the amino acid residues at positions 91, 225, 257, 287, 339, 411, 470, 509 and 574 of the *Arabidopsis thaliana* HMGR shown by SEQ ID NO:1 and amino acid residues at positions corresponding to the foregoing in HMGR.

The amino acid residues at positions 91, 225, 257, 287, 339, 411, 470, 509 and 574 of the *Arabidopsis thaliana* HMGR shown by SEQ ID NO:1 and the amino acid residues at positions corresponding to the foregoing refer to amino acid residues in sequences that are highly conserved in HMGR irrespective of the type of HMGR, or in other words amino acid residues contained in conserved regions of HMGR. A conserved region denotes a site having a similar sequence (structure), and in the case of proteins, it is presumed to be a site having a similar function. When the *Arabidopsis thaliana*-derived HMGR shown by SEQ ID NO:1 and another type of HMGR have a common conserved region, it can be presumed that the latter simultaneously possesses an amino acid residue corresponding to the amino acid residue at position 91, 225, 257, 287, 339, 411, 470, 509 or 574 of the *Arabidopsis thaliana* HMGR shown by SEQ ID NO:1, and also that the amino acid residue in the conserved region plays a similar role as the corresponding amino acid residue in the *Arabidopsis thaliana* HMGR shown by SEQ ID NO:1. In the present invention, conserved regions of HMGR were selected in advance by multiple sequence alignment, and the positions of the amino acid residues were selected from those that were determined to be highly conserved.

In the Description, multiple sequence alignment can be performed as described later in the Examples.

The conserved regions containing amino acid residues at positions corresponding to the amino acid residues at positions 91, 225, 257, 287, 339, 411, 470, 509 and 574 of the *Arabidopsis thaliana* HMGR shown by SEQ ID NO:1 are not particularly limited as long as they are conserved regions containing amino acid residues corresponding to the amino acid residues at positions 91, 225, 257, 287, 339, 411, 470, 509 and 574, respectively, of the *Arabidopsis thaliana* HMGR shown by SEQ ID NO:1, but the degree of sequence identity to the sequence of each conserved region of the *Arabidopsis thaliana* HMGR shown by SEQ ID NO:1 is preferably at least 60%, more preferably at least 70%, still more preferably at least 75%, yet more preferably at least 80%, particularly preferably at least 85%, further particularly at least 88%, most preferably at least 90%, even most preferably at least 92%, still most preferably at least 95%, particularly most preferably at least 98%, with no upper limit.

The conserved regions containing the specific amino acid residues of the *Arabidopsis thaliana* HMGR shown by SEQ ID NO:1 denote as follows: the conserved region containing the position 48 amino acid residue is the sequence of amino acid residues 48 to 58 of SEQ ID NO:2; the conserved region containing the position 91 amino acid residue is the sequence of amino acid residues 85 to 91 of SEQ ID NO:3; the conserved region containing the position 225 amino acid residue is the sequence of amino acid residues 222 to 235 of SEQ ID NO:4; the conserved region containing the position 257 amino acid residue is the sequence of amino acid residues 256 to 269 of SEQ ID NO:5; the conserved region containing the position 287 amino acid residue is the sequence of amino acid residues 282 to 299 of SEQ ID NO:91; the conserved region containing the position 339 amino acid residue is the sequence of amino acid residues 331 to 339 of SEQ ID NO:6; the conserved region containing the position 411 amino acid residue is the sequence of amino acid residues 401 to 416 of SEQ ID NO:7; the conserved region containing the position 470 amino acid residue is the sequence of amino acid residues 468 to 481 of SEQ ID NO:8; the conserved region containing the position 509 amino acid residue is the sequence of amino acid residues 497 to 521 of SEQ ID NO:9; and the conserved region containing the position 574 amino acid residue is the sequence of amino acid residues 570 to 578 of SEQ ID NO:92. The sequence identity described above denotes the sequence identity relative to the sequences of these conserved regions.

Sequence identity to the sequence of each conserved region in the *Arabidopsis thaliana* HMGR shown by SEQ ID NO:1 is as described above, but more preferably is as follows.

For the conserved region containing an amino acid residue at a position corresponding to the position 91 amino acid residue, the sequence identity to the conserved region (SEQ ID NO:3) containing the corresponding position 91 amino acid residue of the *Arabidopsis thaliana* HMGR of SEQ ID NO:1 is preferably at least 71%, more preferably at least 85%, particularly preferably 100%.

For the conserved region containing an amino acid residue at a position corresponding to the position 225 amino acid residue, the sequence identity to the conserved region (SEQ ID NO:4) containing the corresponding position 225 amino acid residue of the *Arabidopsis thaliana* HMGR of SEQ ID NO:1 is preferably at least 64%, more preferably at least 71%, still more preferably at least 78%, particularly preferably at least 85%, most preferably at least 92%, even most preferably 100%.

For the conserved region containing an amino acid residue at a position corresponding to the position 257 amino acid residue, the sequence identity to the conserved region (SEQ ID NO:5) containing the corresponding position 257 amino acid residue of the *Arabidopsis thaliana* HMGR of SEQ ID NO:1 is preferably at least 64%, more preferably at least 71%, still more preferably at least 78%, particularly preferably at least 85%, most preferably at least 92%, even most preferably 100%.

For the conserved region containing an amino acid residue at a position corresponding to the position 287 amino acid residue, the sequence identity to the conserved region (SEQ ID NO:91) containing the corresponding position 287 amino acid residue of the *Arabidopsis thaliana* HMGR of SEQ ID NO:1 is preferably at least 60%, more preferably at least 71%, still more preferably at least 78%, particularly preferably at least 82%, most preferably at least 87%, even most preferably 100%.

For the conserved region containing an amino acid residue at a position corresponding to the position 339 amino acid residue, the sequence identity to the conserved region (SEQ ID NO:6) containing the corresponding position 339 amino acid residue of the *Arabidopsis thaliana* HMGR of SEQ ID NO:1 is preferably at least 66%, more preferably at least 77%, still more preferably at least 88%, particularly preferably 100%.

For the conserved region containing an amino acid residue at a position corresponding to the position 411 amino acid residue, the sequence identity to the conserved region (SEQ ID NO:7) containing the corresponding position 411 amino acid residue of the *Arabidopsis thaliana* HMGR of SEQ ID NO:1 is preferably at least 62%, more preferably at least 68%, still more preferably at least 75%, particularly preferably at least 81%, further particularly preferably at least 87%, most preferably at least 93%, even most preferably 100%.

For the conserved region containing an amino acid residue at a position corresponding to the position 470 amino acid residue, the sequence identity to the conserved region (SEQ ID NO:8) containing the corresponding position 470 amino acid residue of the *Arabidopsis thaliana* HMGR of SEQ ID NO:1 is preferably at least 64%, more preferably at least 71%, still more preferably at least 78%, particularly preferably at least 85%, most preferably at least 92%, even most preferably 100%.

For the conserved region containing an amino acid residue at a position corresponding to the position 509 amino acid residue, the sequence identity to the conserved region (SEQ ID NO:9) containing the corresponding position 509 amino acid residue of the *Arabidopsis thaliana* HMGR of SEQ ID NO:1 is preferably at least 68%, more preferably at least 72%, still more preferably at least 76%, particularly preferably at least 84%, most preferably at least 96%, even most preferably 100%.

For the conserved region containing an amino acid residue at a position corresponding to the position 574 amino acid residue, the sequence identity to the conserved region (SEQ ID NO:92) containing the corresponding position 574 amino acid residue of the *Arabidopsis thaliana* HMGR of SEQ ID NO:1 is preferably at least 71%, more preferably at least 85%, still more preferably 100%.

Serine, threonine, tyrosine, histidine, arginine and lysine are preferred as the amino acid residues at positions 91, 225, 257, 287, 339, 411, 470, 509 and 574 and the amino acid residues at positions corresponding to the foregoing residues, and serine, threonine and tyrosine are more preferred. These amino acid residues can be presumed to participate greatly in controlling HMGR enzyme activity because they are amino acids that are likely to be phosphorylated in vivo.

Specifically, these are threonine at position 91, tyrosine at position 225, tyrosine at position 257, serine at position 287, serine at position 339, serine at position 411, threonine at position 470, threonine at position 509 and tyrosine at position 574 in the *Arabidopsis thaliana* HMGR of SEQ ID NO:1.

As for the amino acid residues at positions corresponding to the amino acid residues at position 91, 225, 257, 287, 339, 411, 470, 509 and 574 of the *Arabidopsis thaliana* HMGR shown by SEQ ID NO:1, in the case of the *Hevea brasiliensis*-derived HMGR (HMG1) represented by SEQ ID NO:10, for example, the threonine at position 91 corresponds to threonine 70, the tyrosine at position 225 to tyrosine 214, the tyrosine at position 257 to tyrosine 246, the serine at position 287 to serine 276, the serine at position 411 to serine 400, the threonine at position 470 to threonine 459, the threonine at position 509 to threonine 498, and the tyrosine at position 574 to tyrosine 563, and there is no amino acid residue corresponding to the serine at position 339 because this HMGR has no conserved region corresponding to the conserved region containing the serine 339.

Moreover, in the case of the *Taraxacum koksaghys*-derived HMGR represented by SEQ ID NO:11, the threonine at position 91 corresponds to threonine 81, the tyrosine at position 225 to tyrosine 223, the serine at position 287 to serine 285, the serine at position 411 to serine 409, the threonine at position 470 to threonine 468, the threonine at position 509 to threonine 507, and the tyrosine at position 574 to tyrosine 572, and there are no amino acid residues corresponding to the tyrosine at position 257 and serine at position 339 because this HMGR has no conserved regions corresponding to the conserved regions containing the tyrosine 257 and serine 339, respectively.

Moreover, in the case of the *Hevea brasiliensis*-derived HMGR (HMG2) represented by SEQ ID NO:70, the serine at position 411 corresponds to serine 35, the threonine at position 470 to threonine 94, the threonine at position 509 to threonine 133, and the tyrosine at position 574 to tyrosine 198, and there are no amino acid residues corresponding to the positions 91, 225, 257 and 339 because this HMGR has no conserved regions corresponding to the conserved regions containing the position 91, 225, 257 and 339 amino acid residues, respectively.

Moreover, in the case of the *Hevea brasiliensis*-derived HMGR (HMG3) represented by SEQ ID NO:71, the threonine at position 91 corresponds to threonine 81, the tyrosine at position 225 to tyrosine 225, the tyrosine at position 257 to tyrosine 257, the serine at position 287 to serine 287, the serine at position 339 to serine 339, the serine at position 411 to serine 411, the threonine at position 470 to threonine 470, the threonine at position 509 to threonine 509, and the tyrosine at position 574 to tyrosine 574.

Moreover, in the case of the *Hevea brasiliensis*-derived HMGR (HMG4) represented by SEQ ID NO:72, the tyrosine at position 225 corresponds to tyrosine 243, the tyrosine at position 257 to tyrosine 275, the serine at position 287 to serine 305, the serine at position 339 to serine 357, the serine at position 411 to serine 429, the threonine at position 470 to threonine 488, the threonine at position 509 to threonine 527, and the tyrosine at position 574 to tyrosine 592, and there is no amino acid residue corresponding to the threonine at position 91 because this HMGR has no conserved region corresponding to the conserved region containing the threonine 91.

Moreover, in the case of the *Hevea brasiliensis*-derived HMGR (HMG5) represented by SEQ ID NO:73, the threonine at position 91 corresponds to threonine 73, the tyrosine at position 225 to tyrosine 243, the serine at position 287 to serine 305, the serine at position 339 to serine 357, the serine at position 411 to serine 429, and the threonine at position 470 to threonine 488, and there are no amino acid residues corresponding to the tyrosine at position 257 and threonine at position 509 because this HMGR has no conserved regions corresponding to the conserved regions containing the tyrosine 257 and threonine 509.

The specific examples including the foregoing examples are shown in Table 1 appearing later.

The mutant protein of the present invention is obtained by an amino acid residue modification in which at least one amino acid residue selected from the group consisting of the amino acid residues at positions 91, 225, 257, 287, 339, 411, 470, 509 and 574 and the amino acid residues at positions corresponding to the foregoing is deleted or replaced with another amino acid residue. With this modification, it is possible to artificially control the reversible phosphorylation of the specific amino acid residues that occurs as necessary in vivo, thereby controlling the enzyme activity of HMGR and therefore mevalonic acid yield. The isoprenoid yield can also be controlled because HMGR is a rate-limiting enzyme in the polyisoprenoid biosynthesis pathway.

The substituted other amino acid residue is not particularly limited as long as it is different from the amino acid before substitution, but is preferably alanine, phenylalanine, cysteine, aspartic acid or glutamic acid. Phosphorylation becomes unlikely particularly when alanine, phenylalanine or cysteine is substituted, while by substituting aspartic acid or glutamic acid it is possible to mimic phosphorylation and obtain a constitutively phosphorylated state. The method for deletion or substitution is not particularly limited, and known methods may be used. For example, a specific amino acid residue can be deleted or substituted by polymerase chain reaction (PCR) using primers overlapping the nucleotide sequence at the deletion or substitution site, in which the three nucleotides coding for the amino acid residue at the deletion or substitution site are either entirely deleted, or replaced with nucleotides coding for another amino acid residue to be substituted (1 to 3 nucleotide substitution).

Preferably at least one amino acid residue selected from the group consisting of the amino acid residues at positions 91, 225, 257, 287, 339, 411, 470, 509 and 574 and the amino acid residues at positions corresponding to the foregoing in HMGR is replaced with aspartic acid or glutamic acid. By replacing the amino acid residue with aspartic acid or glutamic acid, it is possible to mimic the phosphorylated state, or in other words to obtain a constitutively phosphorylated state, thereby controlling the enzyme activity of HMGR.

Moreover, preferably at least one amino acid residue selected from the group consisting of the amino acid residues at positions 91, 225, 257, 287, 339, 411, 470, 509 and 574 and the amino acid residues at positions corresponding to the foregoing in HMGR is deleted or replaced with alanine, phenylalanine or cysteine. By deleting the amino acid residue or replacing it with alanine, phenylalanine or cysteine, it is possible to prevent phosphorylation, or in other words to eliminate a phosphorylation site, thereby controlling the enzyme activity of HMGR.

The deletion, alanine substitution, phenylalanine substitution and cysteine substitution have a similar effect in eliminating a phosphorylation site, but considering the effect of the original amino acid residue on the protein, it is preferred to substitute an amino acid residue having a structure (three-dimensional size, occupied area, etc.) similar to that of the original amino acid residue. Specifically, preferred is phenylalanine substitution when the original amino acid residue is tyrosine, and alanine or cysteine substitution when it is serine or threonine.

In particular, preferably at least one amino acid residue selected from the group consisting of the amino acid residues at positions 91 and 339 and the amino acid residues at positions corresponding to the foregoing is replaced with aspartic acid or glutamic acid; more preferably at least one amino acid residue selected from the group consisting of the amino acid residues at positions 91 and 339 and the amino acid residues at positions corresponding to the foregoing is replaced with aspartic acid or glutamic acid. The enzyme activity of HMGR can be improved by such substitution.

In particular, preferably at least one amino acid residue selected from the group consisting of the amino acid residues at positions 91 and 339 and the amino acid residues at positions corresponding to the foregoing is deleted or replaced with alanine or phenylalanine. By such substitution, the enzyme activity of HMGR can be suppressed or maintained, and it is also possible to suppress the increase in enzyme activity due to phosphorylation because phosphorylation can be suppressed.

In particular, preferably at least one amino acid residue selected from the group consisting of the amino acid residues at positions 225, 257, 287, 411, 470, 509 and 574 and the amino acid residues at positions corresponding to the foregoing is replaced with aspartic acid or glutamic acid. The enzyme activity of HMGR can be reduced or eliminated by such substitution.

In particular, preferably at least one amino acid residue selected from the group consisting of the amino acid residues at positions 225, 257, 287, 411, 470, 509 and 574 and the amino acid residues at positions corresponding to the foregoing is deleted or replaced with alanine, phenylalanine or cysteine. By such substitution, the enzyme activity of HMGR can be maintained, and it is also possible to suppress the deterioration of enzyme activity due to phosphorylation because phosphorylation can be suppressed.

Since even HMGRs having different amino acid residues in conserved regions have a similar function as described above, the HMGR is not particularly limited as long as it has a conserved region corresponding to at least one conserved region selected from the group consisting of the conserved regions containing the amino acid residues at positions 91, 225, 257, 287, 339, 411, 470, 509 and 574 of the *Arabidopsis thaliana* HMGR shown by SEQ ID NO:1, and there is no particular lower limit on the degree of sequence identity to the amino acid sequence of the *Arabidopsis thaliana* HMGR shown by SEQ ID NO:1, but the sequence identity is preferably at least 50%, more preferably at least 60%, still more preferably at least 75%, particularly preferably at least 78%, most preferably at least 80%. Below 50%, the sequence identity to each conserved region described above may not fall within the range indicated above.

Examples of HMGRs other than the *Arabidopsis thaliana* HMGR shown by SEQ ID NO:1 include HMGRs from *Hevea brasiliensis, Oryza sativa, Arabidopsis thaliana, Solanum tuberosum* L., *Solanum lycopersicum, Medicago polymorpha, Lactuca sativa* Lettuce, *Taraxacum koksaghyz, Taraxacum brevicorniculatum* (a species of rubber-producing dandelion), *Parthenium argentatum, Sonchus oleraceus, Manihot esculenta, Eucommia ulmoides,* and *Euphorbia helioscopia* L. Of these, the HMGR is preferably derived from at least one plant species selected from the group consisting of *Hevea brasiliensis, Lactuca sativa, Taraxacum koksaghyz, Taraxacum brevicorniculatum, Parthenium argentatum, Sonchus oleraceus, Manihot esculenta, Arabidopsis thaliana, Eucommia ulmoides,* and *Euphorbia helioscopia* L. *Hevea brasiliensis* HMGR is especially preferred.

The HMGR in the present invention may include multiple types of HMGR present in one biological species, such as HMG1 (S) represented by SEQ ID NO:1, HMG2 represented by SEQ ID NO:69 and the like in the case of *Arabidopsis thaliana* HMGR, and HMG1 represented by SEQ ID NO:10, HMG2 represented by SEQ ID NO:70, HMG3 represented by SEQ ID NO:71, HMG4 represented by SEQ ID NO:72, HMG5 represented by SEQ ID NO:73 and the like in the case of *Hevea brasiliensis* HMGR. Other examples are shown in Table 1.

The mutant protein of the present invention may be produced by conventionally known methods, i.e. by preparing a recombinant vector as described later, and using a microorganism, yeast, animal cell, insect cell, plant cell, animal, insect, plant or the like capable of expressing a target protein to prepare a transformant having an introduced gene coding for the target protein to express the target protein. Conventionally known methods may also be used to purify the mutant protein of the present invention, and for example the mutant protein can be easily purified with a specific column if it is expressed with a His tag or the like fused to the target protein.

Conventionally known methods may be used to determine the enzyme activity of the mutant protein of the present invention, such as for example a method of preparing a transformant having an introduced gene coding for a target protein using, for example, *E. coli*, to express the target protein, and determining the presence or absence of the function of the target protein by the corresponding activity measurement method to determine the activity.

(Gene)

The gene of the present invention is a gene coding for the mutant protein. Since the gene codes for the mutant protein, a mutant protein expressed by this gene can be used to control HMGR enzyme activity and therefore mevalonic acid yield. The isoprenoid yield can also be controlled because HMGR is a rate-limiting enzyme in the polyisoprenoid biosynthesis pathway.

Examples of the gene of the present invention include a DNA having the nucleotide sequence of nucleotides 1 to 1776 of SEQ ID NO:12, a DNA that hybridizes under stringent conditions with a DNA having a nucleotide sequence complementary to the nucleotide sequence of nucleotides 1 to 1776 of SEQ ID NO:12, and that codes for a protein having HMGR activity, and a DNA that has at least 60%, preferably at least 80%, more preferably at least 90%, still more preferably at least 95%, particularly preferably at least 98% sequence identity to the nucleotide sequence of nucleotides 1 to 1776 of SEQ ID NO:12, and that codes for a protein having HMGR activity.

"Hybridize" as used herein refers to a step of hybridizing a DNA with a DNA having a specific nucleotide sequence, or with a part of such a DNA. Thus, the DNA having a specific nucleotide sequence or part of such a DNA may have a nucleotide sequence long enough to be usable as a probe in northern or southern blot analysis or as an oligonucleotide primer in PCR analysis. The DNA used as a probe may have a length of at least 100 bases, preferably at least 200 bases, more preferably at least 500 bases although it may be a DNA of at least 10 bases, preferably of at least 15 bases in length.

Techniques to perform DNA hybridization experiments are well known. The hybridization conditions under which experiments are carried out may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

Conventional known methods may be used to confirm that the DNA that hybridizes with the DNA under stringent conditions described above codes for a specific protein, and for example the nucleotide sequence may be confirmed with a sequencer, for example.

(Recombinant Vector)

The gene of the present invention can be introduced into a plasmid to obtain a recombinant vector carrying a gene coding for the HMGR. This recombinant vector can be used to cause expression of a target protein in *E. coli* or the like, or as a vector for producing a further transformant. The plasmid for introduction is not particularly limited.

When the recombinant vector is used to express a target protein, the host is preferably, but not limited to, a eukaryote although any microorganism, yeast, animal cell, insect cell, plant cell, animal, insect, plant or the like capable of expressing the target protein may be used.

(Transformant)

The gene of the present invention can be introduced into a host to obtain a transformant carrying a gene coding for the HMGR described above. Since the HMGR enzyme activity is obtained in vivo in the transformant with the introduced gene in which the target protein is expressed, it is possible to increase, reduce or otherwise control the yield of mevalonic acid catalyzed and biosynthesized by the HMGR. Therefore, with a transformant of an isoprenoid-producing plant it is presumably possible to control isoprenoid yield because the activity of HMGR, which is a rate-limiting enzyme in the isoprenoid biosynthesis pathway, is controlled in vivo in the transformant with the introduced gene.

The host used for the transformant is not particularly limited as long as it is an organism possessing HMGR, but isoprenoid-producing plants, among others, are preferred in order to control mevalonic acid yield and therefore isoprenoid yield. Examples of isoprenoid-producing plants include *Hevea brasiliensis* and other *Hevea* species; *Sonchus oleraceus, Sonchus asper, Sonchus brachyotus* and other *Sonchus* species; *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea, Solidago gigantea* Ait. var. *leiophylla* Fernald and other *Solidago* species; *Helianthus annuus, Helianthus argophyllus, Helianthus atrorubens, Helianthus debilis, Helianthus decapetalus, Helianthus giganteus* and other *Helianthus* species; dandelion (*Taraxacum*), *Taraxacum venustum* H. Koidz, *Taraxacum hondoense* Nakai, *Taraxacum platycarpum* Dahlst, *Taraxacum japonicum, Taraxacum officinale* Weber, *Taraxacum koksaghyz, Taraxacum brevicorniculatum* (a species of rubber-producing dandelion) and other *Taraxacum* species; *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., *Ficus benghalensis* and other *Ficus* species; *Parthenium argentatum, Parthenium hysterophorus, Ambrosia artemisiifolia* (*Parthenium hysterophorus*) and other *Parthenium* species; *Euphorbia helioscopia* L., *Euphorbia lasiocaula* Boiss and other *Euphorbia* species; and *Lactuca sativa* Lettuce, and other *Lactuca* species; *Manihot esculenta* and other *Manihot* species; *Eucommia ulmoides* and other *Eucommia* species; *Arabidopsis thaliana* and other *Arabidopsis* species; and the like. Of these, the isoprenoid-producing plant is preferably at least one selected from the group consisting of plants of the genera *Hevea, Sonchus, Taraxacum, Parthenium, Lactuca, Manihot, Arabidopsis, Eucommia* and *Euphorbia*, more preferably at least one selected from the group consisting of *Hevea brasiliensis, Lactuca sativa, Taraxacum koksaghyz, Taraxacum brevicorniculatum, Parthenium argentatum, Sonchus oleraceus, Manihot esculenta, Arabidopsis thaliana, Eucommia ulmoides* and *Euphorbia helioscopia* L., and is still more preferably *Hevea brasiliensis, Lactuca sativa* or *Taraxacum koksaghyz*.

The recombinant vector described above may be used as the expression vector, and those capable of autonomous replication in the host cells or of being incorporated into the chromosome thereof may be used.

Known expression vectors may be used, such as pET160, pBI or pUC vectors, Ti plasmids, and tobacco mosaic virus vectors.

Any method for introducing DNA into plant cells may be used to introduce the recombinant vector. Examples include methods using Agrobacterium (JP-A S59-140885, JP-A S60-70080, WO 94/00977), electroporation methods (JP-A S60-251887), and methods using particle guns (JP-B 2606856, JP-B 2517813) and the like.

The transformant (transgenic plant cell) can be produced by the above or other methods.

(Point Mutation Breeding)

A plant having the modified HMGR may also be produced by mutation breeding techniques using the nucleotide sequence of the relevant site as a breeding marker. Ordinary mutant plant production methods and ordinary mutation screening methods such as Targeting Induced Local Lesions IN Genomes (TILLING) may be used as mutation breeding techniques. Since the gene of the invention is contained in the mutant (mutant plant cells) as a result of a point mutation, and thus the modified HMGR is expressed in place of the wild-type HMGR to provide the HMGR enzyme activity, it is possible to increase, reduce and otherwise control the yield of mevalonic acid catalyzed and biosynthesized by the HMGR. Therefore, with a mutant of an isoprenoid-producing plant, it is presumably possible to control isoprenoid yield because the activity of HMGR, a rate-limiting enzyme in the isoprenoid biosynthesis pathway, is controlled in the mutant.

The present invention also provides an isoprenoid-producing plant carrying the gene of the present invention. The isoprenoid-producing plant is not particularly limited as long as it is an isoprenoid-producing plant containing transgenic plant cells or mutant plant cells. The isoprenoid-producing plant conceptually includes not only transgenic plant cells or mutant plant cells produced as described above, but also, for example, all of their progeny or clones and even progeny plants obtained by passaging these cells. Once a transgenic plant cell having the DNA or vector introduced into its genome or a mutant plant cell expressing the HMGR modified by a point mutation is obtained, progeny or clones can be obtained from the transgenic plant cell or mutant plant cell by sexual or asexual reproduction, tissue culture, cell culture, cell fusion, or other techniques. Further, the transgenic plant cell or mutant plant cell, or their progeny or clones may be used to obtain reproductive materials (e.g. seeds, fruits, cuttings, stem tubers, root tubers, shoots, adventitious buds, adventitious embryos, calluses, protoplasts), which can then be used to mass produce the isoprenoid-producing plant.

Techniques to regenerate plants from transgenic plant cells or mutant plant cells are already known; for example, Doi et al. disclose techniques for eucalyptus (JP-A H11-127025), Fujimura et al. disclose techniques for rice (Fujimura et al., (1995), Plant Tissue Culture Lett., vol. 2: p. 74-), Shillito et al. disclose techniques for corn (Shillito et al., (1989), Bio/Technology, vol. 7: p. 581-), Visser et al. disclose techniques for potato (Visser et al., (1989), Theor. Appl. Genet., vol. 78: p. 589-), and Akama et al. disclose techniques for *Arabidopsis thaliana* (Akama et al., (1992), Plant Cell Rep., vol. 12: p. 7-). Those skilled in the art can regenerate plants from transgenic plant cells or mutant plant cells according to these documents.

Whether a target protein gene is expressed in a regenerated plant may be determined by well-known methods. For example, western blot analysis may be used to assess the expression of a target protein.

Seeds can be obtained from the transgenic plant or mutant plant, for example, as follows: the transgenic plant or mutant plant is rooted in an appropriate medium, transplanted to water-containing soil in a pot, and grown under proper cultivation conditions so as to finally produce seeds, which are then collected. Further, plants can be grown from seeds, for example, as follows: seeds obtained from the transgenic plant or mutant plant as described above are sown in water-containing soil, and grown under proper cultivation conditions into plants.

In the present invention, mevalonic acid yield, isoprenoid yield and polyisoprenoid yield can be controlled by using an isoprenoid-producing plant carrying the gene of the present invention to produce mevalonic acid, isoprenoids and polyisoprenoids. Specifically, a transgenic plant cell or mutant plant cell obtained as described above, a callus obtained from the transgenic plant cell or mutant plant cell, a cell re-differentiated from that callus, or the like may be cultured in an appropriate medium, or a transgenic plant regenerated from the transgenic plant cell, a mutant plant regenerated from the mutant plant cell, a plant grown from a seed obtained from the transgenic plant or mutant plant, or the like can be grown under proper cultivation conditions to produce mevalonic acid, isoprenoids and polyisoprenoids. Since the enzyme activity of the rate-limiting enzyme in the mevalonic acid, isoprenoid and polyisoprenoid biosynthesis pathways is controlled by a modified protein in the transformant or mutant of the present invention, it is possible to control the yield of mevalonic acid catalyzed and biosynthesized by that protein (enzyme), and therefore to control isoprenoid yield and, further, polyisoprenoid yield.

In the Description, "polyisoprenoid" is generic term used to refer to polymers having isoprene ($C_5H_8$) units. Examples of polyisoprenoids include polymers such as monoterpenes ($C_{10}$) sesquiterpenes ($C_{15}$) diterpenes ($C_{20}$) sesterterpenes ($C_{25}$) triterpenes ($C_{30}$) tetraterpenes ($C_{40}$), and natural rubber. In the Description, "isoprenoid" refers to a compound having an isoprene ($C_5H_8$) unit, and conceptually includes polyisoprenoids.

In the present invention, mevalonic acid yield, isoprenoid yield and polyisoprenoid yield can be controlled by modifying at least one amino acid residue out of the 9 amino acid residues described above, but the effects of the invention are more notable if two or more of the 9 amino acid residues are modified.

EXAMPLES

The present invention is explained in detail with reference to examples, but the present invention is not limited to these examples.

(Suggestive Evidence for Presence of New Phosphorylation Site)

A mutant HMGR1 (hereunder called S577A-HMGR1) having a substitution of alanine for serine 577, the phosphorylation of which is known to reduce enzyme activity, in HMGR1 from *Arabidopsis thaliana* was transfected into an *Arabidopsis thaliana* mutant lacking endogenous HMGR1, to produce an *Arabidopsis thaliana* transformant expressing S577A-HMGR1. An ER fraction was collected from this transgenic plant expressing S577A-HMGR1 (HMGR is an ER-localized membrane protein). When the ER fraction containing S577A-HMGR1 was phosphatase treated, the enzyme activity was found to be elevated in the same way as when an ER fraction containing wild-type HMGR from *Arabidopsis thaliana* expressing wild-type HMGR1 was phosphatase treated. Western blotting confirmed that the accumulated amounts of HMGR in the S577A-HMGR1-expressing transgenic plant and the wild-type HMGR1-expressing transgenic plant were comparable. This suggests the presence of a new phosphorylation site (amino acid residue) other than the known phosphorylation site (serine 577) that is involved in controlling the enzyme activity of HMGR.

(Inferring HMGR Phosphorylation Site In Silico)

Multiple sequence alignment was performed on the plants shown in Table 1 to search for highly conserved sequence parts (conserved regions). At the same time, amino acid residues that might undergo phosphorylation were screened from the full-length sequences, and anticipated phosphorylation sites contained in the conserved regions were selected from these residues. The results are shown in Table 1.

The software used for multiple sequence alignment was called identityX, and that used for screening amino acid residues that might undergo phosphorylation (phosphorylation sites) was called PhosPhAt.
(Construction of HMGR Expression Vector)

The sequence of SEQ ID NO:12, which is an S-type DNA sequence of the *Arabidopsis thaliana*-derived HMGR shown by SEQ ID NO:1 (hereunder also referred to as HMG1S), was amplified by PCR using the primers shown below. The resulting PCR product was cloned to pENTR/D-TOPO by the heat shock method using *E. coli* to obtain an entry vector called pENTR/HMG1S. The entry vector was prepared with a pENTR Directional TOPO Cloning Kit using DH5α as the *E. coli*.

```
(Primer 1: SEQ ID NO: 13)
5'-CACCATGGATCTCCGTCGGAGGCCTC-3'

(Primer 2: SEQ ID NO: 14)
5'-CGCCTCGAGTCATGTTGTTGTTGTCG-3'
```

(Preparation of Expression Vector (Recombinant Vector))

Using the pENTR/HMG1S obtained above, the gene sequence part of the target protein was recombined and transfected into pET160-DEST to obtain a pDEST/HMG1S expression vector. LR reaction of Gateway system (Invitrogen) was used for the recombination reaction.
(Preparation of Mutant HMGR Expression Vector)

A PCR reaction was performed with PrimeSTAR HS (Takara) using the pDEST/HMG1S as a template. The composition per sample (25 μl) of the PCR reaction solution was 1 to 5 ng of plasmid, 0.75 μl of each of the forward and reverse primers (each 10 pmol/μl) shown below for each mutation, 5 μl of 5× buffer for primestar (Mg$^{2+}$), 2 μl of dNTPmix, 0.25 μl of primestar HS, and 15.75 μl of milliQ water. The PCR was carried out using the following predetermined reaction cycle: step 1: 2 minutes at 98° C., step 2: 10 seconds at 98° C., step 3: 15 seconds at 60° C., step 4: 8 minutes at 68° C., steps 2 to 4 repeated 17 times. A part of the PCR product (7 μl) was electrophoresed, and when amplification was observed, 0.2 μl of DpnI was added to the remainder of the PCR product and reacted for 3 hours at 37° C. 2 μl of the reaction solution was added to 20 μl of self-made *E. coli* (DH5α) chemically competent cells, and the cells were transformed by the heat shock method. All of the bacterial culture was inoculated on LB agar medium containing 50 μg/ml ampicillin and cultured overnight at 37° C. After culture, the resulting colonies were screened by colony PCR. Plasmid extraction was performed with a Qiagen Plasmid mini kit, and insertion of the mutation was verified by sequencing, to obtain a desired mutant HMG1S expression vector. A total of 34 types of mutant HMG1S expression vectors were prepared by this method. A serine-577 mutant HMG1S as a positive control was also included. The sequence verification was carried out with a BigDye Terminator Cycle Sequencing V3.0 Ready Reaction Kit (Applied Biosystems) using an ABI3130XI sequencer.

The primers used in preparing each mutant HMG1S are shown below.
(Primers Used to Mutate Tyrosine 225 of HMG1S)
(Primers Used for pHMG1S/Y225F)

```
(Primer 3 (forward): SEQ ID NO: 15)
5'-ttgatTTTgaatcgattttggggcaatgc-3'

(Primer 4 (reverse): SEQ ID NO: 16)
5'-ttgatTTTgaatcgattttggggcaatgc-3'
```

(Primers Used for pHMG1S/Y225D)

```
(Primer 5 (forward): SEQ ID NO: 17)
5'-ttaccgttggatggatttgatGATgaatcgattttggggcaatgc-3'

(Primer 6 (reverse): SEQ ID NO: 18)
5'-gcattgccccaaaatcgattcGGCatcaaatccatccaacggtaa-3'
```

(Primers Used for pHMG1S/Y225E)

```
(Primer 7 (forward): SEQ ID NO: 19)
5'-ttaccgttggatggatttgatGAGgaatcgattttggggcaatgc-3'

(Primer 8 (reverse): SEQ ID NO: 20)
5'-gcattgccccaaaatcgattcCTCatcaaatccatccaacggtaa-3'
```

<Primers Used to Mutate Tyrosine 257 of HMG1S>
(Primers Used for pHMG1S/Y257F)

```
(Primer 9 (forward): SEQ ID NO: 21)
5'-atgagTTCtctgttcctatggctacaacc-3'

(Primer 10 (reverse): SEQ ID NO: 22)
5'-acagaGAActcataaccatcaagcaacaa-3'
```

(Primers Used for pHMG1S/Y257D)

```
(Primer 11 (forward): SEQ ID NO: 23)
5'-ttgttgcttgatggttatgagGACtctgttcctatggctacaacc-3'

(Primer 12 (reverse): SEQ ID NO: 24)
5'-ggttgtagccataggaacagaGTCctcataaccatcaagcaacaa-3'
```

(Primers Used for pHMG1S/Y257E)

```
(Primer 13 (forward): SEQ ID NO: 25)
5'-ttgttgattgatggttatgagGAAtctgttcctatggctacaacc-3'

(Primer 14 (reverse): SEQ ID NO: 26)
5'-ggttgtagccataggaacagaTTCctcataaccatcaagcaacaa-3'
```

<Primers Used to Mutate Serine 411 of HMG1S>
(Primers Used for pHMG1S/S411A)

```
(Primer 15 (forward): SEQ ID NO: 27)
5'-ggattgagggacgtggtaaaGCAgttgtttgcgaggctgtaatc-3'

(Primer 16 (reverse): SEQ ID NO: 28)
5'-gattacagcctcgcaaacaacTGCtttaccacgtccctcaatcc-3'
```

(Primers Used for pHMG1S/S411D)

(Primer 17 (forward): SEQ ID NO: 29)
5'-ggattgagggacgtggtaaaGATgttgtttgcgaggctgtaatc-3'

(Primer 18 (reverse): SEQ ID NO: 30)
5'-gattacagcctcgcaaacaacATCtttaccacgtccctcaatcc-3'

(Primers Used for pHMG1S/S411E)

(Primer 19 (forward): SEQ ID NO: 31)
5'-ggattgagggacgtggtaaaGAAgttgtttgcgaggctgtaatc-3'

(Primer 20 (reverse): SEQ ID NO: 32)
5'-gattacagcctcgcaaacaacTTCtttaccacgtccctcaatcc-3'

<Primers Used to Mutate Threonine 470 of HMG1S>
(Primers Used for pHMG1S/T470A)

(Primer 21 (forward): SEQ ID NO: 33)
5'-gctGCAggccaagatccagctcaaaacgtg-3'

(Primer 22 (reverse): SEQ ID NO: 34)
5'-ggccTGCagctatgaatacagcagacac-3'

(Primers Used for pHMG1S/T470D)

(Primer 23 (forward): SEQ ID NO: 35)
5'-gctGATggccaagatccagctcaaaacgtg-3'

(Primer 24 (reverse): SEQ ID NO: 36)
5'-ggccATCagctatgaatacagcagacac-3'

(Primers Used for pHMG1S/T470E)

(Primer 25 (forward): SEQ ID NO: 37)
5'-gctGAAggccaagatccagctcaaaacgtg-3'

(Primer 26 (reverse): SEQ ID NO: 38)
5'-ggccTTCagctatgaatacagcagacac-3'

<Primers Used to Mutate Threonine 509 of HMG1S>
(Primers Used for pHMG1S/T509A)

(Primer 27 (forward): SEQ ID NO: 39)
5'-ccatctatcgaggtggggGCAgtgggaggaggaacacagcttgc-3'

(Primer 28 (reverse): SEQ ID NO: 40)
5'-gcaagctgtgttcctcctcccacTGCccccacctcgatagatgg-3'

(Primers Used for pHMG1S/T509D)

(Primer 29 (forward): SEQ ID NO: 41)
5'-ccatctatcgaggtggggGATgtgggaggaggaacacagcttgc-3'

(Primer 30 (reverse): SEQ ID NO: 42)
5'-gcaagctgtgttcctcctcccacATCccccacctcgatagatgg-3'

(Primers Used for pHMG1S/T509E)

(Primer 31 (forward): SEQ ID NO: 43)
5'-ccatctatcgaggtggggGAAgtgggaggaggaacacagcttgc-3'

-continued (Primer 32 (reverse): SEQ ID NO: 44)
5'-gcaagctgtgttcctcctcccacTTCccccacctcgatagatgg-3'

<Primers Used to Mutate Serine 48 of HMG1S>
(Primers Used for pHMG1S/S48A)

(Primer 33 (forward): SEQ ID NO: 45)
5'-attgctcctccaccgaaagcaGCCgacgcgcttcctcttccgtta-3'

(Primer 34 (reverse): SEQ ID NO: 46)
5'-taacggaagaggaagcgcgtcGGCtgctttcggtggaggagcaat-3'

(Primers Used for pHMG1S/S48D)

(Primer 35 (forward): SEQ ID NO: 47)
5'-attgctcctccaccgaaagcaGACgacgcgcttcctcttccgtta-3'

(Primer 36 (reverse): SEQ ID NO: 48)
5'-taacggaagaggaagcgcgtcGTCtgctttcggtggaggagcaat-3'

(Primers Used for pHMG1S/S48E)

(Primer 37 (forward): SEQ ID NO: 49)
5'-attgctcctccaccgaaagcaGAAgacgcgcttcctcttccgtta-3'

(Primer 38 (reverse): SEQ ID NO: 50)
5'-taacggaagaggaagcgcgtcTTCtgctttcggtggaggagcaat-3'

<Primers Used to Mutate Threonine 91 of HMG1S>
(Primers Used for pHMG1S/T91A)

(Primer 39 (forward): SEQ ID NO: 51)
5'-aatacgcctcttcacgtcgtcGCAatcacagaactcggcgccatt-3'

(Primer 40 (reverse): SEQ ID NO: 52)
5'-aatggcgccgagttctgtgatTGCgacgacgtgaagaggcgtatt-3'

(Primers Used for pHMG1S/T91D)

(Primer 41 (forward): SEQ ID NO: 53)
5'-aatacgcctcttcacgtcgtcGATatcacagaactcggcgccatt-3'

(Primer 42 (reverse): SEQ ID NO: 54)
5'-aatggcgccgagttctgtgatATCgacgacgtgaagaggcgtatt-3'

(Primers Used for pHMG1S/T91E)

(Primer 43 (forward): SEQ ID NO: 55)
5'-aatacgcctcttcacgtcgtcGAAatcacagaactcggcgccatt-3'

-continued (Primer 44 (reverse): SEQ ID NO: 56)
5'-aatggcgccgagttctgtgatTTCgacgacgtgaagaggcgtatt-3'

<Primers Used to Mutate Serine 339 of HMG1S>
(Primers Used for pHMG1S/S339A)

(Primer 45 (forward): SEQ ID NO: 57)
5'-cgagtagatttgcaagactgcaaGCCgttaaatgcacaatcgc-3'

(Primer 46 (reverse): SEQ ID NO: 58)
5'-gcgattgtgcatttaacGGCttgcagtcttgcaaatctactcg-3'

(Primers Used for pHMG1S/S339D)

(Primer 47 (forward): SEQ ID NO: 59)
5'-cgagtagatttgcaagactgcaaGATgttaaatgcacaatcgc-3'

(Primer 48 (reverse): SEQ ID NO: 60)
5'-gcgattgtgcatttaacATCttgcagtcttgcaaatctactcg-3'

(Primers Used for pHMG1S/S339E)

(Primer 49 (forward): SEQ ID NO: 61)
5'-cgagtagatttgcaagactgcaaGAAgttaaatgcacaatcgc-3'

(Primer 50 (reverse): SEQ ID NO: 62)
5'-gcgattgtgcatttaacTTCttgcagtcttgcaaatctactcg-3'

<Primers Used to Mutate Serine 287 of HMG1S>
(Primers Used for pHMG1S/S287A)

(Primer 57 (forward): SEQ ID NO: 93)
5'-cttgtcaggtggggccaccGCCgtcttgttgaaggatggcatgac-3'

(Primer 58 (reverse): SEQ ID NO: 94)
5'-gtcatgccatccttcaacaagacGGCggtggccccacctgacaag-3'

(Primers Used for pHMG1S/S287D)

(Primer 59 (forward): SEQ ID NO: 95)
5'-gctatgtttatctctggtggcgccaccGATaccgttcttaagga-3'

(Primer 60 (reverse): SEQ ID NO: 96)
5'-tccttaagaacggtATCggtggcgccaccagagataaacatagc-3'

(Primers Used for pHMG1S/S287E)

(Primer 61 (forward): SEQ ID NO: 97)
5'-cttgtcaggtggggccaccGAAgtcttgttgaaggatggcatgac-3'

(Primer 62 (reverse): SEQ ID NO: 98)
5'-gtcatgccatccttcaacaagacTTCggtggccccacctgacaag-3'

<Primers Used to Mutate Tyrosine 574 of HMG1S>
(Primers Used for pHMG1S/Y574A)

(Primer 113 (forward): SEQ ID NO: 150)
5'-gtcaagagtcacatgaagGCCaacagatccagcaaagatatgtct-3'

(Primer 114 (reverse): SEQ ID NO: 151)
5'-agacatatctttgctggatctgttGGCcttcatgtgactcttgac-3'

(Primers Used for pHMG1S/Y574F)

(Primer 63 (forward): SEQ ID NO: 99)
5'-gtcaagagtcacatgaagTTCaacagatccagcaaagatatgtct-3'

(Primer 64 (reverse): SEQ ID NO: 100)
5'-agacatatctttgctggatctgttGAActtcatgtgactcttgac-3'

(Primers Used for pHMG1S/Y574D)

(Primer 65 (forward): SEQ ID NO: 101)
5'-gtcaagagtcacatgaagGACaacagatccagcaaagatatgtct-3'

(Primer 66 (reverse): SEQ ID NO: 102)
5'-agacatatctttgctggatctgttGTCcttcatgtgactcttgac-3'

(Primers Used for pHMG1S/Y574E)

(Primer 67 (forward): SEQ ID NO: 103)
5'-gtcaagagtcacatgaagGAAacagatccagcaaagatatgtct-3'

(Primer 68 (reverse): SEQ ID NO: 104)
5'-agacatatctttgctggatctgttTTCcttcatgtgactcttgac-3'

<Primers Used to Mutate Serine 577 of HMG1S>
(Primers Used for pHMG1S/S577A)

(Primer 51 (forward): SEQ ID NO: 63)
5'-caatagaGCCagccgagacatctctggagcaacg-3'

(Primer 52 (reverse): SEQ ID NO: 64)
5'-cggctGGCtctattgtatttcatgtgacttctcac-3'

(Primers Used for pHMG1S/S577D)

(Primer 53 (forward): SEQ ID NO: 65)
5'-gtcacatgaaatacaatagaGACagccgagacatctctggagc-3'

(Primer 54 (reverse): SEQ ID NO: 66)
5'-gctccagagatgtctcggctGTCtctattgtatttcatgtgac-3'

(Primers Used for pHMG1S/S577E)

(Primer 55 (forward): SEQ ID NO: 67)
5'-gtcacatgaaatacaatagaGAAagccgagacatctctggagc-3'

(Primer 56 (reverse): SEQ ID NO: 68)
5'-gctccagagatgtctcggctTTCtctattgtatttcatgtgac-3'

(Preparation of Transformant Expressing Mutant HMGR)

E. coli was transformed by the heat shock method using each of the mutant HMG1S expression vectors obtained above, to obtain transformants expressing each mutant HMG1S. BL21 Star (DE3) was used as the E. coli.

(Expression of Mutant HMGR)

Each of the E. coli transformants expressing each mutant HMG1S obtained above was cultured overnight at 37° C. in 2 ml of LB liquid medium, and the bacterial culture after culture was transferred to 50 ml of LB liquid medium and then shake-cultured at 37° C. for 2 hours, after which IPTG was added to a final concentration of 0.5 mM, and the cells were cultured for 6 hours at 20° C. Ampicillin was added to all the LB liquid media to a concentration of 50 μg/ml. The entire amount of each bacterial culture after completion of all culture steps was centrifuged for 5 minutes at 4° C. and 5000 g to collect the cells, and the pellets were stored at −20° C.

(Collection and Purification of Mutant HMGR)

Each of the bacterial cell samples obtained above was dissolved in binding buffer (40 mM sodium phosphate (pH 8.0), 1 mM EDTA, 300 mM sodium chloride, 0.1% TritonX-100, 10% glycerol, 0.8 mM imidazole) supplemented with 100 μM AEBSF, 10 μM Leupeptin, 10 mM DTT and 0.1% lysozyme. The bacterial cells were disrupted (disruption conditions: Duty cycle 50%, Output control 2.5, 1 minute×3) with a Sonifier 450 sonicator (Branson) while being cooled on ice. These were then centrifuged for 15 minutes at 4° C. and 15,000 rpm, and 100 μl of Ni-NTA Agarose (Qiagen) that had been washed three times in advance with binding buffer was added to the supernatant. The mixture was rotary shaken for 1 hour at 4° C. and then centrifuged for 5 minutes at 4° C. and 8000 rpm. The resin was transferred to an empty column (Bio-Rad) and washed three times with washing buffer (20 mM imidazole, other components as in binding buffer). 15 μl of elution buffer (430 mM imidazole, other components as in binding buffer) supplemented with 100 μM AEBSF, 10 μM Leupeptin and 10 mM DTT was added to the resin, which was then eluted by 1 minute of centrifugation at 4° C. and 15,000 rpm. An additional 20 μl of elution buffer was added to the resin, which was then eluted by 1 minute of centrifugation at 4° C. and 15,000 rpm. A total of 35 μl of His-tag purified mutant HMG1S protein solution was obtained.

The quantity and purity of each resulting protein were verified by polyacrylamide gel electrophoresis (SDS-PAGE). For quantification, BSA standard solutions (100 ng, 300 ng, 1 μg) were electrophoresed at the same time, and band strength was detected and determined from the gel after CBB staining using Gel Doc XR+ and Image Lab.

(Determination of Enzyme Activity of Mutant HMGR)

1.65 ng of each of the HMG1S mutants obtained after purification was added to a reaction solution (1 mM NADPH, 0.4 mg/ml BSA, 40 mM sodium phosphate (pH 8.0), 1 mM EDTA, 50 mM sodium chloride, 1% TritonX-100, 10% glycerol, 4 mM DTT), and pre-incubated for 5 minutes at 37° C., after which 20 μM HMG-CoA (Perkin Elmer) labeled with $^{14}C$ was added (final reaction solution volume 26 μl), and the mixture was reacted for 15 minutes at 37° C. 5 μl of 1 mg/ml mevalonic lactone and 5 μl of 6N hydrochloric acid were added, and the mixture was left for 15 minutes at room temperature and then neutralized by addition of 125 μl of saturated potassium phosphate buffer at pH 6.0. 300 μl of ethyl acetate was added and mixed vigorously, and the mixture was centrifuged for 5 minutes at 20° C. and 15,000 rpm. The ethyl acetate layer of the supernatant was analyzed for radioactivity in a liquid scintillation counter. The enzyme activity results for each mutant HMG1S are shown in Table 2. The enzyme activities are expressed as specific activity, with wild-type HMG1S set equal to 1.

TABLE 1

| Biological species and/or target proteins | Amino acid residue substitution site | | | | | | | | Sequence identity (%) to amino acid sequence of SEQ ID NO: 1 | Note |
|---|---|---|---|---|---|---|---|---|---|---|
| Arabidopsis thaliana HMG1(S) (HMGR(S) type) from Arabidopsis thaliana | T91 | Y225 | Y257 | S287 | S339 | S411 | T470 | T509 | Y574 | — | SEQ ID NO: 1 |
| Arabidopsis thaliana HMG2 | — | Y200 (92.8) | Y232 (100) | S262 (72.2%) | S314 (100) | — | T445 (100) | T482 (88.0) | Y547 (100) | 65.2 | SEQ ID NO: 69 |
| Hevea brasiliensis HMG1 | T70 (85.7) | Y214 (100) | Y246 (100) | S276 (88.9%) | — | S400 (100) | T459 (100) | T498 (100) | Y563 (100) | 84.8 | SEQ ID NO: 10 |
| Hevea brasiliensis HMG2 | — | — | — | — | — | S35 (100) | T94 (100) | T133 (96.0) | Y198 (100) | 85.2 | SEQ ID NO: 70 (partial length) |
| Hevea brasiliensis HMG3 | T81 (85.7) | Y225 (100) | Y257 (92.8) | S287 (83.3%) | S339 (100) | S411 (100) | T470 (100) | T509 (92.0) | Y574 (88.9) | 80.5 | SEQ ID NO: 71 |
| Hevea brasiliensis HMG4 | — | Y243 (100) | Y275 (100) | S305 (83.3%) | S357 (88.9) | S429 (100) | T488 (100) | T527 (96.0) | Y592 (77.8) | 79.7 | SEQ ID NO: 72 |
| Hevea brasiliensis HMG5 | T73 (85.7) | Y243 (100) | — | S305 (88.9%) | S357 (88.9) | S429 (93.8) | T488 (100) | — | — | 80.5 | SEQ ID NO: 73 |
| Lactuca sativa Lettuce(TC18019) | — | Y204 (92.8) | — | S266 (88.9%) | — | S390 (100) | T449 (85.7) | — | — | 81.0 | SEQ ID NO: 74 (partial length) |
| Lactuca sativa Lettuce(TC23858) | T82 (100) | Y226 (92.8) | — | — | — | S412 (100) | T471 (85.7) | T510 (92.0) | Y575 (88.9) | 64.6 | SEQ ID NO: 75 |
| Lactuca sativa Lettuce(TC19509) | T96 (85.7) | Y237 (100) | — | — | S351 (77.8) | S423 (100) | — | — | — | 61.4 | SEQ ID NO: 76 (partial length) |
| Lactuca sativa Lettuce(TC22046) | — | Y20 (92.8) | — | — | S134 (88.9) | S206 (100) | T265 (92.8) | — | — | 82.7 | SEQ ID NO: 77 (partial length) |
| Lactuca sativa Lettuce(TC22228) | — | — | — | — | S82 (77.8) | S154 (100) | T213 (100) | T252 (92.0) | — | 61.0 | SEQ ID NO: 78 (partial length) |
| Lactuca sativa Lettuce(TC23348) | — | — | — | — | — | — | T51 (92.8) | T90 (100) | Y155 (88.9) | 82.8 | SEQ ID NO: 79 (partial length) |
| Taraxacum koksaghys (HQ857601) | T81 (100) | Y223 (92.8) | — | S285 (88.9%) | — | S409 (100) | T468 (85.7) | T507 (96.0) | Y572 (88.9) | 65.2 | SEQ ID NO: 11 |
| Manihot esculenta (003982m) | T73 (100) | Y240 (100) | — | S302 (83.3%) | S354 (88.9) | S426 (100) | T485 (100) | T524 (96.0) | Y589 (88.9) | 64.7 | SEQ ID NO: 80 |
| Manihot esculenta (004209m) | T84 (85.7) | Y228 (100) | Y260 (100) | S290 (83.3%) | — | S414 (100) | T473 (100) | T512 (100) | Y577 (100) | 76.7 | SEQ ID NO: 81 |

TABLE 1-continued

| Biological species and/or target proteins | Amino acid residue substitution site | | | | | | | | | Sequence identity (%) to amino acid sequence of SEQ ID NO: 1 | Note |
|---|---|---|---|---|---|---|---|---|---|---|---|
| Eucommia ulmodes (AAV54051) | T85 (85.7) | Y228 (92.8) | Y260 (100) | S290 (83.3%) | — | S414 (100) | T473 (92.8) | T512 (100) | Y577 (88.9) | 73.5 | SEQ ID NO: 82 |
| Euphorbia helioscopia L.(ABK56831) | T79 (85.7) | Y221 (100) | Y253 (100) | S283 (83.3%) | — | — | T466 (100) | T505 (100) | Y570 (88.9) | 75.0 | SEQ ID NO: 83 |
| Oryza sativa HMG1 | — | Y171 (78.6) | Y203 (92.8) | S233 (61.1%) | — | S357 (100) | T416 (100) | T455 (88.0) | Y520 (88.9) | 56.9 | SEQ ID NO: 84 |
| Solanum tuberosum L. HMG1 | T77 (85.7) | Y238 (92.8) | Y270 (100) | S300 (77.8) | — | S424 (100) | T483 (92.8) | T522 (96.0) | Y587 (88.9) | 68.4 | SEQ ID NO: 85 |
| Solanum tuberosum L. HMG2 | T86 (100) | Y238 (92.8) | — | — | — | S424 (100) | T483 (92.8) | T522 (100) | Y587 (88.9) | 66.3 | SEQ ID NO: 86 |
| Solanum tuberosum L. HMG3 | — | Y216 (100) | — | S278 (72.2%) | — | S402 (100) | T461 (85.7) | T500 (100) | Y565 (88.9) | 69.0 | SEQ ID NO: 87 |
| Solanum lycopersicum HMG2 | T89 (100) | Y241 (92.8) | — | — | — | S427 (100) | T486 (92.8) | T525 (100) | Y590 (88.9) | 67.0 | SEQ ID NO: 88 |
| Medicago polymorpha HMG4 | T67 (85.7) | Y184 (92.8) | Y216 (92.8) | — | — | S370 (100) | T429 (92.8) | T468 (100) | Y533 (88.9) | 68.6 | SEQ ID NO: 89 |
| Medicago polymorpha HMG5 | T81 (100) | Y222 (92.8) | Y254 (92.8) | S284 (77.8%) | S336 (100) | S408 (100) | T467 (100) | T506 (100) | Y571 (100) | 64.7 | SEQ ID NO: 90 |

In Table 1, the numbers in parentheses represent the percentages (%) of sequence identity to each conserved region of the HMGR (S type) from *Arabidopsis thaliana* used as a standard. "–" means that the corresponding conserved region or specific amino acid residue is absent.

It can be seen from Table 1 that in other types of HMGR carrying conserved regions corresponding to each of the conserved regions containing the amino acid residues at positions 91, 225, 257, 287, 339, 411, 470, 509 and 574 of the *Arabidopsis thaliana* HMGR (HMG1S) shown by SEQ ID NO:1, amino acid residues corresponding to the foregoing amino acid residues are present.

It is also demonstrated that when at least one amino acid residue selected from the group consisting of the amino acid residues at positions 225, 257, 287, 411, 470, 509 and 574 of the *Arabidopsis thaliana* HMGR shown by SEQ ID NO:1 was replaced with alanine or phenylalanine, the enzyme activity was reduced in comparison with the wild type but was relatively maintained. This infers that it is possible to prevent phosphorylation in vivo, and therefore to prevent the suppression of enzyme activity due to phosphorylation of those sites, so that stable enzyme activity can be retained.

Next, it is demonstrated that enzyme activity was increased when at least one amino acid residue selected from

TABLE 2

| | Comparative Example | Example | | | | | | | | | | | | | | |
|---|---|---|---|---|---|---|---|---|---|---|---|---|---|---|---|---|
| | 1 | 1 | 2 | 3 | 4 | 5 | 6 | 7 | 8 | 9 | 10 | 11 | 12 | 13 | 14 | 15 |
| Mutation site | None | Y225 | | | Y257 | | | S411 | | | T470 | | | T509 | | |
| Mutated amino acid | Wild-type | F | D | E | F | D | E | A | D | E | A | D | E | A | D | E |
| Specific activity | 1 | 0.57 | — | — | 0.67 | — | 0.05 | 0.85 | — | 0.07 | 0.53 | — | 0.10 | 0.72 | 0.25 | — |

| | Example | | | | | | | | | | | | | Reference Example | | |
|---|---|---|---|---|---|---|---|---|---|---|---|---|---|---|---|---|
| | 16 | 17 | 18 | 19 | 20 | 21 | 22 | 23 | 24 | 25 | 26 | 27 | 28 | 1 | 2 | 3 |
| Mutation site | T91 | | | S339 | | | S287 | | | Y574 | | | | S577 | | |
| Mutated amino acid | A | D | E | A | D | E | A | D | E | A | F | D | E | A | D | E |
| Specific activity | 1.02 | 1.48 | 1.42 | 1.25 | 1.61 | 1.47 | 0.89 | — | — | 0.72 | 0.81 | 0.02 | 0.01 | 1.41 | 0.15 | 0.01 |

In Table 2, "–" means that enzyme activity is eliminated, while a score of 1 or more means that enzyme activity is higher than in the wild type.

From the results in Table 2, it is first demonstrated that enzyme activity was reduced or eliminated when at least one amino acid residue selected from the group consisting of the amino acid residues at positions 225, 257, 287, 411, 470, 509 and 574 of the *Arabidopsis thaliana* HMGR shown by SEQ ID NO:1 was replaced with aspartic acid or glutamic acid.

the group consisting of the amino acid residues at positions 91 and 339 of the *Arabidopsis thaliana* HMGR shown by SEQ ID NO:1 was replaced with aspartic acid or glutamic acid.

It is also demonstrated that when alanine was substituted for the amino acid residue at position 91 and/or 339 of the *Arabidopsis thaliana* HMGR shown by SEQ ID NO:1, the enzyme activity was increased in comparison with wild-type HMGR, but was less than those of the pseudo-phosphorylated mutants. This is evidence that since in the wild type, these amino acid residues are phosphorylated in vivo as necessary, and thus the enzyme activity can be expected to be increased due to phosphorylation, enzyme activity is maintained or suppressed in mutants with an alanine substitution capable of suppressing phosphorylation.

It is shown that when alanine, aspartic acid or glutamic acid was substituted for the amino acid residue at position 48 of the *Arabidopsis thaliana* HMGR shown by SEQ ID NO:1, however, the enzyme activity did not differ from that of the wild type, and thus the HMGR enzyme activity was not controllable.

These results demonstrate that HMGR enzyme activity can be controlled by deleting, or replacing with another amino acid residue, at least one amino acid residue selected from the group consisting of the amino acid residues at positions 91, 225, 257, 287, 339, 411, 470, 509 and 574 of the *Arabidopsis thaliana* HMGR shown by SEQ ID NO:1.

The results of Tables 1 and 2 are also evidence that HMGR enzyme activity can be controlled by deleting, or replacing with another amino acid residue, at least one amino acid residue selected from the group consisting of amino acid residues at positions corresponding to positions 91, 225, 257, 287, 339, 411, 470, 509 and 574 of the *Arabidopsis thaliana* HMGR shown by SEQ ID NO:1.

This is also evidence that mevalonic acid yield and therefore isoprenoid and polyisoprenoid yields are also controlled in transformants expressing a mutant protein in which at least one amino acid residue selected from the group consisting of amino acid residues at positions corresponding to positions 91, 225, 257, 287, 339, 411, 470, 509 and 574 of the *Arabidopsis thaliana* HMGR shown by SEQ ID NO:1 is deleted or replaced with another amino acid residue.

(Construction of HbHMGR Expression Vector)

The sequence of SEQ ID NO:105, which is a DNA sequence of the *Hevea brasiliensis*-derived HMG1 shown by SEQ ID NO:10 (hereunder also referred to as HbHMG1) was amplified by PCR using the primers shown below. The resulting PCR product was cloned to pENTR/D-TOPO by the heat shock method using *E. coli* to obtain an entry vector called pENTR/HbHMG1. The entry vector was prepared with a pENTR Directional TOPO Cloning Kit using DH5α as the *E. coli*.

```
(Primer 69: SEQ ID NO: 106)
5'-CACCATGGACACCACCGGCCGGCTCCACCAC-3'

(Primer 70: SEQ ID NO: 107)
5'-CGCCTCGAGTCAAGATGCAGCTTTAGACAT-3'
```

(Preparation of Expression Vector (Recombinant Vector))

Using the pENTR/HbHMG1, the gene sequence part of the target protein was recombined and transfected into pET160-DEST to obtain an expression vector pDEST-HbHMG1. LR reaction of Gateway system (Invitrogen) was used for the recombination reaction.

(Preparation of Mutant HbHMGR Expression Vector)

A PCR reaction was performed with PrimeSTAR HS (Takara) using the pDEST/HbHMG1 as a template. The composition per sample (25 μl) of the PCR reaction solution was 1 to 5 ng of plasmid, 0.75 μl of each of the forward and reverse primers (each 10 pmol/μl) shown below for each mutation, 5 μl of 5× buffer for primestar (Mg$^{2+}$), 2 μl of dNTPmix, 0.25 μl of primestar HS, and 15.75 μl of milliQ water. The PCR was carried out using the following predetermined reaction cycle: step 1: 2 minutes at 98° C., step 2: 10 seconds at 98° C., step 3: 15 seconds at 60° C., step 4: 8 minutes at 68° C., steps 2 to 4 repeated 17 times. A part of the PCR product (7 μl) was electrophoresed, and when amplification was observed, 0.2 μl of DpnI was added to the remainder of the PCR product and reacted for 3 hours at 37° C. 2 μl of the reaction solution was added to 20 μl of self-made *E. coli* (DH5α) chemically competent cells, and the cells were transformed by the heat shock method. All of the bacterial culture was inoculated on LB agar medium containing 50 μg/ml ampicillin, and cultured overnight at 37° C. After culture, the resulting colonies were screened by colony PCR. Plasmid extraction was performed with a Plasmid mini kit (Qiagen), and insertion of the mutation was verified by sequencing, to obtain a desired mutant HbHMG1 expression vector. A total of 21 types of mutant HbHMG1 expression vectors were prepared by this method. A serine-566 (corresponding to serine 577 of HMG1S from *Arabidopsis thaliana*) mutant HbHMG1 as a positive control was also included. The sequence verification was carried out with a BigDye Terminator Cycle Sequencing V3.0 Ready Reaction Kit (Applied Biosystems) using an ABI3130XI sequencer.

The primers used in preparing each mutant HbHMG1 are shown below.

<Primers Used to Mutate Tyrosine 214 of HbHMG1>
(Primers Used for pHbHMG1/Y214F)

```
(Primer 71 (forward): SEQ ID NO: 108)
5'-gtagaagggttcgatTTCgagtcgattttaggac-3'

(Primer 72 (reverse): SEQ ID NO: 109)
5'-gtcctaaaatcgactcGAAatcgaacccttctac-3'
```

(Primers Used for pHbHMG1/Y214E)

```
(Primer 73 (forward): SEQ ID NO: 110)
5'-gtagaagggttcgatGAAgagtcgattttaggaca-3'

(Primer 74 (reverse): SEQ ID NO: 111)
5'-tgtcctaaaatcgactcTTCatcgaacccttctac-3'
```

<Primers Used to Mutate Tyrosine 246 of HbHMG1>
(Primers Used for pHbHMG1/Y246F)

```
(Primer 75 (forward): SEQ ID NO: 112)
5'-gctgaacgggcgggagTTCtctgttccaatggc-3'

(Primer 76 (reverse): SEQ ID NO: 113)
5'-gccattggaacagaGAActcccgcccgttcagc-3'
```

(Primers Used for pHbHMG1/Y246E)

```
(Primer 77 (forward): SEQ ID NO: 114)
5'-gctgaacgggcgggagGAAtctgttccaatggc-3'

(Primer 78 (reverse): SEQ ID NO: 115)
5'-gccattggaacagaTTCctcccgcccgttcagc-3'
```

<Primers Used to Mutate Serine 400 of HbHMG1>
(Primers Used for pHbHMG1/S400A)

```
(Primer 79 (forward): SEQ ID NO: 116)
5'-gaaggacgtggcaaaGCCgttgtttgtgag-3'

(Primer 80 (reverse): SEQ ID NO: 117)
5'-ctcacaaacaacGGCtttgccacgtccttc-3'
```

(Primers Used for pHbHMG1/S400D)

(Primer 81 (forward): SEQ ID NO: 118)
5'-tgaaggacgtggcaaaGACgttgtttgtgaggcaattatcaag-3'

(Primer 82 (reverse): SEQ ID NO: 119)
5'-cttgataattgcctcacaaacaacGTCtttgccacgtccttca-3'

(Primers Used for pHbHMG1/S400E)

(Primer 83 (forward): SEQ ID NO: 120)
5'-tgaaggacgtggcaaaGAAgttgtttgtgaggcaattatcaag-3'

(Primer 84 (reverse): SEQ ID NO: 121)
5'-cttgataattgcctcacaaacaacTTCtttgccacgtccttca-3'

<Primers Used to Mutate Threonine 459 of HbHMG1>
(Primers Used for pHbHMG1/T459C)

(Primer 85 (forward): SEQ ID NO: 122)
5'-ctgcaatctttattgccTGTggccaggatccagc-3'

(Primer 86 (reverse): SEQ ID NO: 123)
5'-gctggatcctggccACAggcaataaagattgcag-3'

(Primers Used for pHbHMG1/T459D)

(Primer 87 (forward): SEQ ID NO: 124)
5'-tcgtatctgcaatctttattgccGATggccaggatccagcacaga-3'

(Primer 88 (reverse): SEQ ID NO: 125)
5'-tatgtgctggatcctggccATCggcaataaagattgcagatacga-3'

(Primers Used for pHbHMG1/T459E)

(Primer 89 (forward): SEQ ID NO: 126)
5'-tcgtatctgcaatctttattgccGAAggccaggatccagcacaga-3'

(Primer 90 (reverse): SEQ ID NO: 127)
5'-tctgtgctggatcctggccTTCggcaataaagattgcagatacga-3'

<Primers Used to Mutate Threonine 498 of HbHMG1>
(Primers Used for pHbHMG1/T498C)

(Primer 91 (forward): SEQ ID NO: 128)
5'-ctccattgaggtgggtTGTgtcggaggtggaactc-3'

(Primer 92 (reverse): SEQ ID NO: 129)
5'-gagttccacctccgacACAacccacctcaatggag-3'

(Primers Used for pHbHMG1/T498D)

(Primer 93 (forward): SEQ ID NO: 130)
5'-accatgccctccattgaggtgggtGACgtcggaggtggaactcaac-3'

(Primer 94 (reverse): SEQ ID NO: 131)
5'-gttgagttccacctccgacGTCacccacctcaatggagggcatggt-3'

(Primers Used for pHbHMG1/T498E)

(Primer 95 (forward): SEQ ID NO: 132)
5'-accatgccatccattgaggtgggtGAAgtcggaggtggaactcaac-3'

(Primer 96 (reverse): SEQ ID NO: 133)
5'-gttgagttccacctccgacTTCacccacctcaatggagggcatggt-3'

<Primers Used to Mutate Serine 566 of HbHMG1>
(Primers Used for pHbHMG1/S566A)

(Primer 97 (forward): SEQ ID NO: 134)
5'-gtcacatgaagtacaacagaGCCagcaaagatatgtctaaagct-3'

(Primer 98 (reverse): SEQ ID NO: 135)
5'-agctttagacatatctttgctGGCtctgttgtacttcatgtgact-3'

(Primers Used for pHbHMG1/S566D)

(Primer 99 (forward): SEQ ID NO: 136)
5'-gtcacatgaagtacaacagaGACagcaaagatatgtctaaagct-3'

(Primer 100 (reverse): SEQ ID NO: 137)
5'-agctttagacatatctttgctGTCtctgttgtacttcatgtgact-3'

<Primers Used to Mutate Serine 276 of HbHMG1>
(Primers Used for pHbHMG1/S276A)

(Primer 101 (forward): SEQ ID NO: 138)
5'-cttgtcaggtggggccaccGCCgtcttgttgaaggatggcatgac-3'

(Primer 102 (reverse): SEQ ID NO: 139)
5'-gtcatgccatccttcaacaagacGGCggtggcccacctgacaag-3'

(Primers Used for pHbHMG1/S276D)

(Primer 103 (forward): SEQ ID NO: 140)
5'-caggtggggccaccGACgtcttgttgaagg-3'

(Primer 104 (reverse): SEQ ID NO: 141)
5'-ccttcaacaagacGTCggtggcccacctg-3'

(Primers Used for pHbHMG1/S276E)

(Primer 105 (forward): SEQ ID NO: 142)
5'-cttgtcaggtggggccaccGAAgtcttgttgaaggatggcatgac-3'

(Primer 106 (reverse): SEQ ID NO: 143)
5'-gtcatgccatccttcaacaagacTTCggtggcccacctgacaag-3'

<Primers Used to Mutate Tyrosine 563 of HbHMG1>
(Primers Used for pHbHMG1/Y563F)

```
(Primer 107 (forward): SEQ ID NO: 144)
5'-gtcaagagtcacatgaagTTCaacagatccagc-3'

(Primer 108 (reverse): SEQ ID NO: 145)
5'-gctggatctgttGAActtcatgtgactcttgac-3'
```

(Primers Used for pHbHMG1/Y563D)

```
(Primer 109 (forward): SEQ ID NO: 146)
5'-gtcaagagtcacatgaagGACaacagatccagc-3'

(Primer 110 (reverse): SEQ ID NO: 147)
5'-gctggatctgttGTCcttcatgtgactcttgac-3'
```

(Primers Used for pHbHMG1/Y563E)

```
(Primer 111 (forward): SEQ ID NO: 148)
5'-gtcaagagtcacatgaagGAAacagatccagc-3'

(Primer 112 (reverse): SEQ ID NO: 149)
5'-gctggatctgttTTCcttcatgtgactcttgac-3'
```

(Preparation of Transformant Expressing Mutant HbHMGR)

E. coli was transformed by the heat shock method using each of the mutant HbHMG1 expression vectors obtained above, to obtain transformants expressing each mutant HbHMG1. BL21 Star (DE3) was used as the E. coli.

(Expression of Mutant HbHMGR)

Each of the E. coli transformants expressing each mutant HbHMG1 obtained above was cultured overnight at 37° C. in 2 ml of LB liquid medium, and the bacterial culture after culture was transferred to 50 ml of LB liquid medium and then shake-cultured for 2 hours at 37° C., after which IPTG was added to a final concentration of 0.5 mM, and the cells were cultured for 6 hours at 20° C. Ampicillin was added to all the LB liquid media to a concentration of 50 µg/ml. The entire amount of each bacterial culture after completion of all culture steps was centrifuged for 5 minutes at 4° C. and 5000 g to collect the cells, and the pellets were stored at −20° C.

(Collection and Purification of Mutant HbHMGR)

Each of the bacterial cell samples obtained above was dissolved in binding buffer (40 mM sodium phosphate (pH 8.0), 1 mM EDTA, 300 mM sodium chloride, 0.1% TritonX-100, 10% glycerol, 0.8 mM imidazole) supplemented with 100 µM AEBSF, 10 µM Leupeptin, 10 mM DTT and 0.1% lysozyme. The bacterial cells were disrupted (disruption conditions: Duty cycle 50%, Output control 2.5, 1 minute×3) with a Sonifier 450 sonicator (Branson) while being cooled on ice. These were then centrifuged for 15 minutes at 4° C. and 15,000 rpm, and 100 µl of Ni-NTA Agarose (Qiagen) that had been washed three times in advance with binding buffer was added to the supernatant. The mixture was rotary shaken for 1 hour at 4° C. and then centrifuged for 5 minutes at 4° C. and 8000 rpm. The resin was transferred to an empty column (Bio-Rad) and washed three times with washing buffer (20 mM imidazole, other components as in binding buffer). 15 µl of elution buffer (430 mM imidazole, other components as in binding buffer) supplemented with 100 µM AEBSF, 10 µM Leupeptin and 10 mM DTT was added to the resin, which was then eluted by 1 minute of centrifugation at 4° C. and 15,000 rpm. An additional 20 µl of elution buffer was added to the resin, which was then eluted by 1 minute of centrifugation at 4° C. and 15,000 rpm. A total of 35 µl of His-tag purified mutant HbHMG1 protein solution was obtained.

The quantity and purity of each resulting protein were verified by polyacrylamide gel electrophoresis (SDS-PAGE). For quantification, BSA standard solutions (100 ng, 300 ng, 1 µg) were electrophoresed at the same time, and band strength was detected and determined from the gel after CBB staining using Gel Doc XR+ and Image Lab.

(Determination of Enzyme Activity of Mutant HbHMGR)

1.65 ng of each of the HbHMG1 mutants obtained after purification was added to a reaction solution (1 mM NADPH, 0.4 mg/ml BSA, 40 mM sodium phosphate (pH 8.0), 1 mM EDTA, 50 mM sodium chloride, 1% TritonX-100, 10% glycerol, 4 mM DTT), and pre-incubated for 5 minutes at 37° C., after which 20 µM HMG-CoA (Perkin Elmer) labeled with $^{14}$C was added (final reaction solution volume 26 µl), and the mixture was reacted for 15 minutes at 37° C. 5 µl of 1 mg/ml mevalonic lactone and 5 µl of 6N hydrochloric acid were added, and the mixture was left for 15 minutes at room temperature and then neutralized by addition of 125 µl of saturated potassium phosphate buffer at pH 6.0. 300 µl of ethyl acetate was added and mixed vigorously, and the mixture was centrifuged for 5 minutes at 20° C. and 15,000 rpm. The ethyl acetate layer of the supernatant was analyzed for radioactivity in a liquid scintillation counter. The enzyme activity results for each mutant HbHMG1 are shown in Table 3. The enzyme activities are expressed as specific activity, with wild-type HbHMG1 set equal to 1.

TABLE 3

|  | Comparative Example | Example | | | | | | | | | |
|---|---|---|---|---|---|---|---|---|---|---|---|
|  | 1 | 1 | 2 | 3 | 4 | 5 | 6 | 7 | 8 | 9 | 10 |
| Mutation site | None | Y214 | | Y246 | | S400 | | | T459 | | |
| Mutated amino acid | Wild-type | F | E | F | E | A | D | E | C | D | E |
| Specific activity | 1 | 0.99 | — | 1.03 | 0.09 | 0.56 | 0.05 | 0.18 | 0.60 | — | — |

|  | Example | | | | | | | | | Reference Example | |
|---|---|---|---|---|---|---|---|---|---|---|---|
|  | 11 | 12 | 13 | 14 | 15 | 16 | 17 | 18 | 19 | 1 | 2 |
| Mutation site | T498 | | | S276 | | | Y563 | | | S566 | |
| Mutated amino acid | C | D | E | A | D | E | F | D | E | A | D |
| Specific activity | 0.76 | — | — | 0.74 | 0.09 | 0.39 | 0.68 | — | — | 1.15 | 0.66 |

In Table 3, "−" means that enzyme activity is eliminated, while a score of 1 or more means that enzyme activity is higher than in the wild type.

From the results of Table 3, it is first demonstrated that enzyme activity was reduced or eliminated when at least one amino acid residue selected from the group consisting of the amino acid residues at positions 214, 246, 276, 400, 459, 498 and 563 of the *Hevea brasiliensis* HMG1 shown by SEQ ID NO:10 was replaced with aspartic acid or glutamic acid.

It is also demonstrated that when at least one amino acid residue selected from the amino acid residues at positions 214, 246, 276, 400, 459, 498 and 563 of the *Hevea brasiliensis* HMG1 shown by SEQ ID NO:10 was replaced with alanine, phenylalanine or cysteine, the enzyme activity was comparable with or less than that of the wild type but was relatively maintained. This infers that it is possible to prevent phosphorylation in vivo, and therefore to prevent the suppression of enzyme activity due to phosphorylation of those sites, so that stable enzyme activity can be retained.

Sequence Listing Free Text

SEQ ID NO:1: Amino acid sequence of HMGR (S type) from *Arabidopsis thaliana*
SEQ ID NO:2: Amino acid sequence of conserved region containing position 48 amino acid residue in *Arabidopsis thaliana* of SEQ ID NO:1
SEQ ID NO:3: Amino acid sequence of conserved region containing position 91 amino acid residue in *Arabidopsis thaliana* of SEQ ID NO:1
SEQ ID NO:4: Amino acid sequence of conserved region containing position 225 amino acid residue in *Arabidopsis thaliana* of SEQ ID NO:1
SEQ ID NO:5: Amino acid sequence of conserved region containing position 257 amino acid residue in *Arabidopsis thaliana* of SEQ ID NO:1
SEQ ID NO:6: Amino acid sequence of conserved region containing position 339 amino acid residue in *Arabidopsis thaliana* of SEQ ID NO:1
SEQ ID NO:7: Amino acid sequence of conserved region containing position 411 amino acid residue in *Arabidopsis thaliana* of SEQ ID NO:1
SEQ ID NO:8: Amino acid sequence of conserved region containing position 470 amino acid residue in *Arabidopsis thaliana* of SEQ ID NO:1
SEQ ID NO:9: Amino acid sequence of conserved region containing position 509 amino acid residue in *Arabidopsis thaliana* of SEQ ID NO:1
SEQ ID NO:10: Amino acid sequence of HMG1 from *Hevea brasiliensis*
SEQ ID NO:11: Amino acid sequence of HMGR from *Taraxacum koksaghys*
SEQ ID NO:12: Nucleotide sequence of gene coding for HMGR (S type) from *Arabidopsis thaliana*
SEQ ID NO:13: Primer 1
SEQ ID NO:14: Primer 2
SEQ ID NO:15: Primer 3
SEQ ID NO:16: Primer 4
SEQ ID NO:17: Primer 5
SEQ ID NO:18: Primer 6
SEQ ID NO:19: Primer 7
SEQ ID NO:20: Primer 8
SEQ ID NO:21: Primer 9
SEQ ID NO:22: Primer 10
SEQ ID NO:23: Primer 11
SEQ ID NO:24: Primer 12
SEQ ID NO:25: Primer 13
SEQ ID NO:26: Primer 14
SEQ ID NO:27: Primer 15
SEQ ID NO:28: Primer 16
SEQ ID NO:29: Primer 17
SEQ ID NO:30: Primer 18
SEQ ID NO:31: Primer 19
SEQ ID NO:32: Primer 20
SEQ ID NO:33: Primer 21
SEQ ID NO:34: Primer 22
SEQ ID NO:35: Primer 23
SEQ ID NO:36: Primer 24
SEQ ID NO:37: Primer 25
SEQ ID NO:38: Primer 26
SEQ ID NO:39: Primer 27
SEQ ID NO:40: Primer 28
SEQ ID NO:41: Primer 29
SEQ ID NO:42: Primer 30
SEQ ID NO:43: Primer 31
SEQ ID NO:44: Primer 32
SEQ ID NO:45: Primer 33
SEQ ID NO:46: Primer 34
SEQ ID NO:47: Primer 35
SEQ ID NO:48: Primer 36
SEQ ID NO:49: Primer 37
SEQ ID NO:50: Primer 38
SEQ ID NO:51: Primer 39
SEQ ID NO:52: Primer 40
SEQ ID NO:53: Primer 41
SEQ ID NO:54: Primer 42
SEQ ID NO:55: Primer 43
SEQ ID NO:56: Primer 44
SEQ ID NO:57: Primer 45
SEQ ID NO:58: Primer 46
SEQ ID NO:59: Primer 47
SEQ ID NO:60: Primer 48
SEQ ID NO:61: Primer 49
SEQ ID NO:62: Primer 50
SEQ ID NO:63: Primer 51
SEQ ID NO:64: Primer 52
SEQ ID NO:65: Primer 53
SEQ ID NO:66: Primer 54
SEQ ID NO:67: Primer 55
SEQ ID NO:68: Primer 56
SEQ ID NO:69: Amino acid sequence of HMG2 from *Arabidopsis thaliana*
SEQ ID NO:70: Amino acid sequence of HMG2 from *Hevea brasiliensis*
SEQ ID NO:71: Amino acid sequence of HMG3 from *Hevea brasiliensis*
SEQ ID NO:72: Amino acid sequence of HMG4 from *Hevea brasiliensis*
SEQ ID NO:73: Amino acid sequence of HMG5 from *Hevea brasiliensis*
SEQ ID NO:74: Amino acid sequence of HMGR (TC18019) from *Lactuca sativa* Lettuce
SEQ ID NO:75: Amino acid sequence of HMGR (TC23858) from *Lactuca sativa* Lettuce
SEQ ID NO:76: Amino acid sequence of HMGR (TC19509) from *Lactuca sativa* Lettuce
SEQ ID NO:77: Amino acid sequence of HMGR (TC22046) from *Lactuca sativa* Lettuce
SEQ ID NO:78: Amino acid sequence of HMGR (TC22228) from *Lactuca sativa* Lettuce
SEQ ID NO:79: Amino acid sequence of HMGR (TC23348) from *Lactuca sativa* Lettuce
SEQ ID NO:80: Amino acid sequence of HMGR (003982m) from *Manihot esculenta*
SEQ ID NO:81: Amino acid sequence of HMGR (004209m) from *Manihot esculenta*

SEQ ID NO:82: Amino acid sequence of HMGR from *Eucommia ulmondes*
SEQ ID NO:83: Amino acid sequence of HMGR from *Euphorbia helioscopia* L.
SEQ ID NO:84: Amino acid sequence of HMG1 from *Oryza sativa*
SEQ ID NO:85: Amino acid sequence of HMG1 from *Solanum tuberosum* L.
SEQ ID NO:86: Amino acid sequence of HMG2 from *Solanum tuberosum* L.
SEQ ID NO:87: Amino acid sequence of HMG3 from *Solanum tuberosum* L.
SEQ ID NO:88: Amino acid sequence of HMG2 from *Solanum lycopersicum*
SEQ ID NO:89: Amino acid sequence of HMG4 from *Medicago polymorpha*
SEQ ID NO:90: Amino acid sequence of HMG5 from *Medicago polymorpha*
SEQ ID NO:91: Amino acid sequence of conserved region containing position 287 amino acid residue in *Arabidopsis thaliana* of SEQ ID NO:1
SEQ ID NO:92: Amino acid sequence of conserved region containing position 574 amino acid residue in *Arabidopsis thaliana* of SEQ ID NO:1
SEQ ID NO:93: Primer 57
SEQ ID NO:94: Primer 58
SEQ ID NO:95: Primer 59
SEQ ID NO:96: Primer 60
SEQ ID NO:97: Primer 61
SEQ ID NO:98: Primer 62
SEQ ID NO:99: Primer 63
SEQ ID NO:100: Primer 64
SEQ ID NO:101: Primer 65
SEQ ID NO:102: Primer 66
SEQ ID NO:103: Primer 67
SEQ ID NO:104: Primer 68
SEQ ID NO:105: Nucleotide sequence of gene coding for HMG1 from *Hevea brasiliensis*
SEQ ID NO:106: Primer 69
SEQ ID NO:107: Primer 70
SEQ ID NO:108: Primer 71
SEQ ID NO:109: Primer 72
SEQ ID NO:110: Primer 73
SEQ ID NO:111: Primer 74
SEQ ID NO:112: Primer 75
SEQ ID NO:113: Primer 76
SEQ ID NO:114: Primer 77
SEQ ID NO:115: Primer 78
SEQ ID NO:116: Primer 79
SEQ ID NO:117: Primer 80
SEQ ID NO:118: Primer 81
SEQ ID NO:119: Primer 82
SEQ ID NO:120: Primer 83
SEQ ID NO:121: Primer 84
SEQ ID NO:122: Primer 85
SEQ ID NO:123: Primer 86
SEQ ID NO:124: Primer 87
SEQ ID NO:125: Primer 88
SEQ ID NO:126: Primer 89
SEQ ID NO:127: Primer 90
SEQ ID NO:128: Primer 91
SEQ ID NO:129: Primer 92
SEQ ID NO:130: Primer 93
SEQ ID NO:131: Primer 94
SEQ ID NO:132: Primer 95
SEQ ID NO:133: Primer 96
SEQ ID NO:134: Primer 97
SEQ ID NO:135: Primer 98
SEQ ID NO:136: Primer 99
SEQ ID NO:137: Primer 100
SEQ ID NO:138: Primer 101
SEQ ID NO:139: Primer 102
SEQ ID NO:140: Primer 103
SEQ ID NO:141: Primer 104
SEQ ID NO:142: Primer 105
SEQ ID NO:143: Primer 106
SEQ ID NO:144: Primer 107
SEQ ID NO:145: Primer 108
SEQ ID NO:146: Primer 109
SEQ ID NO:147: Primer 110
SEQ ID NO:148: Primer 111
SEQ ID NO:149: Primer 112
SEQ ID NO:150: Primer 113
SEQ ID NO:151: Primer 114

The invention claimed is:

1. A recombinant vector, carrying the gene which codes for a mutant protein,
wherein the mutant protein is a 3-hydroxy-3-methylglutaryl CoA reductase,
wherein, in the mutant protein, at least one amino acid residue selected from the group consisting of amino acid residues at positions corresponding to the positions 91, 225, 257, 287, 339, 411, 470, 509 and 574 of the *Arabidopsis thaliana* 3-hydroxy-3-methylglutaryl CoA reductase shown by SEQ ID NO: 1 is deleted or replaced with another amino acid residue as follows;
the amino acid residue at position corresponding to position 91 of SEQ ID NO:1 is deleted or replaced with alanine, phenylalanine, or cysteine, and/or
at least one amino acid residue selected from the group consisting of the amino acid residues at position corresponding to position 225, position 257 of SEQ ID NO:1 is deleted or replaced with alanine, cysteine, aspartic acid or glutamic acid and/or
the amino acid residue at position corresponding to position 287 of SEQ ID NO: 1 is deleted or replaced with alanine, phenylalanine, aspartic acid or glutamic acid and/or
the amino acid residue at position corresponding to position 339 of SEQ ID NO:1 is deleted or replaced with alanine, phenylalanine, cysteine or aspartic acid and/or
at least one amino acid residue selected from the group consisting of, amino acid residues at positions corresponding to positions 411, 470, 509, and 574 of SEQ ID NO:1, is deleted or replaced with alanine, phenylalanine, cysteine, aspartic acid or glutamic acid.

2. A recombinant vector comprising a gene encoding a mutant 3-hydroxy-3-methylglutaryl CoA reductase protein, wherein the mutant protein is a mutant protein in which the amino acid residue at position corresponding to position 91 of SEQ ID NO: 1 is replaced with glutamic acid and
the amino acid residue at position corresponding to position 339 of SEQ ID NO: 1 is replaced with aspartic acid.

3. The recombinant vector according to claim 1, wherein the mutant protein is a mutant protein in which at least one amino acid residue selected from the group consisting of the amino acid residues at positions corresponding to positions 225, and 257 of SEQ ID NO:1, is deleted or replaced with alanine or cysteine and/or
at least one amino acid residue selected from the group consisting of the amino acid residues at positions corresponding to positions 411, 470, 509, and 574 of SEQ ID NO:1, is deleted or replaced with alanine, phenylamine or cysteine, and/or the amino acid residue at position corresponding to position 287 of SEQ ID NO:1 is deleted or replaced with alanine or phenylalanine.

4. The recombinant vector according to claim 1, wherein the mutant protein is a mutant protein in which at least one amino acid residue selected from the group consisting of the amino acid residues at positions corresponding to positions 91, and 339 of SEQ NO:1 is deleted or replaced with alanine or phenylalanine.

5. The recombinant vector according to claim 1, wherein the mutant protein is a mutant protein in which at least one amino acid residue selected from the group consisting of the amino acid residues at positions corresponding to the positions 225, 257, 287, 411, 470, 509 and 574 of SEQ ID NO:1 is replaced with aspartic acid or glutamic acid.

6. A method for controlling isoprenoid yield comprising a step of introducing the recombinant vector according to claim 1 into a host.

7. A method for controlling mevalonic acid yield comprising a step of introducing the recombinant vector according to claim 1 into a host.

8. A plant comprising the recombinant vector according to claim 1.

9. A method for controlling isoprenoid yield in a plant comprising cultivating the plant according to claim 8.

10. A method for controlling mevalonic acid yield in a plant comprising cultivating the plant according to claim 8.

11. An isoprenoid-producing plant comprising the recombinant vector according to claim 1.

12. A method for controlling isoprenoid yield in a plant comprising cultivating the isoprenoid-producing plant according to claim 11.

13. A method for controlling mevalonic acid yield in a plant comprising cultivating the isoprenoid-producing plant according to claim 11.

14. A recombinant vector, carrying the gene which codes for a mutant 3-hydroxy-3-methylglutaryl CoA reductase comprising at least one amino acid residue selected from the group consisting of amino acid residues at positions corresponding to positions 70, 214, 246, 276, 400, 459, 498 and 563 of the *Hevea brasiliensis* 3-hydroxy-3-methylglutaryl CoA reductase shown by SEQ ID NO:10, deleted or replaced with another amino acid residue as follows:

the amino acid residue at position corresponding to the amino acid residue at position 70 of SEQ ID NO:10 is deleted or replaced with alanine, phenylalanine, or cysteine and/or at least one amino acid residue selected from the group consisting of the amino acid residues at positions corresponding to positions 214, and 246 of SEQ ID NO:10 is deleted or replaced with alanine, cysteine, aspartic acid or glutamic acid and/or at least one amino acid residue selected from the group consisting of the amino acid residues at positions corresponding to positions 276, 400, 459, 498 and 563 of SEQ ID NO:10 is deleted or replaced with alanine, phenylalanine, cysteine, aspartic acid or glutamic acid.

* * * * *

SEQUENCE LISTING

```
<160> NUMBER OF SEQ ID NOS: 151

<210> SEQ ID NO 1
<211> LENGTH: 592
<212> TYPE: PRT
<213> ORGANISM: Arabidopsis thaliana

<400> SEQUENCE: 1

Met Asp Leu Arg Arg Arg Pro Pro Lys Pro Pro Val Thr Asn Asn Asn
1               5                   10                  15

Asn Ser Asn Gly Ser Phe Arg Ser Tyr Gln Pro Arg Thr Ser Asp Asp
            20                  25                  30

Asp His Arg Arg Arg Ala Thr Thr Ile Ala Pro Pro Lys Ala Ser
        35                  40                  45

Asp Ala Leu Pro Leu Pro Leu Tyr Leu Thr Asn Ala Val Phe Phe Thr
    50                  55                  60

Leu Phe Phe Ser Val Ala Tyr Tyr Leu Leu His Arg Trp Arg Asp Lys
65                  70                  75                  80

Ile Arg Tyr Asn Thr Pro Leu His Val Val Thr Ile Thr Glu Leu Gly
```

```
                    85                  90                  95
Ala Ile Ile Ala Leu Ile Ala Ser Phe Ile Tyr Leu Leu Gly Phe Phe
                100                 105                 110

Gly Ile Asp Phe Val Gln Ser Phe Ile Ser Arg Ala Ser Gly Asp Ala
                115                 120                 125

Trp Asp Leu Ala Asp Thr Ile Asp Asp Asp His Arg Leu Val Thr
130                 135                 140

Cys Ser Pro Pro Thr Pro Ile Val Ser Val Ala Lys Leu Pro Asn Pro
145                 150                 155                 160

Glu Pro Ile Val Thr Glu Ser Leu Pro Glu Glu Asp Glu Glu Ile Val
                165                 170                 175

Lys Ser Val Ile Asp Gly Val Ile Pro Ser Tyr Ser Leu Glu Ser Arg
                180                 185                 190

Leu Gly Asp Cys Lys Arg Ala Ala Ser Ile Arg Arg Glu Ala Leu Gln
                195                 200                 205

Arg Val Thr Gly Arg Ser Ile Glu Gly Leu Pro Leu Asp Gly Phe Asp
                210                 215                 220

Tyr Glu Ser Ile Leu Gly Gln Cys Cys Glu Met Pro Val Gly Tyr Ile
225                 230                 235                 240

Gln Ile Pro Val Gly Ile Ala Gly Pro Leu Leu Leu Asp Gly Tyr Glu
                245                 250                 255

Tyr Ser Val Pro Met Ala Thr Thr Glu Gly Cys Leu Val Ala Ser Thr
                260                 265                 270

Asn Arg Gly Cys Lys Ala Met Phe Ile Ser Gly Gly Ala Thr Ser Thr
                275                 280                 285

Val Leu Lys Asp Gly Met Thr Arg Ala Pro Val Val Arg Phe Ala Ser
290                 295                 300

Ala Arg Arg Ala Ser Glu Leu Lys Phe Phe Leu Glu Asn Pro Glu Asn
305                 310                 315                 320

Phe Asp Thr Leu Ala Val Val Phe Asn Arg Ser Ser Arg Phe Ala Arg
                325                 330                 335

Leu Gln Ser Val Lys Cys Thr Ile Ala Gly Lys Asn Ala Tyr Val Arg
                340                 345                 350

Phe Cys Cys Ser Thr Gly Asp Ala Met Gly Met Asn Met Val Ser Lys
                355                 360                 365

Gly Val Gln Asn Val Leu Glu Tyr Leu Thr Asp Asp Phe Pro Asp Met
                370                 375                 380

Asp Val Ile Gly Ile Ser Gly Asn Phe Cys Ser Asp Lys Lys Pro Ala
385                 390                 395                 400

Ala Val Asn Trp Ile Glu Gly Arg Gly Lys Ser Val Val Cys Glu Ala
                405                 410                 415

Val Ile Arg Gly Glu Ile Val Asn Lys Val Leu Lys Thr Ser Val Ala
                420                 425                 430

Ala Leu Val Glu Leu Asn Met Leu Lys Asn Leu Ala Gly Ser Ala Val
                435                 440                 445

Ala Gly Ser Leu Gly Gly Phe Asn Ala His Ala Ser Asn Ile Val Ser
                450                 455                 460

Ala Val Phe Ile Ala Thr Gly Gln Asp Pro Ala Gln Asn Val Glu Ser
465                 470                 475                 480

Ser Gln Cys Ile Thr Met Met Glu Ala Ile Asn Asp Gly Lys Asp Ile
                485                 490                 495

His Ile Ser Val Thr Met Pro Ser Ile Glu Val Gly Thr Val Gly Gly
                500                 505                 510
```

```
Gly Thr Gln Leu Ala Ser Gln Ser Ala Cys Leu Asn Leu Leu Gly Val
        515                 520                 525

Lys Gly Ala Ser Thr Glu Ser Pro Gly Met Asn Ala Arg Arg Leu Ala
        530                 535                 540

Thr Ile Val Ala Gly Ala Val Leu Ala Gly Glu Leu Ser Leu Met Ser
545                 550                 555                 560

Ala Ile Ala Ala Gly Gln Leu Val Arg Ser His Met Lys Tyr Asn Arg
                565                 570                 575

Ser Ser Arg Asp Ile Ser Gly Ala Thr Thr Thr Thr Thr Thr Thr
            580                 585                 590
```

<210> SEQ ID NO 2
<211> LENGTH: 11
<212> TYPE: PRT
<213> ORGANISM: Arabidopsis thaliana

<400> SEQUENCE: 2

```
Ser Asp Ala Leu Pro Leu Pro Leu Tyr Leu Thr
1               5                   10
```

<210> SEQ ID NO 3
<211> LENGTH: 7
<212> TYPE: PRT
<213> ORGANISM: Arabidopsis thaliana

<400> SEQUENCE: 3

```
Thr Pro Leu His Val Val Thr
1               5
```

<210> SEQ ID NO 4
<211> LENGTH: 14
<212> TYPE: PRT
<213> ORGANISM: Arabidopsis thaliana

<400> SEQUENCE: 4

```
Gly Phe Asp Tyr Glu Ser Ile Leu Gly Gln Cys Cys Glu Met
1               5                   10
```

<210> SEQ ID NO 5
<211> LENGTH: 14
<212> TYPE: PRT
<213> ORGANISM: Arabidopsis thaliana

<400> SEQUENCE: 5

```
Glu Tyr Ser Val Pro Met Ala Thr Thr Glu Gly Cys Leu Val
1               5                   10
```

<210> SEQ ID NO 6
<211> LENGTH: 9
<212> TYPE: PRT
<213> ORGANISM: Arabidopsis thaliana

<400> SEQUENCE: 6

```
Ser Ser Arg Phe Ala Arg Leu Gln Ser
1               5
```

<210> SEQ ID NO 7
<211> LENGTH: 16
<212> TYPE: PRT
<213> ORGANISM: Arabidopsis thaliana

<400> SEQUENCE: 7

```
Ala Val Asn Trp Ile Glu Gly Arg Gly Lys Ser Val Val Cys Glu Ala
1               5                   10                  15
```

<210> SEQ ID NO 8
<211> LENGTH: 14
<212> TYPE: PRT
<213> ORGANISM: Arabidopsis thaliana

<400> SEQUENCE: 8

```
Ile Ala Thr Gly Gln Asp Pro Ala Gln Asn Val Glu Ser Ser
1               5                   10
```

<210> SEQ ID NO 9
<211> LENGTH: 25
<212> TYPE: PRT
<213> ORGANISM: Arabidopsis thaliana

<400> SEQUENCE: 9

```
His Ile Ser Val Thr Met Pro Ser Ile Glu Val Gly Thr Val Gly Gly
1               5                   10                  15

Gly Thr Gln Leu Ala Ser Gln Ser Ala
            20                  25
```

<210> SEQ ID NO 10
<211> LENGTH: 575
<212> TYPE: PRT
<213> ORGANISM: Hevea brasiliensis

<400> SEQUENCE: 10

```
Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
                20                  25                  30

Pro Leu Tyr Leu Thr Asn Ala Val Phe Phe Thr Leu Phe Phe Ser Val
            35                  40                  45

Ala Tyr Tyr Leu Leu His Arg Trp Arg Asp Lys Ile Arg Asn Ser Thr
        50                  55                  60

Pro Leu His Ile Val Thr Leu Ser Glu Ile Val Ala Ile Val Ser Leu
65                  70                  75                  80

Ile Ala Ser Phe Ile Tyr Leu Leu Gly Phe Phe Gly Ile Asp Phe Val
                85                  90                  95

Gln Ser Phe Ile Ala Arg Ala Ser His Asp Val Trp Asp Leu Glu Asp
                100                 105                 110

Thr Asp Pro Asn Tyr Leu Ile Asp Glu Asp His Arg Leu Val Thr Cys
            115                 120                 125

Pro Pro Ala Asn Ile Ser Thr Lys Thr Thr Ile Ile Ala Ala Pro Thr
        130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ile Arg
            180                 185                 190

Arg Glu Ala Leu Gln Arg Met Thr Arg Arg Ser Leu Glu Gly Leu Pro
        195                 200                 205

Val Glu Gly Phe Asp Tyr Glu Ser Ile Leu Gly Gln Cys Cys Glu Met
    210                 215                 220

Pro Val Gly Tyr Val Gln Ile Pro Val Gly Ile Ala Gly Pro Leu Leu
```

```
            225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270

Gly Ala Thr Ser Val Leu Leu Lys Asp Gly Met Thr Arg Ala Pro Val
        275                 280                 285

Val Arg Phe Ala Ser Ala Thr Arg Ala Ala Glu Leu Lys Phe Phe Leu
    290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
                325                 330                 335

Asn Leu Tyr Ile Arg Phe Ser Cys Ser Thr Gly Asp Ala Met Gly Met
            340                 345                 350

Asn Met Val Ser Lys Gly Val Gln Asn Val Leu Glu Phe Leu Gln Ser
        355                 360                 365

Asp Phe Ser Asp Met Asp Val Ile Gly Ile Ser Gly Asn Phe Cys Ser
    370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Val Val Lys Lys Val Leu
                405                 410                 415

Lys Thr Asn Val Ala Ser Leu Val Glu Leu Asn Met Leu Lys Asn Leu
            420                 425                 430

Ala Gly Ser Ala Val Ala Gly Ala Leu Gly Gly Phe Asn Ala His Ala
        435                 440                 445

Gly Asn Ile Val Ser Ala Ile Phe Ile Ala Thr Gly Gln Asp Pro Ala
    450                 455                 460

Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
                485                 490                 495

Gly Thr Val Gly Gly Gly Thr Gln Leu Ala Ser Gln Ser Ala Cys Leu
            500                 505                 510

Asn Leu Leu Gly Val Lys Gly Ala Asn Lys Glu Ser Pro Gly Ser Asn
        515                 520                 525

Ser Arg Leu Leu Ala Ala Ile Val Ala Gly Ser Val Leu Ala Gly Glu
    530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
                565                 570                 575

<210> SEQ ID NO 11
<211> LENGTH: 582
<212> TYPE: PRT
<213> ORGANISM: Taraxacum koksaghys

<400> SEQUENCE: 11

Met Asp Val Gly Arg Arg Ser Ser Leu Lys Pro Ala Ala Thr Lys Gly
1               5                   10                  15

Lys Thr Met Ala Glu Asp Gln Tyr Asp Asp Gln Ile Phe Lys Ala Asp
            20                  25                  30
```

-continued

```
Lys Lys Val Val Asp Ala Val Val Asn Pro Leu Pro Val Gly Ile Ser
             35                  40                  45

Asn Gly Val Phe Phe Thr Val Phe Phe Ser Val Val Tyr Phe Leu Leu
 50                  55                  60

Ile Arg Trp Arg Glu Lys Ile Arg Ser Ser Thr Pro Leu His Val Val
 65                  70                  75                  80

Thr Met Ser Glu Met Ala Ala Ile Phe Phe Phe Val Ala Ser Phe Ile
                 85                  90                  95

Tyr Leu Val Gly Phe Phe Gly Met Ser Phe Val Gln Ala Thr Pro Tyr
                100                 105                 110

Asp Glu Glu Glu Glu Leu Glu Val Asp Glu Thr Glu Ile Val Arg Lys
            115                 120                 125

Glu Asp Thr Arg Val Thr Pro Cys Gly Ala Ala Leu Asp Cys Glu Ser
130                 135                 140

Asp Val Val Val Lys Gln Val Val Lys Lys Glu Leu Val Phe Thr Pro
145                 150                 155                 160

Thr Asp Thr Thr Val Val Thr Glu Glu Asp Glu Val Ile Gln Ser
                165                 170                 175

Val Val Ser Gly Lys Thr Pro Ser Tyr Ser Leu Glu Ser Lys Leu Gly
            180                 185                 190

Asp Cys Lys Arg Ala Ala Phe Ile Arg Arg Val Ala Leu Glu Arg Ile
            195                 200                 205

Thr Gly Lys Ser Leu Asp Gly Leu Pro Leu Glu Gly Leu Asp Tyr Glu
            210                 215                 220

Ser Ile Leu Gly Gln Cys Cys Glu Met Pro Val Gly Tyr Val Gln Ile
225                 230                 235                 240

Pro Val Gly Val Ala Gly Pro Met Leu Leu Asn Gly Lys Glu Phe Ser
                245                 250                 255

Val Pro Met Ala Thr Thr Glu Gly Cys Leu Val Ala Ser Thr Asn Arg
            260                 265                 270

Gly Phe Lys Ala Ile Tyr Ala Ser Gly Gly Ala Thr Ser Ile Leu Leu
            275                 280                 285

Lys Asp Gly Met Thr Arg Ala Pro Val Val Arg Phe Gly Thr Ala Arg
290                 295                 300

Arg Ala Ala Asp Leu Lys Phe Phe Leu Glu Glu Pro Leu Asn Phe Glu
305                 310                 315                 320

Thr Leu Ala Ser Val Phe Asn Lys Ser Ser Arg Phe Gly Arg Leu Gln
                325                 330                 335

Lys Ile Gln Cys Ala Ile Ala Gly Lys Asn Leu Tyr Met Arg Phe Thr
            340                 345                 350

Cys Ser Thr Gly Asp Ala Met Gly Met Asn Met Val Ser Lys Gly Val
            355                 360                 365

Gln Asn Val Leu Glu Tyr Leu Gln Ser Asp Phe Pro Asp Met Asp Val
            370                 375                 380

Ile Gly Ile Ser Gly Asn Tyr Cys Ser Asp Lys Lys Pro Ala Ala Val
385                 390                 395                 400

Asn Trp Ile Glu Gly Arg Gly Lys Ser Val Val Cys Glu Ala Ile Ile
                405                 410                 415

Lys Glu Asp Ile Val Lys Val Leu Lys Thr Asn Val Ala Ala Leu
            420                 425                 430

Val Glu Leu Asn Met Leu Lys Asn Leu Thr Gly Ser Ala Met Ala Gly
            435                 440                 445

Ala Leu Gly Gly Phe Asn Ala His Ala Ser Asn Ile Val Ser Ala Val
```

```
                450             455             460
Tyr Leu Ala Thr Gly Gln Asp Pro Ala Gln Asn Ile Glu Ser Ser His
465                 470                 475                 480

Cys Ile Thr Met Met Glu Ala Val Asn Asp Gly Lys Asp Leu His Val
                485                 490                 495

Ser Val Thr Met Pro Ser Ile Glu Val Gly Thr Val Gly Gly Gly Thr
                500                 505                 510

Gln Leu Ala Ser Gln Ser Ala Cys Leu Asn Leu Leu Gly Val Lys Gly
            515                 520                 525

Ala Asn Arg Glu Ala Ala Gly Glu Asn Ala Arg Gln Leu Ala Lys Val
            530                 535                 540

Val Ala Gly Ser Val Leu Ala Gly Glu Leu Ser Leu Leu Ser Ala Ile
545                 550                 555                 560

Ala Ala Gly Gln Leu Val Asn Ser His Met Lys Tyr Asn Arg Ser Asn
                565                 570                 575

Lys Asp Val Thr Lys Ala
            580

<210> SEQ ID NO 12
<211> LENGTH: 1776
<212> TYPE: DNA
<213> ORGANISM: Arabidopsis thaliana

<400> SEQUENCE: 12
atggatctcc gtcggaggcc tcctaaacca ccggttacca acaacaacaa ctccaacgga      60
tctttccgtt cttatcagcc tcgcacttcc gatgacgatc atcgtcgccg ggctacaaca     120
attgctcctc caccgaaagc atccgacgcg cttcctcttc cgttatatct cacaaacgcc     180
gttttcttca cgctcttctt ctccgtcgcg tattacctcc tccaccggtg cgtgacaaag     240
atccgttaca atacgcctct tcacgtcgtc actatcacag aactcggcgc cattattgct     300
ctcatcgctt cgtttatcta tctcctaggg ttttttggta ttgactttgt tcagtcattt     360
atctcacgtg cctctggtga tgcttgggat ctcgccgata cgatcgatga tgatgaccac     420
cgccttgtca cgtgctctcc accgactccg atcgtttccg ttgctaaatt acctaatccg     480
gaacctattg ttaccgaatc gcttcctgag gaagacgagg agattgtgaa atcggttatc     540
gacggagtta ttccatcgta ctcgcttgaa tctcgtctcg gtgattgcaa agagcggcg      600 tcgattcgtc gtgaggcgtt gcagagagtc accgggagat cgattgaagg gttaccgttg     660
gatggatttg attatgaatc gattttgggg caatgctgtg agatgcctgt tggatacatt     720
cagattcctg ttgggattgc tggtccattg ttgcttgatg ttatgagta ctctgttcct      780 atggctacaa ccgaaggttg tttggttgct agcactaaca gaggctgcaa ggctatgttt     840
atctctggtg gcgccaccag taccgttctt aaggacggta tgacccgagc acctgttgtt     900
cggttcgctt cggcgagacg agcttcggag cttaagtttt ctcttggagaa tccagagaac    960 tttgatactt tggcagtagt cttcaacagg tcgagtagat ttgcaagact gcaaagtgtt    1020
aaatgcacaa tcgcggggaa gaatgcttat gtaaggttct gttgtagtac tggtgatgct    1080
atggggatga atatggtttc taaaggtgtg cagaatgttc ttgagtatct taccgatgat    1140
ttccctgaca tggatgtgat tggaatctct ggtaacttct gttcggacaa gaaacctgct    1200
gctgtgaact ggattgaggg acgtggtaaa tcagttgttt gcgaggctgt aatcagagga    1260
gagatcgtga caaggtcctt gaaaacgagc gtggctgctt tagtcgagct caacatgctc    1320
aagaacctag ctggctctgc tgttgcaggc tctctaggtg gattcaacgc tcatgccagt    1380
```

-continued

```
aacatagtgt ctgctgtatt catagctact ggccaagatc cagctcaaaa cgtggagagt    1440
tctcaatgca tcaccatgat ggaagctatt aatgacggca aagatatcca tatctcagtc    1500
actatgccat ctatcgaggt ggggacagtg ggaggaggaa cacagcttgc atctcaatca    1560
gcgtgtttaa acctgctcgg agttaaagga gcaagcacag agtcgccggg aatgaacgca    1620
aggaggctag cgacgatcgt agccggagca gttttagctg gagagttatc tttaatgtca    1680
gcaattgcag ctggacagct tgtgagaagt cacatgaaat acaatagatc cagccgagac    1740
atctctggag caacgacaac gacaacaaca acaaca                              1776
```

<210> SEQ ID NO 13
<211> LENGTH: 26
<212> TYPE: DNA
<213> ORGANISM: Artificial Sequence
<220> FEATURE:
<223> OTHER INFORMATION: PRIMER-01

<400> SEQUENCE: 13
caccatggat ctccgtcgga ggcctc                                         26

<210> SEQ ID NO 14
<211> LENGTH: 29
<212> TYPE: DNA
<213> ORGANISM: Artificial Sequence
<220> FEATURE:
<223> OTHER INFORMATION: PRIMER-02

<400> SEQUENCE: 14
cgcctcgagt catgttgttg ttgttgtcg                                      29

<210> SEQ ID NO 15
<211> LENGTH: 29
<212> TYPE: DNA
<213> ORGANISM: Artificial Sequence
<220> FEATURE:
<223> OTHER INFORMATION: PRIMER-03

<400> SEQUENCE: 15
ttgattttga atcgattttg gggcaatgc                                      29

<210> SEQ ID NO 16
<211> LENGTH: 29
<212> TYPE: DNA
<213> ORGANISM: Artificial Sequence
<220> FEATURE:
<223> OTHER INFORMATION: PRIMER-04

<400> SEQUENCE: 16
gattcaaaat caaatccatc caacggtaa                                      29

<210> SEQ ID NO 17
<211> LENGTH: 45
<212> TYPE: DNA
<213> ORGANISM: Artificial Sequence
<220> FEATURE:
<223> OTHER INFORMATION: PRIMER-05

<400> SEQUENCE: 17
ttaccgttgg atggatttga tgatgaatcg attttggggc aatgc                    45

<210> SEQ ID NO 18
<211> LENGTH: 45
<212> TYPE: DNA

```
<213> ORGANISM: Artificial Sequence
<220> FEATURE:
<223> OTHER INFORMATION: PRIMER-06

<400> SEQUENCE: 18
gcattgcccc aaaatcgatt cggcatcaaa tccatccaac ggtaa            45

<210> SEQ ID NO 19
<211> LENGTH: 45
<212> TYPE: DNA
<213> ORGANISM: Artificial Sequence
<220> FEATURE:
<223> OTHER INFORMATION: PRIMER-07

<400> SEQUENCE: 19
ttaccgttgg atggatttga tgaggaatcg attttggggc aatgc            45

<210> SEQ ID NO 20
<211> LENGTH: 45
<212> TYPE: DNA
<213> ORGANISM: Artificial Sequence
<220> FEATURE:
<223> OTHER INFORMATION: PRIMER-08

<400> SEQUENCE: 20
gcattgcccc aaaatcgatt cctcatcaaa tccatccaac ggtaa            45

<210> SEQ ID NO 21
<211> LENGTH: 29
<212> TYPE: DNA
<213> ORGANISM: Artificial Sequence
<220> FEATURE:
<223> OTHER INFORMATION: PRIMER-09

<400> SEQUENCE: 21
atgagttctc tgttcctatg gctacaacc                              29

<210> SEQ ID NO 22
<211> LENGTH: 29
<212> TYPE: DNA
<213> ORGANISM: Artificial Sequence
<220> FEATURE:
<223> OTHER INFORMATION: PRIMER-10

<400> SEQUENCE: 22
acagagaact cataaccatc aagcaacaa                              29

<210> SEQ ID NO 23
<211> LENGTH: 45
<212> TYPE: DNA
<213> ORGANISM: Artificial Sequence
<220> FEATURE:
<223> OTHER INFORMATION: PRIMER-11

<400> SEQUENCE: 23
ttgttgcttg atggttatga ggactctgtt cctatggcta caacc            45

<210> SEQ ID NO 24
<211> LENGTH: 45
<212> TYPE: DNA
<213> ORGANISM: Artificial Sequence
<220> FEATURE:
<223> OTHER INFORMATION: PRIMER-12

<400> SEQUENCE: 24
ggttgtagcc ataggaacag agtcctcata accatcaagc aacaa            45
```

<210> SEQ ID NO 25
<211> LENGTH: 45
<212> TYPE: DNA
<213> ORGANISM: Artificial Sequence
<220> FEATURE:
<223> OTHER INFORMATION: PRIMER-13

<400> SEQUENCE: 25
ttgttgcttg atggttatga ggaatctgtt cctatggcta caacc         45

<210> SEQ ID NO 26
<211> LENGTH: 45
<212> TYPE: DNA
<213> ORGANISM: Artificial Sequence
<220> FEATURE:
<223> OTHER INFORMATION: PRIMER-14

<400> SEQUENCE: 26
ggttgtagcc ataggaacag attcctcata accatcaagc aacaa         45

<210> SEQ ID NO 27
<211> LENGTH: 44
<212> TYPE: DNA
<213> ORGANISM: Artificial Sequence
<220> FEATURE:
<223> OTHER INFORMATION: PRIMER-15

<400> SEQUENCE: 27
ggattgaggg acgtggtaaa gcagttgttt gcgaggctgt aatc          44

<210> SEQ ID NO 28
<211> LENGTH: 44
<212> TYPE: DNA
<213> ORGANISM: Artificial Sequence
<220> FEATURE:
<223> OTHER INFORMATION: PRIMER-16

<400> SEQUENCE: 28
gattacagcc tcgcaaacaa ctgctttacc acgtccctca atcc          44

<210> SEQ ID NO 29
<211> LENGTH: 44
<212> TYPE: DNA
<213> ORGANISM: Artificial Sequence
<220> FEATURE:
<223> OTHER INFORMATION: PRIMER-17

<400> SEQUENCE: 29
ggattgaggg acgtggtaaa gatgttgttt gcgaggctgt aatc          44

<210> SEQ ID NO 30
<211> LENGTH: 44
<212> TYPE: DNA
<213> ORGANISM: Artificial Sequence
<220> FEATURE:
<223> OTHER INFORMATION: PRIMER-18

<400> SEQUENCE: 30
gattacagcc tcgcaaacaa catctttacc acgtccctca atcc          44

<210> SEQ ID NO 31
<211> LENGTH: 44
<212> TYPE: DNA
<213> ORGANISM: Artificial Sequence
<220> FEATURE:

<223> OTHER INFORMATION: PRIMER-19

<400> SEQUENCE: 31
ggattgaggg acgtggtaaa gaagttgttt gcgaggctgt aatc                44

<210> SEQ ID NO 32
<211> LENGTH: 44
<212> TYPE: DNA
<213> ORGANISM: Artificial Sequence
<220> FEATURE:
<223> OTHER INFORMATION: PRIMER-20

<400> SEQUENCE: 32
gattacagcc tcgcaaacaa cttctttacc acgtccctca atcc                44

<210> SEQ ID NO 33
<211> LENGTH: 30
<212> TYPE: DNA
<213> ORGANISM: Artificial Sequence
<220> FEATURE:
<223> OTHER INFORMATION: PRIMER-21

<400> SEQUENCE: 33
gctgcaggcc aagatccagc tcaaaacgtg                                30

<210> SEQ ID NO 34
<211> LENGTH: 28
<212> TYPE: DNA
<213> ORGANISM: Artificial Sequence
<220> FEATURE:
<223> OTHER INFORMATION: PRIMER-22

<400> SEQUENCE: 34
ggcctgcagc tatgaataca gcagacac                                  28

<210> SEQ ID NO 35
<211> LENGTH: 30
<212> TYPE: DNA
<213> ORGANISM: Artificial Sequence
<220> FEATURE:
<223> OTHER INFORMATION: PRIMER-23

<400> SEQUENCE: 35
gctgatggcc aagatccagc tcaaaacgtg                                30

<210> SEQ ID NO 36
<211> LENGTH: 28
<212> TYPE: DNA
<213> ORGANISM: Artificial Sequence
<220> FEATURE:
<223> OTHER INFORMATION: PRIMER-24

<400> SEQUENCE: 36
ggccatcagc tatgaataca gcagacac                                  28

<210> SEQ ID NO 37
<211> LENGTH: 30
<212> TYPE: DNA
<213> ORGANISM: Artificial Sequence
<220> FEATURE:
<223> OTHER INFORMATION: PRIMER-25

<400> SEQUENCE: 37
gctgaaggcc aagatccagc tcaaaacgtg                                30

```
<210> SEQ ID NO 38
<211> LENGTH: 28
<212> TYPE: DNA
<213> ORGANISM: Artificial Sequence
<220> FEATURE:
<223> OTHER INFORMATION: PRIMER-26

<400> SEQUENCE: 38
ggccttcagc tatgaataca gcagacac                                        28

<210> SEQ ID NO 39
<211> LENGTH: 44
<212> TYPE: DNA
<213> ORGANISM: Artificial Sequence
<220> FEATURE:
<223> OTHER INFORMATION: PRIMER-27

<400> SEQUENCE: 39
ccatctatcg aggtgggggc agtgggagga ggaacacagc ttgc                      44

<210> SEQ ID NO 40
<211> LENGTH: 44
<212> TYPE: DNA
<213> ORGANISM: Artificial Sequence
<220> FEATURE:
<223> OTHER INFORMATION: PRIMER-28

<400> SEQUENCE: 40
gcaagctgtg ttcctcctcc cactgccccc acctcgatag atgg                      44

<210> SEQ ID NO 41
<211> LENGTH: 44
<212> TYPE: DNA
<213> ORGANISM: Artificial Sequence
<220> FEATURE:
<223> OTHER INFORMATION: PRIMER-29

<400> SEQUENCE: 41
ccatctatcg aggtggggga tgtgggagga ggaacacagc ttgc                      44

<210> SEQ ID NO 42
<211> LENGTH: 44
<212> TYPE: DNA
<213> ORGANISM: Artificial Sequence
<220> FEATURE:
<223> OTHER INFORMATION: PRIMER-30

<400> SEQUENCE: 42
gcaagctgtg ttcctcctcc cacatccccc acctcgatag atgg                      44

<210> SEQ ID NO 43
<211> LENGTH: 44
<212> TYPE: DNA
<213> ORGANISM: Artificial Sequence
<220> FEATURE:
<223> OTHER INFORMATION: PRIMER-31

<400> SEQUENCE: 43
ccatctatcg aggtggggga agtgggagga ggaacacagc ttgc                      44

<210> SEQ ID NO 44
<211> LENGTH: 44
<212> TYPE: DNA
<213> ORGANISM: Artificial Sequence
<220> FEATURE:
<223> OTHER INFORMATION: PRIMER-32
```

<400> SEQUENCE: 44
gcaagctgtg ttcctcctcc cacttccccc acctcgatag atgg                44

<210> SEQ ID NO 45
<211> LENGTH: 45
<212> TYPE: DNA
<213> ORGANISM: Artificial Sequence
<220> FEATURE:
<223> OTHER INFORMATION: PRIMER-33

<400> SEQUENCE: 45
attgctcctc caccgaaagc agccgacgcg cttcctcttc cgtta               45

<210> SEQ ID NO 46
<211> LENGTH: 45
<212> TYPE: DNA
<213> ORGANISM: Artificial Sequence
<220> FEATURE:
<223> OTHER INFORMATION: PRIMER-34

<400> SEQUENCE: 46
taacggaaga ggaagcgcgt cggctgcttt cggtggagga gcaat               45

<210> SEQ ID NO 47
<211> LENGTH: 45
<212> TYPE: DNA
<213> ORGANISM: Artificial Sequence
<220> FEATURE:
<223> OTHER INFORMATION: PRIMER-35

<400> SEQUENCE: 47
attgctcctc caccgaaagc agacgacgcg cttcctcttc cgtta               45

<210> SEQ ID NO 48
<211> LENGTH: 45
<212> TYPE: DNA
<213> ORGANISM: Artificial Sequence
<220> FEATURE:
<223> OTHER INFORMATION: PRIMER-36

<400> SEQUENCE: 48
taacggaaga ggaagcgcgt cgtctgcttt cggtggagga gcaat               45

<210> SEQ ID NO 49
<211> LENGTH: 45
<212> TYPE: DNA
<213> ORGANISM: Artificial Sequence
<220> FEATURE:
<223> OTHER INFORMATION: PRIMER-37

<400> SEQUENCE: 49
attgctcctc caccgaaagc agaagacgcg cttcctcttc cgtta               45

<210> SEQ ID NO 50
<211> LENGTH: 45
<212> TYPE: DNA
<213> ORGANISM: Artificial Sequence
<220> FEATURE:
<223> OTHER INFORMATION: PRIMER-38

<400> SEQUENCE: 50
taacggaaga ggaagcgcgt cttctgcttt cggtggagga gcaat               45

<210> SEQ ID NO 51
<211> LENGTH: 45

```
<212> TYPE: DNA
<213> ORGANISM: Artificial Sequence
<220> FEATURE:
<223> OTHER INFORMATION: PRIMER-39

<400> SEQUENCE: 51
aatacgcctc ttcacgtcgt cgcaatcaca gaactcggcg ccatt            45

<210> SEQ ID NO 52
<211> LENGTH: 45
<212> TYPE: DNA
<213> ORGANISM: Artificial Sequence
<220> FEATURE:
<223> OTHER INFORMATION: PRIMER-40

<400> SEQUENCE: 52
aatggcgccg agttctgtga ttgcgacgac gtgaagaggc gtatt            45

<210> SEQ ID NO 53
<211> LENGTH: 45
<212> TYPE: DNA
<213> ORGANISM: Artificial Sequence
<220> FEATURE:
<223> OTHER INFORMATION: PRIMER-41

<400> SEQUENCE: 53
aatacgcctc ttcacgtcgt cgatatcaca gaactcggcg ccatt            45

<210> SEQ ID NO 54
<211> LENGTH: 45
<212> TYPE: DNA
<213> ORGANISM: Artificial Sequence
<220> FEATURE:
<223> OTHER INFORMATION: PRIMER-42

<400> SEQUENCE: 54
aatggcgccg agttctgtga tatcgacgac gtgaagaggc gtatt            45

<210> SEQ ID NO 55
<211> LENGTH: 45
<212> TYPE: DNA
<213> ORGANISM: Artificial Sequence
<220> FEATURE:
<223> OTHER INFORMATION: PRIMER-43

<400> SEQUENCE: 55
aatacgcctc ttcacgtcgt cgaaatcaca gaactcggcg ccatt            45

<210> SEQ ID NO 56
<211> LENGTH: 45
<212> TYPE: DNA
<213> ORGANISM: Artificial Sequence
<220> FEATURE:
<223> OTHER INFORMATION: PRIMER-44

<400> SEQUENCE: 56
aatggcgccg agttctgtga tttcgacgac gtgaagaggc gtatt            45

<210> SEQ ID NO 57
<211> LENGTH: 43
<212> TYPE: DNA
<213> ORGANISM: Artificial Sequence
<220> FEATURE:
<223> OTHER INFORMATION: PRIMER-45

<400> SEQUENCE: 57
```
cgagtagatt tgcaagactg caagccgtta aatgcacaat cgc    43

<210> SEQ ID NO 58
<211> LENGTH: 43
<212> TYPE: DNA
<213> ORGANISM: Artificial Sequence
<220> FEATURE:
<223> OTHER INFORMATION: PRIMER-46

<400> SEQUENCE: 58
gcgattgtgc atttaacggc ttgcagtctt gcaaatctac tcg    43

<210> SEQ ID NO 59
<211> LENGTH: 43
<212> TYPE: DNA
<213> ORGANISM: Artificial Sequence
<220> FEATURE:
<223> OTHER INFORMATION: PRIMER-47

<400> SEQUENCE: 59
cgagtagatt tgcaagactg caagatgtta aatgcacaat cgc    43

<210> SEQ ID NO 60
<211> LENGTH: 43
<212> TYPE: DNA
<213> ORGANISM: Artificial Sequence
<220> FEATURE:
<223> OTHER INFORMATION: PRIMER-48

<400> SEQUENCE: 60
gcgattgtgc atttaacatc ttgcagtctt gcaaatctac tcg    43

<210> SEQ ID NO 61
<211> LENGTH: 43
<212> TYPE: DNA
<213> ORGANISM: Artificial Sequence
<220> FEATURE:
<223> OTHER INFORMATION: PRIMER-49

<400> SEQUENCE: 61
cgagtagatt tgcaagactg caagaagtta aatgcacaat cgc    43

<210> SEQ ID NO 62
<211> LENGTH: 43
<212> TYPE: DNA
<213> ORGANISM: Artificial Sequence
<220> FEATURE:
<223> OTHER INFORMATION: PRIMER-50

<400> SEQUENCE: 62
gcgattgtgc atttaacttc ttgcagtctt gcaaatctac tcg    43

<210> SEQ ID NO 63
<211> LENGTH: 34
<212> TYPE: DNA
<213> ORGANISM: Artificial Sequence
<220> FEATURE:
<223> OTHER INFORMATION: PRIMER-51

<400> SEQUENCE: 63
caatagagcc agccgagaca tctctggagc aacg    34

<210> SEQ ID NO 64
<211> LENGTH: 35
<212> TYPE: DNA
<213> ORGANISM: Artificial Sequence

```
<220> FEATURE:
<223> OTHER INFORMATION: PRIMER-52

<400> SEQUENCE: 64
cggctggctc tattgtattt catgtgactt ctcac                              35

<210> SEQ ID NO 65
<211> LENGTH: 43
<212> TYPE: DNA
<213> ORGANISM: Artificial Sequence
<220> FEATURE:
<223> OTHER INFORMATION: PRIMER-53

<400> SEQUENCE: 65
gtcacatgaa atacaataga gacagccgag acatctctgg agc                     43

<210> SEQ ID NO 66
<211> LENGTH: 43
<212> TYPE: DNA
<213> ORGANISM: Artificial Sequence
<220> FEATURE:
<223> OTHER INFORMATION: PRIMER-54

<400> SEQUENCE: 66
gctccagaga tgtctcggct gtctctattg tatttcatgt gac                     43

<210> SEQ ID NO 67
<211> LENGTH: 43
<212> TYPE: DNA
<213> ORGANISM: Artificial Sequence
<220> FEATURE:
<223> OTHER INFORMATION: PRIMER-55

<400> SEQUENCE: 67
gtcacatgaa atacaataga gaaagccgag acatctctgg agc                     43

<210> SEQ ID NO 68
<211> LENGTH: 43
<212> TYPE: DNA
<213> ORGANISM: Artificial Sequence
<220> FEATURE:
<223> OTHER INFORMATION: PRIMER-56

<400> SEQUENCE: 68
gctccagaga tgtctcggct ttctctattg tatttcatgt gac                     43

<210> SEQ ID NO 69
<211> LENGTH: 562
<212> TYPE: PRT
<213> ORGANISM: Arabidopsis thaliana

<400> SEQUENCE: 69

Met Glu Asp Leu Arg Arg Arg Phe Pro Thr Lys Lys Asn Gly Glu Glu
1               5                   10                  15

Ile Ser Asn Val Ala Val Asp Pro Pro Leu Arg Lys Ala Ser Asp Ala
            20                  25                  30

Leu Pro Leu Pro Leu Tyr Leu Thr Asn Thr Phe Phe Leu Ser Leu Phe
        35                  40                  45

Phe Ala Thr Val Tyr Phe Leu Leu Ser Arg Trp Arg Glu Lys Ile Arg
    50                  55                  60

Asn Ser Thr Pro Leu His Val Val Asp Leu Ser Glu Ile Cys Ala Leu
65                  70                  75                  80

Ile Gly Phe Val Ala Ser Phe Ile Tyr Leu Leu Gly Phe Cys Gly Ile
```

```
                       85                  90                  95
Asp Leu Ile Phe Arg Ser Ser Asp Asp Val Trp Val Asn Asp
                100                 105                 110
Gly Met Ile Pro Cys Asn Gln Ser Leu Asp Cys Arg Glu Val Leu Pro
            115                 120                 125
Ile Lys Pro Asn Ser Val Asp Pro Pro Arg Glu Ser Glu Leu Asp Ser
130                 135                 140
Val Glu Asp Glu Glu Ile Val Lys Leu Val Ile Asp Gly Thr Ile Pro
145                 150                 155                 160
Ser Tyr Ser Leu Glu Thr Lys Leu Gly Asp Cys Lys Arg Ala Ala Ala
                165                 170                 175
Ile Arg Arg Glu Ala Val Gln Arg Ile Thr Gly Lys Ser Leu Thr Gly
            180                 185                 190
Leu Pro Leu Glu Gly Phe Asp Tyr Asn Ser Ile Leu Gly Gln Cys Cys
        195                 200                 205
Glu Met Pro Val Gly Tyr Val Gln Ile Pro Val Gly Ile Ala Gly Pro
    210                 215                 220
Leu Leu Leu Asp Gly Val Glu Tyr Ser Val Pro Met Ala Thr Thr Glu
225                 230                 235                 240
Gly Cys Leu Val Ala Ser Thr Asn Arg Gly Phe Lys Ala Ile His Leu
                245                 250                 255
Ser Gly Gly Ala Phe Ser Val Leu Val Lys Asp Ala Met Thr Arg Ala
            260                 265                 270
Pro Val Val Arg Phe Pro Ser Ala Arg Ala Ala Leu Val Met Phe
        275                 280                 285
Tyr Leu Gln Asp Pro Ser Asn Phe Glu Arg Leu Ser Leu Ile Phe Asn
    290                 295                 300
Lys Ser Ser Arg Phe Ala Arg Leu Gln Ser Ile Thr Cys Thr Ile Ala
305                 310                 315                 320
Gly Arg Asn Leu Tyr Pro Arg Phe Ala Cys Ser Thr Gly Asp Ala Met
                325                 330                 335
Gly Met Asn Met Val Ser Lys Gly Val Gln Asn Val Leu Asp Phe Val
            340                 345                 350
Lys Ser Glu Phe Pro Asp Met Asp Val Ile Gly Ile Ser Gly Asn Tyr
        355                 360                 365
Cys Ser Asp Lys Lys Ala Ser Ala Val Asn Trp Ile Glu Gly Arg Gly
    370                 375                 380
Lys His Val Val Cys Glu Ala Phe Ile Lys Ala Glu Ile Val Glu Lys
385                 390                 395                 400
Val Leu Lys Thr Ser Val Glu Ala Leu Val Glu Leu Asn Thr Leu Lys
                405                 410                 415
Asn Leu Val Gly Ser Ala Met Ala Gly Ser Leu Gly Gly Phe Asn Ala
            420                 425                 430
His Ser Ser Asn Ile Val Ser Ala Val Phe Ile Ala Thr Gly Gln Asp
        435                 440                 445
Pro Ala Gln Asn Val Glu Ser Ser His Cys Met Thr Met Ile Leu Pro
    450                 455                 460
Asp Gly Asp Leu His Ile Ser Val Ser Met Pro Cys Ile Glu Val
465                 470                 475                 480
Gly Thr Val Gly Gly Thr Gln Leu Ala Ser Gln Ala Ala Cys Leu
                485                 490                 495
Asn Leu Leu Gly Val Lys Gly Ser Asn Asn Glu Lys Pro Gly Ser Asn
            500                 505                 510
```

-continued

Ala Gln Gln Leu Ala Arg Ile Val Ala Gly Ser Val Leu Ala Gly Glu
        515                 520                 525

Leu Ser Leu Met Ser Ala Ile Ala Ala Gly Gln Leu Val Lys Ser His
    530                 535                 540

Met Lys Tyr Asn Arg Ser Ser Arg Asp Ile Gly Pro Ser Ser Gln Val
545                 550                 555                 560

Asn Arg

<210> SEQ ID NO 70
<211> LENGTH: 210
<212> TYPE: PRT
<213> ORGANISM: Hevea brasiliensis

<400> SEQUENCE: 70

Leu Glu Ser Asp Phe Ala Asp Met Asp Val Ile Gly Ile Ser Gly Asn
1               5                   10                  15

Phe Cys Ser Asp Lys Lys Pro Ala Ala Val Asn Trp Ile Glu Gly Arg
            20                  25                  30

Gly Lys Ser Val Val Cys Glu Ala Ile Ile Lys Glu Val Val Lys
        35                  40                  45

Lys Val Leu Lys Thr Asp Val Ala Leu Leu Val Glu Leu Asn Met Leu
    50                  55                  60

Lys Asn Leu Ala Gly Ser Ala Val Ala Gly Ala Leu Gly Gly Phe Asn
65                  70                  75                  80

Ala His Ala Gly Asn Ile Val Ser Ala Ile Phe Ile Ala Thr Gly Gln
            85                  90                  95

Asp Pro Ala Gln Asn Val Glu Ser Ser His Cys Ile Thr Met Met Glu
            100                 105                 110

Ala Val Asn Asp Gly Lys Asp Leu His Ile Ser Val Thr Leu Pro Ser
        115                 120                 125

Ile Glu Val Gly Thr Val Gly Gly Thr Gln Leu Ala Ser Gln Ser
    130                 135                 140

Ala Cys Leu Asn Leu Leu Gly Val Met Gly Ala Cys Lys Glu Ser Pro
145                 150                 155                 160

Gly Ser Tyr Ser Arg Leu Leu Ala Thr Ile Val Ala Gly Ser Val Leu
            165                 170                 175

Ala Gly Glu Leu Ser Leu Met Ser Ala Ile Ala Ala Gly Gln Leu Val
            180                 185                 190

Lys Ser His Met Lys Tyr Asn Arg Ser Ser Lys Asp Val Ser Lys Ala
        195                 200                 205

Ala Ser
210

<210> SEQ ID NO 71
<211> LENGTH: 586
<212> TYPE: PRT
<213> ORGANISM: Hevea brasiliensis

<400> SEQUENCE: 71

Met Asp Glu Val Arg Arg Pro Pro Lys His Ile Val Arg Lys Asp
1               5                   10                  15

His Asp Gly Glu Val Leu Asn Ser Phe Ser His Gly His His Leu Pro
            20                  25                  30

Pro Leu Lys Pro Ser Asp Tyr Ser Leu Pro Leu Ser Leu Tyr Leu Ala
        35                  40                  45

```
Asn Ala Leu Val Phe Ser Leu Phe Phe Ser Val Ala Tyr Phe Leu Leu
 50                  55                  60

His Arg Trp Arg Glu Lys Ile Arg Lys Ser Thr Pro Leu His Ile Val
 65                  70                  75                  80

Thr Phe Pro Glu Ile Ala Ala Leu Ile Cys Leu Val Ala Ser Val Ile
                 85                  90                  95

Tyr Leu Leu Gly Phe Phe Gly Ile Gly Phe Val His Ser Phe Ser Arg
                100                 105                 110

Ala Ser Thr Asp Ser Trp Asp Val Glu Glu Tyr Asp Asp Asp Asn Ile
                115                 120                 125

Ile Ile Lys Glu Asp Thr Arg Pro Thr Gly Ala Cys Ala Ala Pro Ser
130                 135                 140

Leu Asp Cys Ser Leu Ser Leu Pro Thr Lys Ile His Ala Pro Ile Val
145                 150                 155                 160

Ser Thr Thr Thr Thr Ser Thr Leu Ser Asp Asp Asp Glu Gln Ile Ile
                165                 170                 175

Lys Ser Val Val Ser Gly Ser Ile Pro Ser Tyr Ser Leu Glu Ser Lys
                180                 185                 190

Leu Gly Asn Cys Lys Arg Ala Ala Leu Ile Arg Arg Glu Thr Leu Gln
                195                 200                 205

Arg Met Ser Gly Arg Ser Leu Glu Gly Leu Pro Leu Asp Gly Phe Asp
210                 215                 220

Tyr Glu Ser Ile Leu Gly Gln Cys Cys Glu Met Ala Ile Gly Tyr Val
225                 230                 235                 240

Gln Ile Pro Val Gly Ile Ala Gly Pro Leu Leu Leu Asp Gly Lys Glu
                245                 250                 255

Tyr Thr Val Pro Met Ala Thr Thr Glu Gly Cys Leu Val Ala Ser Ala
                260                 265                 270

Asn Arg Gly Cys Lys Ala Ile Tyr Ala Ser Gly Gly Ala Thr Ser Val
                275                 280                 285

Leu Leu Arg Asp Gly Met Thr Arg Ala Pro Val Val Arg Phe Pro Thr
290                 295                 300

Ala Lys Arg Ala Ala Asp Leu Lys Phe Phe Met Glu Asp Pro Asp Asn
305                 310                 315                 320

Phe Asp Thr Ile Ala Val Val Phe Asn Lys Ser Ser Arg Phe Ala Arg
                325                 330                 335

Leu Gln Ser Val Gln Cys Ala Ile Ala Gly Lys Asn Leu Tyr Met Arg
                340                 345                 350

Phe Ser Cys Ser Thr Gly Asp Ala Met Gly Met Asn Met Val Ser Lys
                355                 360                 365

Ala Val Gln Asn Val Ile Asp Tyr Leu Gln Asn Asp Phe Pro Asp Met
370                 375                 380

Asp Val Ile Gly Leu Thr Gly Asn Phe Cys Ala Asp Lys Lys Ala Ala
385                 390                 395                 400

Ala Val Asn Trp Ile Glu Gly Arg Gly Lys Ser Val Val Cys Glu Ala
                405                 410                 415

Ile Ile Lys Glu Glu Val Val Lys Lys Val Leu Lys Thr Asn Val Ala
                420                 425                 430

Ala Leu Val Glu Leu Asn Met Ile Lys Asn Leu Thr Gly Ser Ala Val
                435                 440                 445

Ala Gly Ser Leu Gly Gly Phe Asn Ala His Ala Ser Asn Met Val Thr
450                 455                 460

Ala Val Tyr Ile Ala Thr Gly Gln Asp Pro Ala Gln Asn Val Glu Ser
```

```
            465                 470                 475                 480
        Ser His Cys Ile Thr Met Met Glu Ala Val Asn Asp Gly Lys Asp Leu
                            485                 490                 495

His Ile Ser Val Ser Met Pro Ser Ile Glu Leu Gly Thr Val Gly Gly
                            500                 505                 510

Gly Thr Gln Leu Ala Ser Gln Ser Ala Cys Leu Asn Leu Leu Gly Val
                            515                 520                 525

Lys Gly Ala Ser Lys Asp Ser Pro Gly Ser Asn Ser Arg Leu Leu Ala
                            530                 535                 540

Thr Ile Val Ala Gly Ser Val Leu Ala Gly Glu Leu Ser Leu Met Ser
        545                 550                 555                 560

Ala Ile Ala Ala Gly Gln Leu Val Asn Ser His Met Lys Tyr Asn Arg
                            565                 570                 575

Ser Ala Lys Asp Val Ser Lys Ile Thr Phe
                            580                 585

<210> SEQ ID NO 72
<211> LENGTH: 606
<212> TYPE: PRT
<213> ORGANISM: Hevea brasiliensis

<400> SEQUENCE: 72

Met Asp Val Arg Arg Pro Thr Ser Gly Lys Thr Ile His Ser Val
        1               5                   10                  15

Lys Pro Lys Ser Val Glu Asp Glu Ser Ala Gln Lys Pro Ser Asp Ala
                            20                  25                  30

Leu Pro Leu Pro Leu Tyr Leu Ile Asn Ala Leu Cys Phe Thr Val Phe
                            35                  40                  45

Phe Tyr Val Val Tyr Phe Leu Leu Ser Arg Trp Arg Glu Lys Ile Arg
        50                  55                  60

Thr Ser Thr Pro Leu His Val Val Ala Leu Ser Glu Ile Ala Ala Ile
        65                  70                  75                  80

Val Ala Phe Val Ala Ser Phe Ile Tyr Leu Leu Gly Phe Phe Gly Ile
                            85                  90                  95

Asp Phe Val Gln Ser Leu Ile Leu Arg Pro Pro Thr Asp Met Trp Ala
                            100                 105                 110

Val Asp Asp Asp Glu Glu Glu Thr Glu Glu Gly Ile Val Leu Arg Glu
                            115                 120                 125

Asp Thr Arg Lys Leu Pro Cys Gly Gln Ala Leu Asp Cys Ser Leu Ser
                            130                 135                 140

Ala Pro Pro Leu Ser Arg Ala Val Val Ser Ser Pro Lys Ala Met Asp
        145                 150                 155                 160

Pro Ile Val Leu Pro Ser Pro Lys Pro Lys Val Phe Asp Glu Ile Pro
                            165                 170                 175

Phe Pro Thr Thr Thr Thr Ile Pro Ile Leu Gly Asp Glu Asp Glu Glu
                            180                 185                 190

Ile Ile Lys Ser Val Val Ala Gly Thr Ile Pro Ser Tyr Ser Leu Glu
                            195                 200                 205

Ser Lys Leu Gly Asp Cys Lys Arg Ala Ala Ile Arg Arg Glu Ala
                            210                 215                 220

Leu Gln Arg Ile Thr Gly Lys Ser Leu Ser Gly Leu Pro Leu Glu Gly
        225                 230                 235                 240

Phe Asp Tyr Glu Ser Ile Leu Gly Gln Cys Cys Glu Met Pro Val Gly
                            245                 250                 255
```

```
Tyr Val Gln Ile Pro Val Gly Ile Ala Gly Pro Leu Leu Asp Gly
            260                 265                 270

Lys Glu Tyr Ser Val Pro Met Ala Thr Thr Glu Gly Cys Leu Val Ala
            275                 280                 285

Ser Thr Asn Arg Gly Cys Lys Ala Ile His Leu Ser Gly Gly Ala Thr
290                 295                 300

Ser Val Leu Leu Arg Asp Gly Met Thr Arg Ala Pro Val Val Arg Phe
305                 310                 315                 320

Gly Thr Ala Lys Arg Ala Ala Gln Leu Lys Leu Tyr Leu Glu Asp Pro
            325                 330                 335

Ala Asn Phe Glu Thr Leu Ser Thr Ser Phe Asn Lys Ser Ser Arg Phe
            340                 345                 350

Gly Arg Leu Gln Ser Ile Lys Cys Ala Ile Ala Gly Lys Asn Leu Tyr
            355                 360                 365

Met Arg Phe Cys Cys Ser Thr Gly Asp Ala Met Gly Met Asn Met Val
            370                 375                 380

Ser Lys Gly Val Gln Asn Val Leu Asn Phe Leu Gln Asn Asp Phe Pro
385                 390                 395                 400

Asp Met Asp Val Ile Gly Leu Ser Gly Asn Phe Cys Ser Asp Lys Lys
                405                 410                 415

Pro Ala Ala Val Asn Trp Ile Glu Gly Arg Gly Lys Ser Val Val Cys
                420                 425                 430

Glu Ala Ile Ile Lys Gly Asp Val Lys Lys Val Leu Lys Thr Asn
            435                 440                 445

Val Glu Ala Leu Val Glu Leu Asn Met Leu Lys Asn Leu Thr Gly Ser
            450                 455                 460

Ala Met Ala Gly Ala Leu Gly Gly Phe Asn Ala His Ala Ser Asn Ile
465                 470                 475                 480

Val Thr Ala Ile Tyr Ile Ala Thr Gly Gln Asp Pro Ala Gln Asn Val
                485                 490                 495

Glu Ser Ser Asn Cys Ile Thr Met Met Glu Ala Val Asn Asp Gly Gln
                500                 505                 510

Asp Leu His Val Ser Val Thr Met Pro Ser Ile Glu Val Gly Thr Val
            515                 520                 525

Gly Gly Gly Thr Gln Leu Ala Ser Gln Ser Ala Cys Leu Asn Leu Leu
530                 535                 540

Gly Val Lys Gly Ala Ser Lys Glu Thr Pro Gly Ala Asn Ser Arg Val
545                 550                 555                 560

Leu Ala Ser Ile Val Ala Gly Ser Val Leu Ala Glu Leu Ser Leu
                565                 570                 575

Met Ser Ala Ile Ala Ala Gly Gln Leu Val Asn Ser His Met Lys Tyr
            580                 585                 590

Asn Arg Ala Asn Lys Glu Ala Ala Val Ser Lys Pro Ser Ser
            595                 600                 605

<210> SEQ ID NO 73
<211> LENGTH: 526
<212> TYPE: PRT
<213> ORGANISM: Hevea brasiliensis

<400> SEQUENCE: 73

Met Asp Ala Arg Arg Arg Pro Thr Ser Gly Asn Pro Ile His Ser Arg
1               5                   10                  15

Lys Val Lys Ala Leu Glu Asp Glu Asn Thr Gln Lys Pro Ser Asp Ala
            20                  25                  30
```

```
Leu Pro Leu His Ile Tyr Leu Thr Asn Ala Leu Cys Phe Thr Val Phe
        35                  40                  45

Phe Trp Val Val Tyr Phe Leu Leu Ser Arg Trp Arg Glu Lys Ile Arg
    50                  55                  60

Thr Ser Ala Pro Leu His Val Val Thr Leu Ser Glu Ile Ala Ala Ile
65                  70                  75                  80

Val Ala Leu Phe Ala Ser Phe Ile Tyr Leu Leu Gly Phe Phe Gly Ile
                85                  90                  95

Asp Phe Val Gln Ser Leu Ile Leu Arg Pro Pro Thr Asp Met Trp Ala
            100                 105                 110

Val Asp Asp Glu Glu Glu Pro Ala Glu Gln Ile Leu Leu Lys Glu
            115                 120                 125

Asp Ala Arg Lys Ser Pro Cys Gly Gln Ala Leu Asp Cys Ser Leu Thr
        130                 135                 140

Ala Pro Pro Leu Ser Arg Pro Ile Val Ser Ser Lys Ala Val Gly
145                 150                 155                 160

Pro Ile Val Leu Pro Ser Pro Lys Pro Lys Val Val Glu Glu Ile Ser
                165                 170                 175

Phe Pro Ala Ile Thr Thr Thr Ala Thr Leu Gly Glu Glu Asp Glu Glu
            180                 185                 190

Ile Ile Lys Ser Val Val Ala Gly Thr Thr Pro Ser Tyr Ser Leu Glu
        195                 200                 205

Ser Lys Leu Gly Asp Cys Lys Arg Ala Ala Ala Ile Arg Arg Glu Ala
    210                 215                 220

Leu Gln Arg Ile Thr Gly Lys Ser Leu Ser Gly Leu Pro Leu Glu Gly
225                 230                 235                 240

Phe Asp Tyr Glu Ser Ile Leu Gly Gln Cys Cys Glu Met Pro Val Gly
                245                 250                 255

Tyr Val Gln Ile Pro Val Gly Ile Ala Gly Pro Leu Leu Leu Asp Gly
            260                 265                 270

Lys Glu Val Ser Val Pro Met Ala Thr Thr Glu Gly Cys Leu Val Ala
        275                 280                 285

Ser Thr Asn Arg Gly Cys Lys Ala Ile His Ile Ser Gly Gly Ala Thr
    290                 295                 300

Ser Val Val Leu Arg Asp Gly Met Thr Arg Ala Pro Val Val Arg Phe
305                 310                 315                 320

Gly Thr Ala Lys Arg Ala Ala Gln Leu Lys Phe Tyr Leu Glu Asp Ser
                325                 330                 335

Ala Asn Phe Glu Thr Leu Ser Thr Val Phe Asn Lys Ser Ser Arg Phe
            340                 345                 350

Gly Arg Leu Gln Ser Ile Arg Cys Ala Ile Ala Gly Lys Asn Leu Tyr
        355                 360                 365

Ile Arg Phe Cys Cys Gly Thr Gly Asp Ala Met Gly Met Asn Met Val
    370                 375                 380

Ser Lys Gly Val Gln Asn Val Leu Asp Phe Leu Gln Asn Asp Phe Pro
385                 390                 395                 400

Asp Met Asp Val Ile Gly Val Ser Gly Asn Phe Cys Ser Asp Lys Lys
                405                 410                 415

Pro Ala Ala Val Asn Trp Ile Glu Gly Arg Gly Lys Ser Val Ala Cys
            420                 425                 430

Glu Ala Ile Ile Lys Gly Asp Val Val Lys Val Leu Lys Thr Asn
        435                 440                 445
```

Val Glu Ala Leu Val Glu Leu Asn Met Leu Lys Asn Leu Thr Gly Ser
450                 455                 460

Ala Leu Ala Gly Ala Leu Gly Gly Phe Asn Ala His Ala Ser Asn Ile
465                 470                 475                 480

Val Thr Ala Ile Tyr Ile Ala Thr Gly Gln Asp Pro Ala Gln Asn Val
                485                 490                 495

Glu Ser Ser His Cys Ile Thr Met Met Glu Ala Val Asn Asp Gly Gln
                500                 505                 510

Asp Leu His Val Ser Val Thr Met Pro Ser Ile Glu Val Asn
                515                 520                 525

<210> SEQ ID NO 74
<211> LENGTH: 459
<212> TYPE: PRT
<213> ORGANISM: Lactuca sativa Lettuce

<400> SEQUENCE: 74

Met Gly Lys Ala Gln Phe Asp Gln His Ser Glu Asp Gln Met Leu Lys
1               5                   10                  15

Thr Glu Asn Lys Lys Met Val Asp Ser Pro Lys Ala Phe Asp Ala Ile
                20                  25                  30

Ser Ile Pro Met Gly Ile Phe Phe Thr Val Phe Phe Ser Val Val Tyr
                35                  40                  45

Tyr Leu Leu Ile Arg Trp Arg Glu Lys Ile Arg Asn Ser Thr Pro Leu
50                  55                  60

His Val Val Asn Met Ser Glu Met Ala Ala Ile Ile Thr Phe Phe Ala
65                  70                  75                  80

Ser Cys Ile Tyr Leu Leu Gly Phe Phe Gly Met Asn Phe Val Gln Ala
                85                  90                  95

Thr Pro Phe Thr Glu Thr Glu Glu Asp Glu Val Glu Gly Glu Thr
                100                 105                 110

Thr Pro Cys Gly Ala Ser Ile Ile Arg Glu Ser Asp Ile Val Ser Val
                115                 120                 125

Lys Glu Val Met Lys Lys Glu Val Thr Val Ile Val Ala Thr Asp
130                 135                 140

Thr Val Val Ser Glu Glu Asp Glu Glu Val Ile Gln Ala Val Val Ser
145                 150                 155                 160

Gly Arg Thr Pro Ser Tyr Ser Leu Glu Ser Lys Leu Gly Asp Cys Lys
                165                 170                 175

Arg Ala Ala Phe Ile Arg Arg Val Ala Leu Glu Arg Ile Thr Gly Lys
                180                 185                 190

Ser Leu Glu Gly Leu Pro Leu Glu Gly Leu Asp Tyr Glu Ser Ile Leu
                195                 200                 205

Gly Gln Cys Cys Glu Met Pro Val Gly Tyr Val Gln Ile Pro Val Gly
                210                 215                 220

Ile Ala Gly Pro Leu Leu Leu Asp Gly Met Glu Phe Ser Val Pro Met
225                 230                 235                 240

Ala Thr Thr Glu Gly Cys Leu Val Ala Ser Thr Asn Arg Gly Cys Lys
                245                 250                 255

Ala Ile Tyr Val Ser Gly Gly Ala Thr Ser Val Leu Leu Lys Asp Gly
                260                 265                 270

Met Thr Arg Ala Pro Val Val Arg Phe Ala Thr Ala Lys Arg Ala Ala
                275                 280                 285

Asp Leu Lys Phe Phe Leu Glu Glu Pro Leu Asn Phe Gly Thr Leu Ala
                290                 295                 300

Ser Val Phe Asn Lys Ser Ser Arg Phe Gly Arg Leu Gln Thr Ile Arg
305                 310                 315                 320

Cys Ala Ile Ala Gly Lys Asn Leu Tyr Ile Arg Phe Thr Cys Ser Thr
                325                 330                 335

Gly Asp Ala Met Gly Met Asn Met Val Ser Lys Gly Val Gln Asn Val
            340                 345                 350

Leu Glu Tyr Leu Gln Ala Asp Phe Pro Asp Met Asp Val Ile Gly Ile
            355                 360                 365

Ser Gly Asn Tyr Cys Ser Asp Lys Pro Ala Ala Val Asn Trp Ile
        370                 375                 380

Glu Gly Arg Gly Lys Ser Val Val Cys Glu Ala Val Ile Pro Glu Glu
385                 390                 395                 400

Val Val Lys Lys Val Leu Lys Thr Asp Val Ala Ser Leu Val Glu Leu
                405                 410                 415

Asn Met Leu Lys Asn Leu Thr Gly Ser Ala Met Ala Gly Ala Leu Gly
                420                 425                 430

Gly Phe Asn Ala His Ala Ser Asn Ile Val Ser Ala Val Tyr Leu Ala
            435                 440                 445

Thr Gly Gln Asp Pro Ala Gln Asn Val Glu Ser
    450                 455

<210> SEQ ID NO 75
<211> LENGTH: 586
<212> TYPE: PRT
<213> ORGANISM: Lactuca sativa Lettuce

<400> SEQUENCE: 75

Met Asp Val Arg Arg Ser Ser Leu Lys Gln Ala Ala Thr Lys Gly
1               5                   10                  15

Lys Thr Met Ala Glu Asp Gln Tyr Asn Asp Gln Ile Phe Asn Lys Ala
                20                  25                  30

Thr Asp Lys Lys Val Val Asp Thr Val Val Pro Leu Pro Met Gly Ile
            35                  40                  45

Ser Asn Gly Val Phe Phe Thr Val Phe Phe Ser Val Val Tyr Phe Leu
        50                  55                  60

Leu Ile Arg Trp Arg Glu Lys Ile Arg Thr Ser Thr Pro Leu His Val
65                  70                  75                  80

Val Thr Met Ser Glu Met Ala Ala Ile Val Leu Phe Val Ala Ser Phe
                85                  90                  95

Ile Tyr Leu Leu Gly Phe Phe Gly Met Ser Phe Val Gln Ala Thr Pro
            100                 105                 110

Tyr Ser Asp Asp Glu Glu Glu Glu Leu Glu Val Asp Glu Thr Glu Met
            115                 120                 125

Val Arg Lys Glu Asp Thr Arg Thr Thr Pro Cys Gly Ala Ala Leu Asp
130                 135                 140

Cys Glu Ser Asp Val Val Val Lys Gln Val Val Lys Lys Glu Leu Val
145                 150                 155                 160

Phe Val Pro Thr Asp Thr Thr Val Thr Glu Glu Asp Glu Ile
                165                 170                 175

Ile Lys Ser Val Val Ser Gly Lys Thr Pro Ser Tyr Ser Leu Glu Thr
            180                 185                 190

Lys Leu Gly Asp Cys Lys Arg Ala Ala Phe Ile Arg Arg Val Ala Leu
        195                 200                 205

Glu Arg Ile Thr Gly Lys Ser Leu Asp Gly Leu Pro Leu Glu Gly Leu

```
                210                 215                 220
Asp Tyr Glu Ser Ile Leu Gly Gln Cys Cys Glu Met Pro Val Gly Tyr
225                 230                 235                 240

Val Gln Ile Pro Val Gly Val Cys Gly Pro Met Leu Leu Asn Gly Lys
                245                 250                 255

Glu Phe Ser Val Pro Met Ala Thr Thr Glu Gly Cys Leu Val Ala Ser
                260                 265                 270

Thr Asn Arg Gly Phe Lys Ala Ile Tyr Ala Ser Gly Gly Ala Thr Ala
                275                 280                 285

Ile Leu Leu Lys Asp Gly Met Thr Arg Ala Pro Val Val Arg Phe Gly
            290                 295                 300

Thr Ala Lys Arg Ala Ala Asp Leu Lys Phe Phe Leu Glu Glu Pro Leu
305                 310                 315                 320

Asn Phe Asp Thr Leu Ala Ser Val Phe Asn Lys Ser Ser Arg Phe Gly
                325                 330                 335

Arg Leu Gln Lys Ile Gln Cys Ala Ile Ala Gly Lys Asn Leu Tyr Ile
                340                 345                 350

Arg Phe Thr Cys Ser Thr Gly Asp Ala Met Gly Met Asn Met Val Ser
                355                 360                 365

Lys Gly Val Gln Asn Val Leu Glu Tyr Leu Gln Ala Asp Phe Pro Asp
            370                 375                 380

Met Asp Val Ile Gly Ile Ser Gly Asn Tyr Cys Ser Asp Lys Lys Pro
385                 390                 395                 400

Ala Ala Val Asn Trp Ile Glu Gly Arg Gly Lys Ser Val Val Cys Glu
                405                 410                 415

Ala Ile Ile Lys Glu Asp Val Val Lys Val Leu Lys Thr Asn Val
                420                 425                 430

Ala Ser Leu Val Glu Leu Asn Met Leu Lys Asn Leu Thr Gly Ser Ala
            435                 440                 445

Met Ala Gly Ala Leu Gly Gly Phe Asn Ala His Ala Ser Asn Ile Val
            450                 455                 460

Ser Ala Val Tyr Leu Ala Thr Gly Gln Asp Pro Ala Gln Asn Ile Glu
465                 470                 475                 480

Ser Ser His Cys Ile Thr Met Met Glu Ala Val Asn Asp Gly Lys Asp
                485                 490                 495

Leu His Val Ser Val Thr Met Pro Ser Ile Glu Val Gly Thr Val Gly
            500                 505                 510

Gly Gly Thr Gln Leu Ala Ser Gln Ala Ala Cys Leu Asn Leu Leu Gly
            515                 520                 525

Val Lys Gly Ala Asn Arg Glu Ser Pro Gly Thr Asn Ala Arg Gln Leu
            530                 535                 540

Ala Lys Val Val Ala Gly Ser Val Leu Ala Gly Glu Leu Ser Leu Leu
545                 550                 555                 560

Ser Ala Ile Ala Ala Gly Gln Leu Val Asn Ser His Met Lys Tyr Asn
                565                 570                 575

Arg Ser Gln Lys Asp Leu Thr Thr Lys Ala
            580                 585

<210> SEQ ID NO 76
<211> LENGTH: 438
<212> TYPE: PRT
<213> ORGANISM: Lactuca sativa Lettuce

<400> SEQUENCE: 76
```

```
Leu Thr Arg Thr Phe Ser Ala Ala Ala Pro Ser Val Leu Ala Phe Phe
1               5                   10                  15

Thr Ala Lys Met Asp Val Arg Arg Pro Val Lys Arg His Leu Gln
            20                  25                  30

Arg Ser Leu Lys Gln Gln Asp Ser Gly Glu Phe Leu Lys His Asn Asp
            35                  40                  45

Gln Ala Lys Ala Ser Asp Val Leu Pro Leu Pro Leu Tyr Leu Thr Asn
50                  55                  60

Gly Leu Phe Phe Thr Met Phe Phe Ser Val Met Tyr Phe Leu Leu Gln
65                  70                  75                  80

Arg Trp Arg Glu Lys Ile Arg Thr Ser Thr Pro Leu His Val Ala Thr
            85                  90                  95

Phe Ser Glu Met Ala Ala Leu Val Ser Leu Leu Ala Ser Phe Ile Tyr
            100                 105                 110

Leu Leu Gly Phe Phe Gly Phe Asp Phe Ile Lys Ser Ile Leu Arg Pro
            115                 120                 125

Ser Pro Ala Ser Trp Ile Ile Glu Asp Asp Asn Met Glu Glu Asp Lys
            130                 135                 140

Pro Val Lys Pro Cys Gly Gln Ala Leu Ile Pro His Ile Ser Pro Thr
145                 150                 155                 160

Asn Pro Thr Thr Glu Thr Glu Val Glu Arg Lys Lys Pro Pro Pro Thr
            165                 170                 175

Phe Glu Tyr Asn Ser Glu Glu Asn Glu Glu Ile Ile Lys Lys Val Val
            180                 185                 190

Ala Gly Ser Ile Pro Ser Tyr Ser Leu Glu Ser Asn Leu Gly Asp Cys
            195                 200                 205

Lys Arg Ala Ala Val Val Arg Arg Glu Ala Leu Glu Arg Ile Thr Gly
            210                 215                 220

Lys Ser Leu Ala Gly Met Pro Leu Glu Gly Phe Asp Tyr Glu Ser Ile
225                 230                 235                 240

Leu Gly Gln Cys Cys Glu Met Pro Val Gly Tyr Ile Gln Ile Pro Val
                245                 250                 255

Gly Ile Ala Gly Pro Leu Leu Leu Asn Gly Ala Glu Phe Ser Val Pro
            260                 265                 270

Met Ala Thr Thr Glu Gly Cys Leu Val Ala Ser Thr Asn Arg Gly Cys
            275                 280                 285

Lys Ala Ile Tyr Val Ser Gly Gly Ala Thr Cys Met Leu Leu Arg Asp
            290                 295                 300

Gly Met Thr Arg Ala Pro Val Val Arg Phe Gly Ser Ala Lys Arg Ala
305                 310                 315                 320

Ala Glu Leu Lys Leu Phe Leu Glu Asp Pro Glu Asn Phe Asp Thr Leu
            325                 330                 335

Ala Val Val Phe Asn Lys Ser Ser Arg Phe Gly Lys Leu Gln Ser Ile
            340                 345                 350

Lys Cys Ala Ile Ala Gly Lys Asn Leu Tyr Ile Arg Phe Cys Cys Ile
            355                 360                 365

Thr Gly Asp Ala Met Gly Met Asn Met Val Ser Lys Gly Val Gln Asn
370                 375                 380

Val Leu Asp Tyr Leu Gln Thr Asp Tyr Pro Asp Met Asp Val Met Gly
385                 390                 395                 400

Ile Ser Gly Asn Tyr Cys Ser Asp Lys Lys Pro Ala Ala Val Asn Trp
            405                 410                 415

Ile Glu Gly Arg Gly Lys Ser Val Val Cys Glu Ala Val Ile Asn Glu
```

```
                420                 425                 430
Glu Val Val Lys Lys Val
        435

<210> SEQ ID NO 77
<211> LENGTH: 301
<212> TYPE: PRT
<213> ORGANISM: Lactuca sativa Lettuce

<400> SEQUENCE: 77

Ala Leu Gln Arg Ile Thr Gly Lys Ser Leu Ser Gly Leu Pro Leu Glu
1               5                   10                  15

Gly Phe Asp Tyr Asp Ser Ile Leu Gly Gln Cys Cys Glu Met Pro Val
            20                  25                  30

Gly Tyr Ile Gln Ile Pro Val Gly Ile Ala Gly Pro Leu Leu Leu Asn
        35                  40                  45

Gly Ala Glu Phe Ser Val Pro Met Ala Thr Thr Glu Gly Cys Leu Val
    50                  55                  60

Ala Ser Thr Asn Arg Gly Cys Lys Ala Ile Tyr Val Ser Gly Gly Ala
65                  70                  75                  80

Thr Cys Met Leu Leu Lys Asp Gly Met Thr Arg Ala Pro Val Val Arg
                85                  90                  95

Phe Gly Ser Ala Lys Arg Ala Ala Glu Leu Lys Met Phe Leu Glu Asp
            100                 105                 110

Pro Leu Asn Phe Asp Thr Leu Ala Val Met Phe Asn Lys Ser Ser Arg
        115                 120                 125

Phe Gly Arg Leu Gln Ser Ile Arg Cys Ala Ile Ala Gly Lys Asn Leu
    130                 135                 140

Tyr Ile Arg Phe Cys Cys Ser Thr Gly Asp Ala Met Gly Met Asn Met
145                 150                 155                 160

Val Ser Lys Gly Val Gln Asn Val Leu Asp Phe Leu Gln Thr Asp Phe
                165                 170                 175

Pro Asp Met Asp Val Met Gly Ile Ser Gly Asn Tyr Cys Ser Asp Lys
            180                 185                 190

Lys Pro Ala Ala Val Asn Trp Ile Glu Gly Arg Gly Lys Ser Val Val
        195                 200                 205

Cys Glu Ala Val Ile Lys Glu Asp Val Val Gln Lys Val Leu Lys Thr
    210                 215                 220

Ser Val Ala Ser Leu Val Glu Leu Asn Met Leu Lys Asn Leu Thr Gly
225                 230                 235                 240

Ser Ala Met Ala Gly Ala Leu Gly Gly Phe Asn Ala His Ala Ser Asn
                245                 250                 255

Ile Val Ser Ala Val Tyr Leu Ala Thr Gly Gln Asp Pro Ala Gln Asn
            260                 265                 270

Val Glu Ser Ser His Cys Ile Thr Met Met Glu Ala Val Asn Gly Gly
        275                 280                 285

Lys Asp Leu His Val Ser Val Thr Met Pro Phe Ile Glu
    290                 295                 300

<210> SEQ ID NO 78
<211> LENGTH: 281
<212> TYPE: PRT
<213> ORGANISM: Lactuca sativa Lettuce

<400> SEQUENCE: 78

Arg Pro Tyr Gly Arg Leu Thr Gly Gly Cys Leu Val Ala Ser Thr Asn
```

```
            1               5                  10                 15
         Arg Gly Cys Lys Ala Ile Tyr Val Ser Gly Ala Thr Cys Met Leu
                        20                 25                 30

Leu Arg Asp Gly Met Thr Arg Ala Pro Val Val Arg Phe Gly Ser Ala
                        35                 40                 45

Lys Arg Ala Ala Glu Leu Lys Leu Phe Leu Glu Asp Pro Glu Asn Phe
                        50                 55                 60

Asp Thr Leu Ala Val Val Phe Asn Lys Ser Ser Arg Phe Gly Lys Leu
         65                 70                 75                 80

Gln Ser Ile Lys Cys Ala Ile Ala Gly Lys Asn Leu Tyr Ile Arg Phe
                        85                 90                 95

Cys Cys Ile Thr Gly Asp Ala Met Gly Met Asn Met Val Ser Lys Gly
                        100                105                110

Val Gln Asn Val Leu Asp Tyr Leu Gln Thr Asp Tyr Pro Asp Met Asp
                        115                120                125

Val Met Gly Ile Ser Gly Asn Tyr Cys Ser Asp Lys Lys Pro Ala Ala
                        130                135                140

Val Asn Trp Ile Glu Gly Arg Gly Lys Ser Val Val Cys Glu Ala Val
         145                150                155                160

Ile Asn Glu Glu Val Val Lys Lys Val Leu Lys Thr Thr Val Ala Ser
                        165                170                175

Leu Val Glu Leu Asn Met Val Lys Asn Leu Thr Gly Ser Ala Met Ala
                        180                185                190

Gly Ala Leu Gly Gly Phe Asn Ala His Ala Ser Asn Ile Val Ser Ala
                        195                200                205

Ile Tyr Ile Ala Thr Gly Gln Asp Pro Ala Gln Asn Val Glu Ser Ser
                        210                215                220

His Cys Ile Thr Met Met Glu Ala Ile Asn Asp Gly Lys Asp Leu His
         225                230                235                240

Val Ser Val Thr Met Pro Ser Ile Glu Val Gly Thr Val Gly Gly Gly
                        245                250                255

Thr Gln Leu Ala Ser Gln Ala Ala Cys Leu Asn Leu Leu Gly Val Lys
                        260                265                270

Val Gln Ala Lys Lys Asn Arg Val Glu
                        275                280

<210> SEQ ID NO 79
<211> LENGTH: 169
<212> TYPE: PRT
<213> ORGANISM: Lactuca sativa Lettuce

<400> SEQUENCE: 79

Glu Glu Ile Val Lys Lys Val Leu Lys Thr Thr Val His Gly Leu Val
         1               5                  10                 15

Glu Leu Asn Met Leu Lys Asn Leu Thr Gly Ser Ala Ile Ala Gly Ser
                        20                 25                 30

Leu Gly Gly Phe Asn Ala His Ala Ala Asn Ile Val Ser Ala Val Phe
                        35                 40                 45

Ile Ala Thr Gly Gln Asp Pro Ala Gln Asn Ile Glu Ser Ser His Cys
                        50                 55                 60

Ile Thr Met Met Glu Ala Val Asn Asn Gly Lys Asp Leu His Ile Ser
         65                 70                 75                 80

Val Thr Met Pro Ser Ile Glu Val Gly Thr Val Gly Gly Gly Thr Gln
                        85                 90                 95
```

```
Leu Ala Ser Gln Ser Ala Cys Leu Asn Leu Leu Gly Val Lys Gly Ala
                100                 105                 110

Ser Ile Gly Ser Pro Gly Ser Asn Ala Arg Leu Leu Ala Ser Val Val
            115                 120                 125

Ala Gly Ser Val Leu Ala Gly Glu Leu Ser Leu Met Ser Ala Ile Ala
        130                 135                 140

Ala Gly Gln Leu Val Lys Ser His Met Lys Tyr Asn Arg Ser Asn Arg
145                 150                 155                 160

Asp Met Ala Ala Ile Ala Ser Thr Val
                165

<210> SEQ ID NO 80
<211> LENGTH: 603
<212> TYPE: PRT
<213> ORGANISM: Manihot esculenta

<400> SEQUENCE: 80

Met Asp Ser Ser Arg Gln Pro Thr Ser Gly Lys Pro Met Asn Ser Asp
1               5                   10                  15

Asn Val Lys Ala Val Glu Asp Glu Asn Thr Gln Lys Pro Ser Asp Ala
            20                  25                  30

Leu Pro Leu His Leu Tyr Leu Thr Asn Ala Ile Cys Phe Thr Val Phe
        35                  40                  45

Phe Trp Val Val Tyr Phe Leu Leu Ser Arg Trp Arg Glu Lys Ile Arg
    50                  55                  60

Thr Ser Thr Pro Leu His Val Val Thr Leu Ser Glu Ile Ser Ala Ile
65                  70                  75                  80

Val Ala Leu Leu Ala Ser Phe Val Tyr Leu Leu Gly Phe Phe Gly Ile
                85                  90                  95

Asp Phe Val Gln Ser Leu Ile Leu Arg Pro Pro Thr Asp Leu Trp Thr
            100                 105                 110

Val Asp Asp Glu Asp Glu Glu Pro Ala Glu Arg Ile Leu Leu Gln Glu
        115                 120                 125

Asp Ala Arg Lys Leu Pro Cys Gly Gln Ala Leu Asp Cys Ser Leu Pro
130                 135                 140

Thr Pro Pro Leu Ser Arg Pro Ile Val Ser Ser Pro Lys Ala Val Gly
145                 150                 155                 160

Pro Ile Val Leu Pro Ser Pro Lys Pro Lys Val Phe Asp Glu Ile Pro
                165                 170                 175

Phe Pro Ala Thr Thr Tyr Leu Gly Glu Glu Asp Glu Glu Thr Ile Lys
            180                 185                 190

Ser Val Val Ala Gly Thr Ile Pro Ser Tyr Ser Leu Glu Ser Arg Leu
        195                 200                 205

Gly Asp Cys Lys Arg Ala Ala Ile Arg Arg Glu Ala Ser Gln Arg
210                 215                 220

Ile Thr Gly Lys Ser Leu Ser Gly Leu Pro Leu Glu Gly Phe Asp Tyr
225                 230                 235                 240

Glu Ser Ile Leu Gly Gln Cys Cys Glu Met Pro Val Gly Tyr Val Gln
                245                 250                 255

Ile Pro Val Gly Ile Ala Gly Pro Leu Leu Leu Asp Gly Lys Glu Phe
            260                 265                 270

Ser Val Pro Met Ala Thr Thr Glu Gly Cys Leu Val Ala Ser Thr Asn
        275                 280                 285

Arg Gly Cys Lys Ala Ile His Leu Ser Gly Gly Ala Thr Ser Val Leu
290                 295                 300
```

Leu Arg Asp Gly Met Thr Arg Ala Pro Val Val Arg Phe Ala Thr Ala
305                 310                 315                 320

Lys Arg Ala Ala Gln Leu Lys Leu Tyr Val Glu Asp His Ala Asn Phe
            325                 330                 335

Glu Thr Leu Ser Thr Val Phe Asn Lys Ser Ser Arg Phe Gly Arg Leu
        340                 345                 350

Gln Ser Ile Lys Cys Ala Ile Ala Gly Lys Asn Leu Tyr Met Arg Phe
    355                 360                 365

Cys Cys Ser Thr Gly Asp Ala Met Gly Met Asn Met Val Ser Lys Gly
370                 375                 380

Val Gln Asn Val Leu Asp Phe Leu Gln Asn Asp Phe Pro Asp Met Asp
385                 390                 395                 400

Val Ile Gly Leu Ser Gly Asn Phe Cys Ser Asp Lys Lys Pro Ala Ala
                405                 410                 415

Val Asn Trp Ile Glu Gly Arg Gly Lys Ser Val Val Cys Glu Ala Ile
            420                 425                 430

Ile Lys Gly Asp Val Val Lys Lys Val Leu Lys Thr Asn Val Asp Ala
        435                 440                 445

Leu Val Glu Leu Asn Met Leu Lys Asn Leu Thr Gly Ser Ala Met Ala
450                 455                 460

Gly Ala Leu Gly Gly Phe Asn Ala His Ala Gly Asn Ile Val Thr Ala
465                 470                 475                 480

Ile Tyr Ile Ala Thr Gly Gln Asp Pro Ala Gln Asn Val Glu Ser Ser
                485                 490                 495

His Cys Ile Thr Met Met Glu Ala Val Asn Asp Gly Gln Asp Leu His
            500                 505                 510

Val Ser Val Thr Met Pro Ser Ile Glu Val Gly Thr Val Gly Gly Gly
        515                 520                 525

Thr Gln Leu Ala Ser Gln Ser Ala Cys Leu Asn Leu Leu Gly Val Lys
530                 535                 540

Gly Ala Ser Lys Glu Thr Pro Gly Ala Asn Ser Arg Leu Leu Ala Ser
545                 550                 555                 560

Ile Val Ala Gly Ser Val Leu Ala Gly Glu Leu Ser Leu Met Ser Ala
                565                 570                 575

Ile Ser Ala Gly Gln Leu Val Lys Ser His Met Lys Tyr Asn Arg Ala
            580                 585                 590

Ser Lys Asp Ala Ala Val Ser Asn Pro Ser Lys
        595                 600

<210> SEQ ID NO 81
<211> LENGTH: 589
<212> TYPE: PRT
<213> ORGANISM: Manihot esculenta

<400> SEQUENCE: 81

Met Asp Ala Thr Ser Arg Pro Pro Lys Pro Cys Ser Thr Ala Thr
1               5                   10                  15

Gln Gly His Ile His His Arg Lys His Ala Ala Ser Val Glu Arg Arg
            20                  25                  30

Pro Ser Ser Pro Thr Pro Lys Ala Ser Asp Ala Leu Pro Leu Pro Leu
        35                  40                  45

Tyr Leu Thr Asn Ala Val Phe Phe Thr Leu Phe Phe Ser Val Ala Tyr
    50                  55                  60

Tyr Leu Leu His Arg Trp Arg Asp Lys Ile Arg Asn Ser Thr Pro Leu

```
            65                  70                  75                  80
        His Ile Val Thr Leu Ser Glu Ile Ala Ala Ile Val Ser Leu Ile Ala
                        85                  90                  95

Ser Phe Ile Tyr Leu Leu Gly Phe Gly Ile Asp Phe Val Gln Ser
                        100                 105                 110

Phe Ile Ala Arg Ala Ser His Glu Ala Trp Asp Leu Asp Thr Asp
                        115                 120                 125

Pro Asn Tyr Leu Ile Asp Glu Asp His Arg Leu Ile Thr Cys Pro Pro
        130                     135                 140

Ala Ser Ile Ser Thr Lys Thr Asn Leu Ala Ser Ala Ala Pro Lys Leu
        145                     150                 155                 160

Pro Thr Ser Val Pro Leu Ile Thr Ser Leu Ala Ser Glu Glu Asp Glu
                        165                 170                 175

Met Ile Val Asn Ser Val Val Asn Gly Ile Ile Pro Tyr Ser Leu
                        180                 185                 190

Glu Ser Lys Leu Gly Asp Cys Lys Arg Ala Ala Val Ile Arg Arg Glu
                        195                 200                 205

Ala Leu Gln Arg Met Thr Gly Arg Ser Leu Gly Gly Leu Pro Leu Glu
        210                     215                 220

Gly Phe Asp Tyr Glu Ser Ile Leu Gly Gln Cys Cys Glu Met Pro Val
        225                     230                 235                 240

Gly Tyr Val Gln Ile Pro Val Gly Ile Ala Gly Pro Leu Leu Leu Asn
                        245                 250                 255

Gly Arg Glu Tyr Ser Val Pro Met Ala Thr Thr Glu Gly Cys Leu Val
                        260                 265                 270

Ala Ser Thr Asn Arg Gly Cys Lys Ala Ile Tyr Leu Ser Gly Gly Ser
                        275                 280                 285

Thr Ser Val Leu Leu Lys Asp Gly Met Thr Arg Ala Pro Val Val Arg
                        290                 295                 300

Phe Ala Thr Ala Thr Arg Ala Ala Glu Leu Lys Phe Phe Leu Glu Asp
        305                     310                 315                 320

Pro Asp Asn Phe Asp Thr Leu Ala Val Val Phe Asn Arg Ser Ser Arg
                        325                 330                 335

Phe Ala Arg Leu Gln Gly Ile Gln Cys Ser Ile Ala Gly Lys Asn Leu
                        340                 345                 350

Tyr Met Arg Phe Ser Cys Ser Thr Gly Asp Ala Met Gly Met Asn Met
                        355                 360                 365

Val Ser Lys Gly Val Gln Asn Val Leu Glu Phe Leu Gln Asn Asp Phe
                        370                 375                 380

Ser Asp Met Asp Val Ile Gly Ile Ser Gly Asn Phe Cys Ser Asp Lys
        385                     390                 395                 400

Lys Pro Ala Ala Val Asn Trp Ile Glu Gly Arg Gly Lys Ser Val Val
                        405                 410                 415

Cys Glu Ala Ile Ile Lys Glu Glu Val Val Lys Lys Val Leu Lys Thr
                        420                 425                 430

Lys Val Ala Ser Leu Val Glu Leu Asn Met Leu Lys Asn Leu Ala Gly
                        435                 440                 445

Ser Ala Ile Ala Gly Ala Leu Gly Gly Phe Asn Ala His Ala Gly Asn
                        450                 455                 460

Ile Val Ser Ala Ile Phe Ile Ala Thr Gly Gln Asp Pro Ala Gln Asn
        465                     470                 475                 480

Val Glu Ser Ser His Cys Ile Thr Met Met Glu Ala Val Asn Asp Gly
                        485                 490                 495
```

```
Lys Asp Leu His Ile Ser Val Thr Met Pro Ser Ile Glu Val Gly Thr
                500                 505                 510

Val Gly Gly Gly Thr Gln Leu Ala Ser Gln Ser Ala Cys Leu Asn Leu
            515                 520                 525

Leu Gly Val Lys Gly Ala Ser Glu Glu Ser Pro Gly Ser Asn Ser Arg
530                 535                 540

Leu Leu Ala Thr Ile Val Ala Gly Ser Val Leu Ala Gly Glu Leu Ser
545                 550                 555                 560

Leu Met Ser Ala Ile Ala Ala Gly Gln Leu Val Arg Ser His Met Lys
                565                 570                 575

Tyr Asn Arg Ser Ser Lys Asp Val Ser Lys Ala Ala Ser
                580                 585

<210> SEQ ID NO 82
<211> LENGTH: 590
<212> TYPE: PRT
<213> ORGANISM: Eucommia ulmoides

<400> SEQUENCE: 82

Met Asp Leu Arg Arg Pro Pro Lys Pro Ala Ala Thr Asn Gly Arg
1               5                   10                  15

Asn His His Leu His His Gln Gly Asn Ser Ser Pro Ala Ile Asp
                20                  25                  30

Cys Ser Pro Ser Pro Ile Pro Lys Ala Ser Asp Ala Leu Pro Leu Pro
                35                  40                  45

Leu Tyr Leu Thr Asn Gly Ile Phe Phe Thr Leu Phe Phe Ser Val Ala
50                  55                  60

Tyr Tyr Leu Leu His Arg Trp Arg Asp Lys Ile Arg Asn Ser Thr Pro
65                  70                  75                  80

Leu His Val Leu Thr Leu Ser Glu Leu Ala Ala Ile Val Ser Leu Ile
                85                  90                  95

Ala Ser Phe Ile Tyr Leu Leu Gly Phe Phe Gly Ile Asp Phe Val Gln
                100                 105                 110

Ser Phe Ile Ala Arg Ala Ser His Asp Pro Trp Asp Val Asp Asp Asp
                115                 120                 125

Glu Arg Phe Ile Leu Glu Glu Asp Arg Arg Gly Pro Cys Thr Ala
                130                 135                 140

Ala Leu Asp Cys Leu Val Gly Pro Val Ala Pro Ser Ile Ser Asp Val
145                 150                 155                 160

Arg Lys Leu Met Asp Pro Pro Ala Pro Leu Pro Ser Val Glu Asp Glu
                165                 170                 175

Gln Met Val Lys Ser Val Ile Ser Gly Thr Val Pro Ser Tyr Ser Leu
                180                 185                 190

Glu Ser Lys Leu Gly Asp Cys Tyr Arg Ala Ala Ser Ile Arg Arg Glu
                195                 200                 205

Ala Ile Gln Arg Ile Thr Gly Lys Ser Leu Ser Gly Leu Pro Leu Glu
            210                 215                 220

Gly Phe Asp Tyr Glu Ala Ile Leu Gly Gln Cys Cys Glu Met Pro Ile
225                 230                 235                 240

Gly Phe Leu Gln Ile Pro Val Gly Ile Ala Gly Pro Leu Leu Leu Asn
                245                 250                 255

Gly Cys Glu Tyr Ser Val Pro Met Ala Thr Thr Glu Gly Cys Leu Val
                260                 265                 270

Ala Ser Thr Asn Arg Gly Cys Lys Ala Ile Tyr Ala Ser Gly Gly Ala
```

```
              275                 280                 285
Thr Ser Ile Leu Leu Arg Asp Gly Met Thr Arg Ala Pro Val Val Arg
290                 295                 300
Phe Pro Ser Ala Lys Arg Ala Ser Glu Leu Lys Phe Phe Leu Glu Asp
305                 310                 315                 320
Pro Leu Asn Phe Glu Thr Leu Ser Met Val Phe Asn Lys Ser Ser Arg
              325                 330                 335
Phe Ala Arg Leu Gln Gly Ile Gln Cys Ser Ile Ala Gly Lys Asn Leu
              340                 345                 350
Tyr Met Arg Phe Thr Cys Ser Thr Gly Asp Ala Met Gly Met Asn Met
              355                 360                 365
Val Ser Lys Gly Val Gln Asn Ile Leu Glu Phe Leu Gln Asn Asp Phe
370                 375                 380
Pro Asp Met Asp Val Ile Gly Ile Ser Gly Asn Phe Cys Ser Asp Lys
385                 390                 395                 400
Lys Pro Ala Ala Val Asn Trp Ile Glu Gly Arg Gly Lys Ser Val Val
              405                 410                 415
Cys Glu Ala Ile Ile Ser Glu Asp Ile Val Arg Lys Val Leu Lys Thr
              420                 425                 430
Thr Val Pro Ala Leu Val Glu Leu Asn Met Leu Lys Asn Leu Ala Gly
              435                 440                 445
Ser Ala Val Ala Gly Ala Leu Gly Gly Phe Asn Ala His Ala Ala Asn
450                 455                 460
Ile Val Ser Ala Val Phe Ile Ala Thr Gly Gln Asp Pro Ala Gln Asn
465                 470                 475                 480
Ile Glu Ser Ser His Cys Ile Thr Met Met Glu Ala Val Asn Asp Gly
              485                 490                 495
Lys Asp Leu His Ile Ser Val Thr Met Pro Ser Ile Glu Val Gly Thr
              500                 505                 510
Val Gly Gly Gly Thr Gln Leu Ala Ser Gln Ser Ala Cys Leu Asn Leu
              515                 520                 525
Leu Gly Val Lys Gly Ala Asn Lys Glu Ser Pro Gly Ser Asn Ser Arg
530                 535                 540
Leu Leu Ala Ala Ile Val Ala Gly Ser Val Leu Ala Gly Glu Leu Ser
545                 550                 555                 560
Leu Met Ser Ala Ile Ala Ala Gly Gln Leu Val Asn Ser His Met Lys
              565                 570                 575
Tyr Asn Arg Ser Asn Arg Asp Phe Thr Lys Val Thr Ser Ser
              580                 585                 590

<210> SEQ ID NO 83
<211> LENGTH: 583
<212> TYPE: PRT
<213> ORGANISM: Euphorbia helioscopia L.

<400> SEQUENCE: 83

Met Asp Ser Thr Lys Ser Arg Arg Pro Ile Arg His Leu His His Gln
1               5                  10                  15
Lys Arg Ile Ser Glu Glu Val Asp Asp His Arg Cys Leu Ser Pro Pro
              20                  25                  30
Leu Lys Ala Ser Asp Ala Leu Pro Leu Pro Leu Tyr Leu Thr Asn Ala
              35                  40                  45
Val Phe Phe Thr Leu Phe Phe Ser Val Ala Tyr Tyr Leu Leu His Arg
50                  55                  60
```

```
Trp Arg Asp Lys Ile Arg Asn Ser Thr Pro Leu His Val Val Thr Leu
 65                  70                  75                  80

Ser Glu Ile Ala Ala Ile Val Ser Leu Ile Ala Ser Phe Ile Tyr Leu
             85                   90                  95

Leu Gly Phe Phe Gly Ile Gly Phe Val Gln Ser Leu Ile Ala Arg Pro
            100                 105                 110

Ser His Asp Thr Trp Asp Leu Asp Asp Ala Asp Arg Ser Tyr Leu Ile
            115                 120                 125

Asp Gly Asp His Arg Leu Val Thr Cys Ser Pro Ala Lys Val Ala Pro
        130                 135                 140

Val Asn Ser Pro Pro Pro Ala Lys Met Ser Val Pro Glu Pro Ile Val
145                 150                 155                 160

Ser Pro Leu Ala Ser Glu Glu Asp Glu Glu Ile Val Lys Ser Val Val
            165                 170                 175

Asn Gly Thr Ile Pro Ser Tyr Ser Leu Glu Ser Lys Leu Gly Asp Cys
            180                 185                 190

Lys Arg Ala Ala Glu Ile Arg Arg Glu Ala Leu Gln Arg Met Thr Gly
            195                 200                 205

Arg Ser Leu Glu Gly Leu Pro Val Gly Phe Asp Tyr Glu Ser Ile
210                 215                 220

Leu Gly Gln Cys Cys Glu Met Pro Val Gly Tyr Val Gln Ile Pro Val
225                 230                 235                 240

Gly Ile Ala Gly Pro Leu Leu Leu Asp Gly Arg Glu Tyr Ser Val Pro
                245                 250                 255

Met Ala Thr Thr Glu Gly Cys Leu Val Ala Ser Thr Asn Arg Gly Cys
                260                 265                 270

Lys Ala Ile His Leu Ser Gly Gly Ala Asp Ser Val Leu Leu Lys Asp
            275                 280                 285

Gly Met Thr Arg Ala Pro Val Val Arg Phe Thr Ser Val Arg Arg Ala
            290                 295                 300

Ala Glu Leu Lys Phe Phe Leu Glu Ser Pro Glu Asn Phe Asp Ser Leu
305                 310                 315                 320

Ser Val Val Phe Asn Arg Ser Ser Gly Phe Ala Lys Leu Leu Asn Ile
                325                 330                 335

Gln Cys Thr Leu Ala Gly Arg Asn Leu Tyr Met Arg Phe Thr Cys Phe
            340                 345                 350

Thr Gly Asp Ala Met Gly Met Asn Met Val Ser Lys Gly Val Gln Asn
            355                 360                 365

Val Leu Glu Phe Leu Gln Ser Asp Phe Pro Asp Met Asp Val Leu Gly
            370                 375                 380

Ile Ser Gly Asn Tyr Cys Ser Asp Lys Lys Pro Ala Ala Val Asn Trp
385                 390                 395                 400

Ile Glu Gly Arg Gly Lys Trp Val Val Cys Glu Ala Ile Ile Lys Glu
                405                 410                 415

Glu Val Val Lys Lys Val Leu Lys Thr Ser Val Ala Ala Leu Val Glu
                420                 425                 430

Leu Asn Met Val Lys Asn Leu Ala Gly Ser Ala Val Ala Gly Ser Leu
            435                 440                 445

Gly Gly Phe Asn Ala His Ala Ala Asn Ile Val Ser Ala Val Phe Ile
            450                 455                 460

Ala Thr Gly Gln Asp Pro Ala Gln Asn Val Glu Ser Ser His Cys Met
465                 470                 475                 480

Thr Met Met Glu Ala Val Asn Asp Gly Lys Asp Leu His Ile Ser Val
```

```
                        485                 490                 495
Thr Met Pro Ser Ile Glu Val Gly Thr Val Gly Gly Gly Thr Gln Leu
            500                 505                 510

Ala Ser Gln Ser Ala Cys Leu Asn Leu Leu Gly Val Lys Gly Ala Asn
            515                 520                 525

Lys Glu Ser Pro Gly Ala Asn Ala Arg Gln Leu Ala Thr Ile Val Ala
            530                 535                 540

Gly Ser Val Leu Ala Gly Glu Leu Ser Leu Met Ser Ala Ile Ala Ala
545                 550                 555                 560

Gly Gln Leu Val Lys Ser His Leu Lys Tyr Asn Arg Ser Ser Lys Asp
                565                 570                 575

Val Ser Ser Phe Ala Ser Ser
            580

<210> SEQ ID NO 84
<211> LENGTH: 532
<212> TYPE: PRT
<213> ORGANISM: Oryza sativa

<400> SEQUENCE: 84

Met Asp Val Arg Arg Gly Gly Gly Gly Arg Ile Val Gly Ala Ala
1               5                   10                  15

Arg Arg Ala Leu Thr Trp Gly Ala Leu Pro Leu Pro Met Arg Ile Thr
                20                  25                  30

Asn Gly Leu Ala Met Val Ser Leu Val Leu Ser Ser Cys Asp Leu Leu
            35                  40                  45

Arg Leu Cys Ser Asp Arg Glu Arg Pro Leu Gly Gly Arg Glu Phe Ala
50                  55                  60

Thr Val Val Tyr Leu Val Ser Leu Phe Ala His Pro Asp Ala Pro Ala
65                  70                  75                  80

Thr Thr Thr Gly Asp Asp Asp Gly Gln Gly Gly Ser Arg Arg Ala
                85                  90                  95

Arg Pro Ala Ala Ala Glu Pro Ala Pro Met His Gly His Gly Gly Gly
                100                 105                 110

Met Met Glu Ala Asp Asp Glu Glu Ile Val Ala Ala Val Ala Ser Gly
            115                 120                 125

Ala Leu Pro Ser His Arg Leu Glu Ser Arg Leu Gly Asp Cys Arg Arg
            130                 135                 140

Ala Ala Arg Leu Arg Arg Glu Ala Leu Arg Arg Val Thr Gly Arg Gly
145                 150                 155                 160

Val Glu Gly Leu Pro Phe Asp Gly Met Asp Tyr Gln Ala Ile Leu Gly
                165                 170                 175

Gln Cys Cys Glu Met Pro Val Gly Tyr Val Gln Leu Pro Val Gly Val
            180                 185                 190

Ala Gly Pro Leu Leu Leu Asp Gly Arg Glu Tyr His Val Pro Met Ala
            195                 200                 205

Thr Thr Glu Gly Cys Leu Val Ala Ser Val Asn Arg Gly Cys Arg Ala
            210                 215                 220

Ile Ser Ala Ser Gly Gly Ala Phe Ser Val Leu Leu Arg Asp Ala Met
225                 230                 235                 240

Ser Arg Ala Pro Ala Val Lys Leu Pro Ser Ala Met Arg Ala Ala Glu
                245                 250                 255

Leu Lys Ala Phe Ala Glu Ala Pro Ala Asn Phe Glu Leu Leu Ala Ala
            260                 265                 270
```

```
Val Phe Asn Arg Ser Ser Arg Phe Gly Arg Leu Gln Asp Ile Arg Cys
            275                 280                 285

Ala Leu Ala Gly Arg Asn Leu Tyr Met Arg Phe Ser Cys Ile Thr Gly
290                 295                 300

Asp Ala Met Gly Met Asn Met Val Ser Lys Gly Val Glu Asn Val Leu
305                 310                 315                 320

Gly Tyr Leu Gln Asn Val Phe Pro Asp Met Asp Val Ile Ser Val Ser
                325                 330                 335

Gly Asn Tyr Cys Ser Asp Lys Lys Pro Thr Ala Val Asn Trp Ile Glu
            340                 345                 350

Gly Arg Gly Lys Ser Val Val Cys Glu Ala Ile Ile Lys Gly Asp Val
            355                 360                 365

Val Gln Lys Val Leu Lys Thr Thr Val Glu Lys Leu Val Glu Leu Asn
370                 375                 380

Ile Ile Lys Asn Leu Ala Gly Ser Ala Val Ala Gly Ala Leu Gly Gly
385                 390                 395                 400

Phe Asn Ala His Ala Ser Asn Ile Val Thr Ala Leu Phe Ile Ala Thr
                405                 410                 415

Gly Gln Asp Pro Ala Gln Asn Val Glu Ser Ser Gln Cys Ile Thr Met
            420                 425                 430

Leu Glu Glu Val Asn Asp Gly Asp Asp Leu His Ile Ser Val Thr Met
435                 440                 445

Pro Ser Ile Glu Val Gly Thr Ile Gly Gly Gly Thr Cys Leu Ala Ser
            450                 455                 460

Gln Ala Ala Cys Leu Asn Leu Leu Gly Val Lys Gly Ser Asn His Gly
465                 470                 475                 480

Ser Pro Gly Ala Asn Ala Lys Arg Leu Ala Thr Ile Val Ala Gly Ser
                485                 490                 495

Val Leu Ala Gly Glu Leu Ser Leu Leu Ala Leu Ala Ser Gly His
            500                 505                 510

Leu Val Lys Ser His Met Met Tyr Asn Arg Ser Ser Lys Asp Val Ala
            515                 520                 525

Lys Ala Ala Ser
    530

<210> SEQ ID NO 85
<211> LENGTH: 596
<212> TYPE: PRT
<213> ORGANISM: Solanum tuberosum L.

<400> SEQUENCE: 85

Met Asp Val Arg Arg Arg Pro Val Lys Pro Leu Tyr Thr Ser Lys Asp
1               5                   10                  15

Ala Ser Ala Gly Glu Pro Leu Lys Gln Gln Glu Val Ser Ser Pro Lys
            20                  25                  30

Ala Ser Asp Ala Leu Pro Leu Pro Leu Tyr Leu Thr Asn Gly Leu Phe
        35                  40                  45

Phe Thr Met Phe Phe Ser Val Met Tyr Phe Leu Leu Val Arg Trp Arg
    50                  55                  60

Glu Lys Ile Arg Asn Ser Ile Pro Leu His Val Val Thr Leu Ser Glu
65                  70                  75                  80

Leu Leu Ala Met Val Ser Leu Ile Ala Ser Val Ile Tyr Leu Leu Gly
                85                  90                  95

Phe Phe Gly Ile Gly Phe Val Gln Ser Phe Val Ser Arg Ser Asn Ser
            100                 105                 110
```

```
Asp Ser Trp Asp Ile Glu Asp Glu Asn Ala Glu Gln Leu Ile Ile Glu
        115                 120                 125

Glu Asp Ser Arg Arg Gly Pro Cys Ala Ala Ala Thr Thr Leu Gly Cys
        130                 135                 140

Val Val Pro Pro Pro Val Arg Lys Ile Ala Pro Met Val Pro Gln
145                 150                 155                 160

Gln Pro Ala Lys Val Ala Leu Ser Gln Thr Glu Lys Pro Ser Pro Ile
                165                 170                 175

Ile Met Pro Ala Leu Ser Glu Asp Asp Glu Glu Ile Ile Gln Ser Val
            180                 185                 190

Val Gln Gly Lys Thr Pro Ser Tyr Ser Leu Glu Ser Lys Leu Gly Asp
        195                 200                 205

Cys Met Arg Ala Ala Ser Ile Arg Lys Glu Ala Leu Gln Arg Ile Thr
    210                 215                 220

Gly Lys Ser Leu Glu Gly Leu Pro Leu Glu Gly Phe Asp Tyr Ser Ser
225                 230                 235                 240

Ile Leu Gly Gln Cys Cys Glu Met Pro Val Gly Tyr Val Gln Ile Pro
                245                 250                 255

Val Gly Ile Ala Gly Pro Leu Leu Leu Asp Gly Arg Glu Tyr Ser Val
            260                 265                 270

Pro Met Ala Thr Thr Glu Gly Cys Leu Val Ala Ser Thr Asn Arg Gly
        275                 280                 285

Cys Lys Ala Ile Phe Val Ser Gly Gly Ala Asp Ser Val Leu Leu Arg
    290                 295                 300

Asp Gly Met Thr Arg Ala Pro Val Val Arg Phe Thr Thr Ala Lys Arg
305                 310                 315                 320

Ala Ala Glu Leu Lys Phe Phe Val Glu Asp Pro Leu Asn Phe Glu Thr
                325                 330                 335

Leu Ser Leu Met Phe Asn Lys Ser Ser Arg Phe Ala Arg Leu Gln Gly
            340                 345                 350

Ile Gln Cys Ala Ile Ala Gly Lys Asn Leu Tyr Ile Thr Phe Ser Cys
        355                 360                 365

Ser Thr Gly Asp Ala Met Gly Met Asn Met Val Ser Lys Gly Val Gln
    370                 375                 380

Asn Val Leu Asp Tyr Leu Gln Ser Glu Tyr Pro Asp Met Asp Val Ile
385                 390                 395                 400

Gly Ile Ser Gly Asn Phe Cys Ser Asp Lys Lys Pro Ala Ala Val Asn
                405                 410                 415

Trp Ile Glu Gly Arg Gly Lys Ser Val Val Cys Glu Ala Ile Ile Lys
            420                 425                 430

Glu Glu Val Val Lys Lys Val Leu Lys Thr Glu Val Ala Ala Leu Val
        435                 440                 445

Glu Leu Asn Met Leu Lys Asn Leu Thr Gly Ser Ala Met Ala Gly Ala
    450                 455                 460

Leu Gly Gly Phe Asn Ala His Ala Ser Asn Ile Val Ser Ala Val Tyr
465                 470                 475                 480

Leu Ala Thr Gly Gln Asp Pro Ala Gln Asn Val Glu Ser Ser His Cys
                485                 490                 495

Ile Thr Met Met Glu Ala Val Asn Asp Gly Lys Asp Leu His Val Ser
            500                 505                 510

Val Thr Met Pro Ser Ile Glu Val Gly Thr Val Gly Gly Gly Thr Gln
        515                 520                 525
```

```
Leu Ala Ser Gln Ser Ala Cys Leu Asn Leu Leu Gly Val Lys Gly Ala
            530                 535                 540

Asn Arg Asp Ala Pro Gly Ser Asn Ala Arg Leu Leu Ala Thr Ile Val
545                 550                 555                 560

Ala Gly Ser Val Leu Ala Gly Glu Leu Ser Leu Met Ser Ala Ile Ser
                565                 570                 575

Ala Gly Gln Leu Val Lys Ser His Met Lys Tyr Asn Arg Ser Ile Lys
            580                 585                 590

Asp Ile Ser Lys
        595

<210> SEQ ID NO 86
<211> LENGTH: 595
<212> TYPE: PRT
<213> ORGANISM: Solanum tuberosum L.

<400> SEQUENCE: 86

Met Asp Val Arg Arg Ser Glu Lys Pro Val Tyr Pro Ser Lys Val
1               5                   10                  15

Phe Gly Ala Asp Glu Lys Pro Leu Lys Pro His Asn Asn Gln Gln Gln
            20                  25                  30

Glu Asp Asn Asn Thr Leu Leu Ile Asp Ala Ser Asp Ala Leu Pro Leu
        35                  40                  45

Pro Leu Tyr Leu Thr Asn Gly Leu Phe Phe Thr Met Phe Phe Ser Val
    50                  55                  60

Met Tyr Phe Leu Leu Ser Arg Trp Arg Glu Lys Ile Arg Asn Ser Thr
65                  70                  75                  80

Pro Leu His Val Val Thr Leu Ser Glu Leu Gly Ala Ile Val Ser Leu
                85                  90                  95

Ile Ala Ser Val Ile Tyr Leu Leu Gly Phe Phe Gly Ile Gly Phe Val
            100                 105                 110

Gln Thr Phe Val Ser Arg Gly Asn Asn Asp Ser Trp Asp Glu Asn Asp
        115                 120                 125

Glu Glu Phe Leu Leu Lys Glu Asp Ser Arg Cys Gly Pro Ala Thr Thr
    130                 135                 140

Leu Gly Cys Ala Ile Pro Ala Pro Pro Ala Arg Gln Ile Ser Pro Met
145                 150                 155                 160

Ala Pro Pro Gln Pro Ala Met Ser Met Val Glu Lys Pro Ser Pro Leu
                165                 170                 175

Ile Thr Pro Ala Ser Ser Glu Glu Asp Glu Glu Ile Ile Asn Ser Val
            180                 185                 190

Val Gln Gly Lys Phe Pro Ser Tyr Ser Leu Val Ile Gln Leu Gly Asp
        195                 200                 205

Val Ser Ala Ala Ala Ser Leu Arg Lys Glu Val Met Gln Arg Ile Thr
    210                 215                 220

Gly Lys Ser Leu Glu Gly Leu Pro Leu Glu Gly Phe Thr Tyr Glu Ser
225                 230                 235                 240

Ile Leu Gly Gln Cys Cys Glu Met Pro Ile Gly Tyr Val Gln Ile Pro
                245                 250                 255

Val Gly Ile Ala Gly Pro Leu Leu Asn Gly Lys Glu Phe Ser Val
            260                 265                 270

Pro Met Ala Thr Thr Glu Gly Cys Leu Val Ala Ser Thr Asn Arg Gly
        275                 280                 285

Cys Lys Ala Ile Tyr Ala Ser Gly Gly Ala Thr Cys Ile Val Leu Arg
    290                 295                 300
```

Asp Gly Met Thr Arg Ala Pro Cys Val Arg Phe Gly Thr Ala Lys Arg
305                 310                 315                 320

Ala Ala Glu Leu Lys Phe Phe Val Glu Asp Pro Ile Lys Phe Glu Thr
            325                 330                 335

Leu Ala Asn Val Phe Asn Gln Ser Ser Arg Phe Gly Arg Leu Gln Arg
        340                 345                 350

Ile Gln Cys Ala Ile Ala Gly Lys Asn Leu Tyr Met Arg Phe Val Cys
        355                 360                 365

Ser Thr Gly Asp Ala Met Gly Met Asn Met Val Ser Lys Gly Val Gln
370                 375                 380

Asn Val Leu Asp Tyr Leu Gln Asn Glu Tyr Pro Asp Met Asp Val Ile
385                 390                 395                 400

Gly Ile Ser Gly Asn Phe Cys Ser Asp Lys Lys Pro Ala Ala Val Asn
            405                 410                 415

Trp Ile Glu Gly Arg Gly Lys Ser Val Val Cys Glu Ala Ile Ile Thr
            420                 425                 430

Glu Glu Val Val Lys Lys Val Leu Lys Thr Glu Val Ala Ala Leu Val
        435                 440                 445

Glu Leu Asn Met Leu Lys Asn Leu Thr Gly Ser Ala Met Ala Gly Ala
450                 455                 460

Leu Gly Gly Phe Asn Ala His Ala Ser Asn Ile Val Ser Ala Val Phe
465                 470                 475                 480

Ile Ala Thr Gly Gln Asp Pro Ala Gln Asn Ile Glu Ser Ser His Cys
            485                 490                 495

Ile Thr Met Met Glu Ala Val Asn Asp Gly Lys Asp Leu His Ile Ser
            500                 505                 510

Val Thr Met Pro Ser Ile Glu Val Gly Thr Val Gly Gly Gly Thr Gln
        515                 520                 525

Leu Ala Ser Gln Ser Ala Cys Leu Asn Leu Leu Gly Val Lys Gly Ala
530                 535                 540

Asn Arg Glu Ala Pro Gly Ser Asn Ala Arg Leu Leu Ala Thr Val Val
545                 550                 555                 560

Ala Gly Ser Val Leu Ala Gly Glu Leu Ser Leu Met Ser Ala Ile Ser
            565                 570                 575

Ala Gly Gln Leu Val Asn Ser His Met Lys Tyr Asn Arg Ser Thr Lys
        580                 585                 590

Ala Ser Ser
        595

<210> SEQ ID NO 87
<211> LENGTH: 574
<212> TYPE: PRT
<213> ORGANISM: Solanum tuberosum L.

<400> SEQUENCE: 87

Met Asp Val Arg Arg Pro Val Lys Pro Leu Tyr Pro Ser Glu His
1               5                   10                  15

Ile Ser Ser Gly Glu Pro Leu Lys Pro His Asn Gln Asp Ser Val
                20                  25                  30

Lys Ala Ser Asp Ala Leu Pro Leu Pro Leu Tyr Leu Thr Asn Gly Leu
            35                  40                  45

Phe Phe Thr Met Phe Phe Ser Val Met Tyr Phe Leu Leu His Arg Trp
        50                  55                  60

Arg Glu Lys Ile Arg Asn Gly Ile Pro Leu His Val Leu Asn Phe Ser

-continued

```
                65                  70                  75                  80
        Glu Leu Val Ala Met Val Ser Leu Ile Ala Ser Val Ile Tyr Leu Leu
                            85                  90                  95
        Gly Phe Phe Gly Ile Gly Phe Val Gln Ser Phe Val Ser Lys Gly Asn
                           100                 105                 110
        Asn Asp Ser Trp Asp Val Glu Glu Ser Pro Glu Gln Phe Ile Asp
                   115                 120                 125
        Arg Thr Val Thr Pro Pro Val Arg Arg Asn Ile Pro Met Lys Ser
            130                 135                 140
        Val Pro Val Ala Glu Lys Thr Ala Gln Ile Ile Thr Pro Phe Ser Ser
        145                 150                 155                 160
        Glu Asp Asp Glu Val Val Ile Lys Ser Val Val Gly Arg Ile Pro
                        165                 170                 175
        Ser Tyr Ser Leu Glu Ser Lys Leu Gly Asp Cys Lys Arg Ala Ala Phe
                        180                 185                 190
        Ile Arg Lys Glu Ala Leu Gln Arg Ser Ser Gly Lys Ser Leu Glu Gly
                        195                 200                 205
        Leu Pro Leu Asp Gly Phe Asp Tyr Glu Ser Ile Leu Gly Gln Cys Cys
            210                 215                 220
        Glu Met Pro Ile Gly Tyr Ile Gln Ile Pro Val Gly Ile Ala Gly Pro
        225                 230                 235                 240
        Leu Leu Leu Asn Gly Lys Glu Phe Ser Val Pro Met Ala Thr Thr Glu
                        245                 250                 255
        Gly Cys Leu Val Ala Ser Thr Asn Arg Gly Cys Lys Ala Ile Tyr Val
                        260                 265                 270
        Ser Gly Gly Ala Thr Ser Val Leu Phe Arg Asp Ala Met Thr Arg Ala
                    275                 280                 285
        Pro Val Val Arg Phe Gly Ser Ala Lys Arg Ala Ala Glu Leu Lys Phe
            290                 295                 300
        Phe Val Glu Asp Pro Met Asn Phe Glu Thr Leu Ser Val Val Phe Asn
        305                 310                 315                 320
        Lys Ser Ser Arg Phe Ala Arg Leu Gln Asn Ile Gln Cys Ala Ile Ala
                        325                 330                 335
        Gly Lys Asn Leu Tyr Met Arg Phe Ser Cys Ser Thr Gly Asp Ala Met
                        340                 345                 350
        Gly Met Asn Met Val Ser Lys Gly Val Gln Asn Val Leu Asp Tyr Leu
                    355                 360                 365
        Gln Asn Glu Tyr Pro Asp Met Asp Ile Ile Gly Ile Ser Gly Asn Tyr
            370                 375                 380
        Cys Ser Asp Lys Lys Pro Ala Ala Val Asn Trp Ile Glu Gly Arg Gly
        385                 390                 395                 400
        Lys Ser Val Val Cys Glu Ala Ile Ile Lys Glu Asp Val Val Lys Lys
                        405                 410                 415
        Val Leu Lys Thr Glu Val Ala Thr Leu Val Glu Leu Asn Met Leu Lys
                    420                 425                 430
        Asn Leu Thr Gly Ser Ala Met Ala Gly Ala Leu Gly Gly Phe Asn Ala
                    435                 440                 445
        His Ala Ser Asn Ile Val Ser Ala Val Tyr Leu Ala Thr Gly Gln Asp
            450                 455                 460
        Pro Ala Gln Asn Ile Glu Ser Ser His Cys Ile Thr Met Met Glu Ala
        465                 470                 475                 480
        Val Asn Asp Gly Lys Asp Leu His Ile Ser Val Thr Met Pro Ser Ile
                        485                 490                 495
```

```
Glu Val Gly Thr Val Gly Gly Thr Gln Leu Ala Ser Gln Ser Ala
            500             505                 510

Cys Leu Asn Leu Leu Gly Val Lys Gly Ala Asn Arg Glu Ala Pro Gly
            515                 520                 525

Ser Asn Ala Arg Leu Leu Ala Thr Ile Val Ala Gly Ser Val Leu Ala
530                 535                 540

Gly Glu Leu Ser Leu Met Ser Ala Ile Ser Ala Gly Gln Leu Val Lys
545                 550                 555                 560

Ser His Met Lys Tyr Asn Arg Ser Cys Lys Asp Val Thr Lys
                565                 570

<210> SEQ ID NO 88
<211> LENGTH: 602
<212> TYPE: PRT
<213> ORGANISM: Solanum lycopersicum

<400> SEQUENCE: 88

Met Asp Val Arg Arg Ser Glu Glu Pro Val Tyr Pro Ser Lys Val
1               5                   10                  15

Phe Ala Ala Asp Glu Lys Pro Leu Lys Pro His Lys Lys Gln Gln Gln
                20                  25                  30

Gln Gln Glu Asp Lys Asn Thr Leu Leu Ile Asp Ala Ser Asp Ala Leu
            35                  40                  45

Pro Leu Pro Leu Tyr Leu Thr Thr Asn Gly Leu Phe Phe Thr Met Phe
50                  55                  60

Phe Ser Val Met Tyr Phe Leu Leu Ser Arg Trp Arg Glu Lys Ile Arg
65                  70                  75                  80

Asn Ser Thr Pro Leu His Val Val Thr Leu Ser Glu Leu Gly Ala Ile
                85                  90                  95

Val Ser Leu Ile Ala Ser Val Ile Tyr Leu Leu Gly Phe Phe Gly Ile
            100                 105                 110

Gly Phe Val Gln Thr Phe Val Ser Arg Gly Asn Asn Asp Ser Trp Asp
            115                 120                 125

Glu Asn Asp Glu Glu Phe Leu Leu Lys Glu Asp Ser Arg Cys Gly Pro
130                 135                 140

Ala Thr Thr Leu Gly Cys Ala Val Pro Ala Pro Ala Arg Gln Ile
145                 150                 155                 160

Ala Pro Met Ala Pro Pro Gln Pro Ser Met Ser Val Glu Lys Pro
                165                 170                 175

Ala Pro Leu Ile Thr Ser Ala Ser Ser Gly Glu Asp Glu Ile Ile
            180                 185                 190

Lys Ser Val Val Gln Gly Lys Ile Pro Ser Tyr Ser Leu Glu Ser Lys
                195                 200                 205

Leu Gly Asp Cys Lys Arg Ala Ala Ser Ile Arg Lys Glu Val Met Gln
    210                 215                 220

Arg Ile Thr Gly Lys Ser Leu Glu Gly Leu Pro Leu Glu Gly Phe Asn
225                 230                 235                 240

Tyr Glu Ser Ile Leu Gly Gln Cys Cys Glu Met Pro Ile Gly Tyr Val
                245                 250                 255

Gln Ile Pro Val Gly Ile Ala Gly Pro Leu Leu Leu Asn Gly Lys Glu
            260                 265                 270

Phe Ser Val Pro Met Ala Thr Thr Glu Gly Cys Leu Val Ala Ser Thr
        275                 280                 285

Asn Arg Gly Cys Lys Ala Ile Tyr Ala Ser Gly Gly Ala Thr Cys Ile
```

```
                290                 295                 300
Leu Leu Arg Asp Gly Met Thr Arg Ala Pro Cys Val Arg Phe Gly Thr
305                 310                 315                 320

Ala Lys Arg Ala Ala Glu Leu Lys Phe Phe Val Glu Asp Pro Ile Lys
                325                 330                 335

Phe Glu Ser Leu Ala Asn Val Phe Asn Gln Ser Ser Arg Phe Ala Arg
                340                 345                 350

Leu Gln Arg Ile Gln Cys Ala Ile Ala Gly Lys Asn Leu Tyr Met Arg
                355                 360                 365

Leu Cys Cys Ser Thr Gly Asp Ala Met Gly Met Asn Met Val Ser Lys
                370                 375                 380

Gly Val Gln Asn Val Leu Asp Tyr Leu Gln Asn Glu Tyr Pro Asp Met
385                 390                 395                 400

Asp Val Ile Gly Ile Ser Gly Asn Phe Cys Ser Asp Lys Lys Pro Ala
                405                 410                 415

Ala Val Asn Trp Ile Glu Gly Arg Gly Lys Ser Val Val Cys Glu Ala
                420                 425                 430

Ile Ile Thr Glu Glu Val Val Lys Val Leu Lys Thr Glu Val Ala
                435                 440                 445

Ala Leu Val Glu Leu Asn Met Leu Lys Asn Leu Thr Gly Ser Ala Met
                450                 455                 460

Ala Gly Ala Leu Gly Gly Phe Asn Ala His Ala Ser Asn Ile Val Ser
465                 470                 475                 480

Ala Val Phe Ile Ala Thr Gly Gln Asp Pro Ala Gln Asn Ile Glu Ser
                485                 490                 495

Ser His Cys Ile Thr Met Met Glu Ala Val Asn Asp Gly Lys Asp Leu
                500                 505                 510

His Ile Ser Val Thr Met Pro Ser Ile Glu Val Gly Thr Val Gly Gly
                515                 520                 525

Gly Thr Gln Leu Ala Ser Gln Ser Ala Cys Leu Asn Leu Leu Gly Val
                530                 535                 540

Lys Gly Ala Asn Arg Glu Ala Pro Gly Ser Asn Ala Arg Leu Leu Ala
545                 550                 555                 560

Thr Val Val Ala Gly Ser Val Leu Ala Gly Glu Leu Ser Leu Met Ser
                565                 570                 575

Ala Ile Ser Ser Gly Gln Leu Val Asn Ser His Met Lys Tyr Asn Arg
                580                 585                 590

Ser Thr Lys Asp Val Thr Lys Ala Ser Ser
                595                 600

<210> SEQ ID NO 89
<211> LENGTH: 545
<212> TYPE: PRT
<213> ORGANISM: Medicago polymorpha

<400> SEQUENCE: 89

Met Glu Val Gln Arg Gln Ile Tyr Ser Asp Pro Ser Ser Lys Thr Lys
1               5                   10                  15

Lys Asn Gln Lys Gln Asn Ser Leu Ser Gln Thr Ser Ser Leu Tyr
                20                  25                  30

Leu Thr Asn Thr Phe Phe Gly Leu Phe Phe Ser Val Ala Tyr Phe
                35                  40                  45

Leu Leu Asn Arg Trp Arg Glu Lys Ile Arg Thr Ser Thr Pro Leu His
50                  55                  60
```

```
Val Leu Thr Ile Ser Glu Ile Leu Ala Leu Val Ser Leu Ile Ala Cys
 65                  70                  75                  80

Leu Ile Tyr Leu Thr Ala Phe Phe Gly Val Ala Phe Ile Leu His Tyr
                 85                  90                  95

Asp Glu Glu Asp Glu Val Ala Asp Ile Ala Ala Lys Thr Thr Lys
            100                 105                 110

Val Met Pro Asn Leu Pro Glu Ile Leu Val Gln Lys Val Leu Ser
        115                 120                 125

Met Glu Asp Glu Glu Val Val Gly Ala Val Val Ser Gly Ser Ile Pro
    130                 135                 140

Ser Tyr Ser Leu Glu Ser Lys Leu Gly Asp Cys Arg Arg Ala Ala Val
145                 150                 155                 160

Ile Arg Asn Gln Ala Val Glu Arg Val Thr Gly Arg Ser Leu Glu Gly
                165                 170                 175

Leu Pro Met Glu Gly Phe Asp Tyr Asp Ser Ile Leu Gly Gln Cys Cys
            180                 185                 190

Glu Met Pro Ile Gly Phe Val Gln Ile Pro Val Gly Val Ala Gly Pro
        195                 200                 205

Leu Leu Leu Asp Gly Lys Glu Tyr Thr Val Pro Met Ala Thr Thr Glu
210                 215                 220

Gly Cys Leu Val Ala Ser Thr Asn Arg Gly Cys Lys Ala Ile Tyr Val
225                 230                 235                 240

Ser Gly Gly Ala Ser Ala Val Val Leu Arg Asp Gly Met Thr Arg Ala
                245                 250                 255

Pro Val Val Arg Phe Asn Ser Ala Lys Arg Ala Ser Gln Leu Lys Phe
            260                 265                 270

Phe Leu Glu Asp Pro Leu Asn Phe Asp Ser Ile Ser His Thr Phe Asn
        275                 280                 285

Lys Ser Ser Arg Phe Ala Arg Leu Gln Asn Ile Lys Ala Thr Ile Ala
    290                 295                 300

Gly Lys Asn Leu Tyr Thr Arg Phe Thr Cys Ser Thr Gly Asp Ala Met
305                 310                 315                 320

Gly Met Asn Met Val Ser Lys Gly Val Gln Asn Val Leu Asp Phe Leu
                325                 330                 335

Gln Thr Asp Phe Pro Asp Met Asp Val Ile Gly Ile Ser Gly Asn Phe
            340                 345                 350

Cys Ser Asp Lys Lys Ala Ala Ala Val Asn Trp Ile Glu Gly Arg Gly
        355                 360                 365

Lys Ser Val Val Cys Glu Ala Val Ile Lys Glu Glu Val Val Lys Lys
    370                 375                 380

Val Leu Lys Thr Ser Val Glu Ser Leu Val Glu Leu Asn Met Leu Lys
385                 390                 395                 400

Asn Leu Thr Gly Ser Ala Met Ala Gly Ala Leu Gly Gly Phe Asn Ala
                405                 410                 415

His Ala Ser Asn Ile Val Ser Ala Val Tyr Leu Ala Thr Gly Gln Asp
            420                 425                 430

Pro Ala Gln Asn Val Glu Ser Ser His Cys Met Thr Met Met Glu Ala
        435                 440                 445

Val Asn Asp Gly Lys Asp Leu His Ile Ser Val Thr Met Pro Ser Ile
    450                 455                 460

Glu Val Gly Thr Val Gly Gly Gly Thr Gln Leu Ala Ser Gln Ser Ala
465                 470                 475                 480

Cys Leu Asn Leu Leu Gly Val Lys Gly Ala Ser Lys Glu Ser Pro Gly
```

```
                            485                 490                 495
Ala Asn Ser Arg Gln Leu Ala Thr Ile Val Ala Gly Ser Val Leu Ala
                500                 505                 510

Gly Glu Leu Ser Leu Met Ser Ala Ile Ala Gly Gln Leu Val Lys
            515                 520                 525

Ser His Met Lys Tyr Asn Arg Ser Asn Lys Asp Val Thr Lys Val Ala
530                 535                 540

Ser
545

<210> SEQ ID NO 90
<211> LENGTH: 582
<212> TYPE: PRT
<213> ORGANISM: Medicago polymorpha

<400> SEQUENCE: 90

Met Asp Ala Arg Arg Leu Lys Ser Leu Pro Pro Arg Ser Pro Ala
1               5                   10                  15

Gly Gly Glu Asn Leu Lys Thr Gln Lys Leu Lys Ser Leu Pro Thr Thr
            20                  25                  30

Thr Thr Gly Glu Asn Leu Asn Ser Gln Thr Val Phe Leu Cys Val Thr
        35                  40                  45

Asn Ala Val Phe Phe Gly Val Phe Ser Val Ala Tyr Phe Leu Leu
50                  55                  60

His Arg Trp Arg Glu Lys Ile Arg Thr Glu Thr Pro Leu His Val Val
65                  70                  75                  80

Thr Val Ser Glu Thr Ala Ala Ile Val Ser Leu Ile Ala Ser Ala Val
                85                  90                  95

Tyr Leu Leu Gly Phe Phe Gly Ile Gly Ser Arg Thr Ser Phe Pro Asp
            100                 105                 110

Asp Leu Ser Asp Glu Glu Ile Leu Ala Lys Glu Asp Ser Arg Lys Pro
        115                 120                 125

Gly Pro Cys Pro Ala Ala Leu Val Asp Thr Asp Val Lys Pro Pro Pro
    130                 135                 140

Ala Thr Leu Thr Pro Ile Val Ala Pro Val Lys Ile Tyr Glu Val Val
145                 150                 155                 160

Ala Pro Val Asn Leu Thr Pro Glu Asp Glu Glu Ile Ala Lys Ser Val
                165                 170                 175

Val Thr Gly Ser Ile Pro Ser Tyr Ser Leu Glu Ser Arg Leu Ala Asp
            180                 185                 190

Cys Arg Lys Ala Ala Ala Ile Arg Arg Ser Ala Val Gln Thr Ile Thr
        195                 200                 205

Gly Lys Ser Leu Glu Gly Leu Pro Leu Glu Gly Phe Asp Tyr Asp Ser
    210                 215                 220

Ile Leu Gly Gln Cys Cys Glu Met Pro Ile Gly Phe Val Gln Ile Pro
225                 230                 235                 240

Val Gly Val Ala Gly Pro Leu Leu Leu Asp Gly Val Glu Tyr Thr Val
                245                 250                 255

Pro Met Ala Thr Thr Glu Gly Cys Leu Val Ala Ser Thr Asn Arg Gly
            260                 265                 270

Cys Lys Ala Ile His Val Ser Gly Gly Ala Ser Ser Val Leu Leu Arg
        275                 280                 285

Asp Gly Met Thr Arg Ala Pro Val Val Arg Phe Ser Ala Lys Arg
    290                 295                 300
```

```
Ala Ala Glu Leu Lys Phe Phe Leu Glu Asp Pro Leu Asn Phe Asp Thr
305                 310                 315                 320

Leu Ala Val Thr Phe Asn Lys Ser Ser Arg Phe Ala Arg Leu Gln Ser
            325                 330                 335

Leu Gln Pro Thr Ile Ala Gly Lys Asn Leu Tyr Ile Arg Phe Arg Cys
            340                 345                 350

Ser Thr Gly Asp Ala Met Gly Met Asn Met Val Ser Lys Gly Val Gln
            355                 360                 365

Asn Val Leu Asp Phe Leu Gln Ser Asp Phe Pro Asp Met Asp Val Ile
        370                 375                 380

Gly Ile Ser Gly Asn Phe Cys Ser Asp Lys Lys Ala Ala Ala Val Asn
385                 390                 395                 400

Trp Ile Glu Gly Arg Gly Lys Ser Val Val Cys Glu Ala Val Ile Lys
            405                 410                 415

Glu Glu Val Val Lys Lys Val Leu Lys Thr Ser Val Glu Ala Leu Val
            420                 425                 430

Glu Leu Asn Met Leu Lys Asn Leu Thr Gly Ser Ala Leu Ala Gly Ala
            435                 440                 445

Leu Gly Gly Phe Asn Ala His Ala Ser Asn Ile Val Ser Ala Val Tyr
450                 455                 460

Ile Ala Thr Gly Gln Asp Pro Ala Gln Asn Val Glu Ser Ser His Cys
465                 470                 475                 480

Ile Thr Met Met Glu Ala Val Asn Asp Gly Lys Asp Leu His Ile Ser
            485                 490                 495

Val Thr Met Pro Ser Ile Glu Val Gly Thr Val Gly Gly Gly Thr Gln
            500                 505                 510

Leu Ala Ser Gln Ser Ala Cys Leu Asn Leu Leu Gly Val Lys Gly Ala
            515                 520                 525

Asn Thr Glu Ser Pro Gly Ala Asn Ala Arg Leu Leu Ala Thr Ile Val
        530                 535                 540

Ala Gly Ser Val Leu Ala Gly Glu Leu Ser Leu Met Ser Ala Ile Ala
545                 550                 555                 560

Ala Gly Gln Leu Val Lys Ser His Met Lys Tyr Asn Arg Ser Ser Arg
            565                 570                 575

Asp Met Ser Lys Ile Val
            580

<210> SEQ ID NO 91
<211> LENGTH: 18
<212> TYPE: PRT
<213> ORGANISM: Arabidopsis thaliana

<400> SEQUENCE: 91

Ser Gly Gly Ala Thr Ser Thr Val Leu Lys Asp Gly Met Thr Arg Ala Pro Val
1               5                   10                  15

<210> SEQ ID NO 92
<211> LENGTH: 9
<212> TYPE: PRT
<213> ORGANISM: Arabidopsis thaliana

<400> SEQUENCE: 92

Ser His Met Lys Tyr Asn Arg Ser Ser
1               5

<210> SEQ ID NO 93
<211> LENGTH: 45
```

```
<212> TYPE: DNA
<213> ORGANISM: Artificial Sequence
<220> FEATURE:
<223> OTHER INFORMATION: PRIMER-57

<400> SEQUENCE: 93
cttgtcaggt ggggccaccg ccgtcttgtt gaaggatggc atgac          45

<210> SEQ ID NO 94
<211> LENGTH: 45
<212> TYPE: DNA
<213> ORGANISM: Artificial Sequence
<220> FEATURE:
<223> OTHER INFORMATION: PRIMER-58

<400> SEQUENCE: 94
gtcatgccat ccttcaacaa gacggcggtg gccccacctg acaag          45

<210> SEQ ID NO 95
<211> LENGTH: 44
<212> TYPE: DNA
<213> ORGANISM: Artificial Sequence
<220> FEATURE:
<223> OTHER INFORMATION: PRIMER-59

<400> SEQUENCE: 95
gctatgttta tctctggtgg cgccaccgat accgttctta agga           44

<210> SEQ ID NO 96
<211> LENGTH: 44
<212> TYPE: DNA
<213> ORGANISM: Artificial Sequence
<220> FEATURE:
<223> OTHER INFORMATION: PRIMER-60

<400> SEQUENCE: 96
tccttaagaa cggtatcggt ggcgccacca gagataaaca tagc           44

<210> SEQ ID NO 97
<211> LENGTH: 45
<212> TYPE: DNA
<213> ORGANISM: Artificial Sequence
<220> FEATURE:
<223> OTHER INFORMATION: PRIMER-61

<400> SEQUENCE: 97
cttgtcaggt ggggccaccg aagtcttgtt gaaggatggc atgac          45

<210> SEQ ID NO 98
<211> LENGTH: 45
<212> TYPE: DNA
<213> ORGANISM: Artificial Sequence
<220> FEATURE:
<223> OTHER INFORMATION: PRIMER-62

<400> SEQUENCE: 98
gtcatgccat ccttcaacaa gacttcggtg gccccacctg acaag          45

<210> SEQ ID NO 99
<211> LENGTH: 45
<212> TYPE: DNA
<213> ORGANISM: Artificial Sequence
<220> FEATURE:
<223> OTHER INFORMATION: PRIMER-63

<400> SEQUENCE: 99
```
gtcaagagtc acatgaagtt caacagatcc agcaaagata tgtct          45

<210> SEQ ID NO 100
<211> LENGTH: 45
<212> TYPE: DNA
<213> ORGANISM: Artificial Sequence
<220> FEATURE:
<223> OTHER INFORMATION: PRIMER-64

<400> SEQUENCE: 100
agacatatct ttgctggatc tgttgaactt catgtgactc ttgac          45

<210> SEQ ID NO 101
<211> LENGTH: 45
<212> TYPE: DNA
<213> ORGANISM: Artificial Sequence
<220> FEATURE:
<223> OTHER INFORMATION: PRIMER-65

<400> SEQUENCE: 101
gtcaagagtc acatgaagga caacagatcc agcaaagata tgtct          45

<210> SEQ ID NO 102
<211> LENGTH: 45
<212> TYPE: DNA
<213> ORGANISM: Artificial Sequence
<220> FEATURE:
<223> OTHER INFORMATION: PRIMER-66

<400> SEQUENCE: 102
agacatatct ttgctggatc tgttgtcctt catgtgactc ttgac          45

<210> SEQ ID NO 103
<211> LENGTH: 45
<212> TYPE: DNA
<213> ORGANISM: Artificial Sequence
<220> FEATURE:
<223> OTHER INFORMATION: PRIMER-67

<400> SEQUENCE: 103
gtcaagagtc acatgaagga aaacagatcc agcaaagata tgtct          45

<210> SEQ ID NO 104
<211> LENGTH: 45
<212> TYPE: DNA
<213> ORGANISM: Artificial Sequence
<220> FEATURE:
<223> OTHER INFORMATION: PRIMER-68

<400> SEQUENCE: 104
agacatatct ttgctggatc tgttttcctt catgtgactc ttgac          45

<210> SEQ ID NO 105
<211> LENGTH: 1728
<212> TYPE: DNA
<213> ORGANISM: Hevea brasiliensis

<400> SEQUENCE: 105
atggacacca ccggccggct ccaccaccga aagcatgcta cacccgttga ggaccgttct     60
ccgaccactc cgaaagcgtc ggacgcgctt ccgcttcccc tctacctgac caacgcggtt    120
ttcttcacgc tgttcttctc ggtggcgtat tacctccttc accggtggcg cgacaagatc    180
cgcaactcca ctcccttca tatcgttact ctctctgaaa ttgttgctat tgtctccctc    240
attgcctctt tcatttacct cctaggattc ttcggtatcg attttgtgca gtcattcatt    300

```
gcacgcgcct cccatgacgt gtgggacctc gaagatacgg atcccaacta cctcatcgat    360
gaagatcacc gtctcgttac ttgccctccc gctaatatat ctactaagac taccattatt    420
gccgcaccta ccaaattgcc tacctcggaa cccttaattg cacccttagt ctcggaggaa    480
gacgaaatga tcgtcaactc cgtcgtggat gggaagatac cctcctattc tctggagtcg    540
aagctcgggg actgcaaacg agcggctgcg attcgacgcg aggctttgca gaggatgaca    600
aggaggtcgc tggaaggctt gccagtagaa gggttcgatt acgagtcgat tttaggacaa    660
tgctgtgaaa tgccagtggg atacgtgcag attccggtgg ggattgcggg gccgttgttg    720
ctgaacgggc gggagtactc tgttccaatg gcgaccacgg agggttgttt ggtggcgagc    780
actaatagag ggtgtaaggc gatttacttg tcaggtgggg ccaccagcgt cttgttgaag    840
gatggcatga caagagcgcc tgttgtaaga ttcgcgtcgg cgactagagc cgcggagttg    900
aagttcttct tggaggatcc tgacaatttt gataccttgg ccgtagtttt taacaagtcc    960
agtagatttg cgaggctcca aggcattaaa tgctcaattg ctggtaagaa tctttatata   1020
agattcagct gcagcactgg cgatgcaatg gggatgaaca tggtttctaa aggggttcaa   1080
aacgttcttg aatttcttca aagtgatttt tctgatatgg atgtcattgg aatctcagga   1140 aattttttgtt cggataagaa gcctgctgct gtaaattgga ttgaaggacg tggcaaatca   1200
gttgtttgtg aggcaattat caaggaagag gtggtgaaga aggtgttgaa aaccaatgtg   1260
gcctccctag tggagcttaa catgctcaag aatcttgctg ttctgctgt tgctggtgct   1320 ttgggtggat ttaatgccca tgcaggcaac atcgtatctg caatctttat tgccactggc   1380
caggatccag cacagaatgt tgagagttct cattgcatta ccatgatgga agctgtcaat   1440
gatgaaaagg atctccatat ctctgtgacc atgccctcca ttgaggtggg tacagtcgga   1500
ggtggaactc aacttgcatc tcagtctgct tgtctcaatt gcttggggt gaagggtgca   1560 aacaaagagt cgccaggatc aaactcaagg ctccttgctg ccatcgtagc tggttcagtt   1620
ttggctggtg agctctcctt gatgtctgcc attgcagctg ggcagcttgt caagagtcac   1680
atgaagtaca acagatccag caaagatatg tctaaagctg catcttag              1728
```

<210> SEQ ID NO 106
<211> LENGTH: 31
<212> TYPE: DNA
<213> ORGANISM: Artificial Sequence
<220> FEATURE:
<223> OTHER INFORMATION: PRIMER-69

<400> SEQUENCE: 106

```
caccatggac accaccggcc ggctccacca c                                    31
```

<210> SEQ ID NO 107
<211> LENGTH: 30
<212> TYPE: DNA
<213> ORGANISM: Artificial Sequence
<220> FEATURE:
<223> OTHER INFORMATION: PRIMER-70

<400> SEQUENCE: 107

```
cgcctcgagt caagatgcag ctttagacat                                      30
```

<210> SEQ ID NO 108
<211> LENGTH: 34
<212> TYPE: DNA
<213> ORGANISM: Artificial Sequence
<220> FEATURE:

<223> OTHER INFORMATION: PRIMER-71

<400> SEQUENCE: 108
gtagaagggt tcgatttcga gtcgatttta ggac                                    34

<210> SEQ ID NO 109
<211> LENGTH: 34
<212> TYPE: DNA
<213> ORGANISM: Artificial Sequence
<220> FEATURE:
<223> OTHER INFORMATION: PRIMER-72

<400> SEQUENCE: 109
gtcctaaaat cgactcgaaa tcgaacccett ctac                                    34

<210> SEQ ID NO 110
<211> LENGTH: 35
<212> TYPE: DNA
<213> ORGANISM: Artificial Sequence
<220> FEATURE:
<223> OTHER INFORMATION: PRIMER-73

<400> SEQUENCE: 110
gtagaagggt tcgatgaaga gtcgatttta ggaca                                   35

<210> SEQ ID NO 111
<211> LENGTH: 35
<212> TYPE: DNA
<213> ORGANISM: Artificial Sequence
<220> FEATURE:
<223> OTHER INFORMATION: PRIMER-74

<400> SEQUENCE: 111
tgtcctaaaa tcgactcttc atcgaaccct tctac                                   35

<210> SEQ ID NO 112
<211> LENGTH: 33
<212> TYPE: DNA
<213> ORGANISM: Artificial Sequence
<220> FEATURE:
<223> OTHER INFORMATION: PRIMER-75

<400> SEQUENCE: 112
gctgaacggg cgggagttct ctgttccaat ggc                                     33

<210> SEQ ID NO 113
<211> LENGTH: 33
<212> TYPE: DNA
<213> ORGANISM: Artificial Sequence
<220> FEATURE:
<223> OTHER INFORMATION: PRIMER-76

<400> SEQUENCE: 113
gccattggaa cagagaactc ccgcccgttc agc                                     33

<210> SEQ ID NO 114
<211> LENGTH: 33
<212> TYPE: DNA
<213> ORGANISM: Artificial Sequence
<220> FEATURE:
<223> OTHER INFORMATION: PRIMER-77

<400> SEQUENCE: 114
gctgaacggg cgggaggaat ctgttccaat ggc                                     33

```
<210> SEQ ID NO 115
<211> LENGTH: 33
<212> TYPE: DNA
<213> ORGANISM: Artificial Sequence
<220> FEATURE:
<223> OTHER INFORMATION: PRIMER-78

<400> SEQUENCE: 115
gccattggaa cagattcctc ccgcccgttc agc                              33

<210> SEQ ID NO 116
<211> LENGTH: 30
<212> TYPE: DNA
<213> ORGANISM: Artificial Sequence
<220> FEATURE:
<223> OTHER INFORMATION: PRIMER-79

<400> SEQUENCE: 116
gaaggacgtg gcaaagccgt tgtttgtgag                                  30

<210> SEQ ID NO 117
<211> LENGTH: 30
<212> TYPE: DNA
<213> ORGANISM: Artificial Sequence
<220> FEATURE:
<223> OTHER INFORMATION: PRIMER-80

<400> SEQUENCE: 117
ctcacaaaca acggctttgc cacgtccttc                                  30

<210> SEQ ID NO 118
<211> LENGTH: 43
<212> TYPE: DNA
<213> ORGANISM: Artificial Sequence
<220> FEATURE:
<223> OTHER INFORMATION: PRIMER-81

<400> SEQUENCE: 118
tgaaggacgt ggcaaagacg ttgtttgtga ggcaattatc aag                   43

<210> SEQ ID NO 119
<211> LENGTH: 43
<212> TYPE: DNA
<213> ORGANISM: Artificial Sequence
<220> FEATURE:
<223> OTHER INFORMATION: PRIMER-82

<400> SEQUENCE: 119
cttgataatt gcctcacaaa caacgtcttt gccacgtcct tca                   43

<210> SEQ ID NO 120
<211> LENGTH: 43
<212> TYPE: DNA
<213> ORGANISM: Artificial Sequence
<220> FEATURE:
<223> OTHER INFORMATION: PRIMER-83

<400> SEQUENCE: 120
tgaaggacgt ggcaaagaag ttgtttgtga ggcaattatc aag                   43

<210> SEQ ID NO 121
<211> LENGTH: 43
<212> TYPE: DNA
<213> ORGANISM: Artificial Sequence
<220> FEATURE:
<223> OTHER INFORMATION: PRIMER-84
```

```
<400> SEQUENCE: 121
cttgataatt gcctcacaaa caacttcttt gccacgtcct tca                 43

<210> SEQ ID NO 122
<211> LENGTH: 34
<212> TYPE: DNA
<213> ORGANISM: Artificial Sequence
<220> FEATURE:
<223> OTHER INFORMATION: PRIMER-85

<400> SEQUENCE: 122
ctgcaatctt tattgcctgt ggccaggatc cagc                           34

<210> SEQ ID NO 123
<211> LENGTH: 34
<212> TYPE: DNA
<213> ORGANISM: Artificial Sequence
<220> FEATURE:
<223> OTHER INFORMATION: PRIMER-86

<400> SEQUENCE: 123
gctggatcct ggccacaggc aataaagatt gcag                           34

<210> SEQ ID NO 124
<211> LENGTH: 45
<212> TYPE: DNA
<213> ORGANISM: Artificial Sequence
<220> FEATURE:
<223> OTHER INFORMATION: PRIMER-87

<400> SEQUENCE: 124
tcgtatctgc aatctttatt gccgatggcc aggatccagc acaga               45

<210> SEQ ID NO 125
<211> LENGTH: 45
<212> TYPE: DNA
<213> ORGANISM: Artificial Sequence
<220> FEATURE:
<223> OTHER INFORMATION: PRIMER-88

<400> SEQUENCE: 125
tctgtgctgg atcctggcca tcggcaataa agattgcaga tacga               45

<210> SEQ ID NO 126
<211> LENGTH: 45
<212> TYPE: DNA
<213> ORGANISM: Artificial Sequence
<220> FEATURE:
<223> OTHER INFORMATION: PRIMER-89

<400> SEQUENCE: 126
tcgtatctgc aatctttatt gccgaaggcc aggatccagc acaga               45

<210> SEQ ID NO 127
<211> LENGTH: 45
<212> TYPE: DNA
<213> ORGANISM: Artificial Sequence
<220> FEATURE:
<223> OTHER INFORMATION: PRIMER-90

<400> SEQUENCE: 127
tctgtgctgg atcctggcct tcggcaataa agattgcaga tacga               45

<210> SEQ ID NO 128
<211> LENGTH: 35
```

```
<212> TYPE: DNA
<213> ORGANISM: Artificial Sequence
<220> FEATURE:
<223> OTHER INFORMATION: PRIMER-91

<400> SEQUENCE: 128
ctccattgag gtgggttgtg tcggaggtgg aactc                              35

<210> SEQ ID NO 129
<211> LENGTH: 35
<212> TYPE: DNA
<213> ORGANISM: Artificial Sequence
<220> FEATURE:
<223> OTHER INFORMATION: PRIMER-92

<400> SEQUENCE: 129
gagttccacc tccgacacaa cccacctcaa tggag                              35

<210> SEQ ID NO 130
<211> LENGTH: 46
<212> TYPE: DNA
<213> ORGANISM: Artificial Sequence
<220> FEATURE:
<223> OTHER INFORMATION: PRIMER-93

<400> SEQUENCE: 130
accatgccct ccattgaggt gggtgacgtc ggaggtggaa ctcaac                  46

<210> SEQ ID NO 131
<211> LENGTH: 46
<212> TYPE: DNA
<213> ORGANISM: Artificial Sequence
<220> FEATURE:
<223> OTHER INFORMATION: PRIMER-94

<400> SEQUENCE: 131
gttgagttcc acctccgacg tcacccacct caatggaggg catggt                  46

<210> SEQ ID NO 132
<211> LENGTH: 46
<212> TYPE: DNA
<213> ORGANISM: Artificial Sequence
<220> FEATURE:
<223> OTHER INFORMATION: PRIMER-95

<400> SEQUENCE: 132
accatgccct ccattgaggt gggtgaagtc ggaggtggaa ctcaac                  46

<210> SEQ ID NO 133
<211> LENGTH: 46
<212> TYPE: DNA
<213> ORGANISM: Artificial Sequence
<220> FEATURE:
<223> OTHER INFORMATION: PRIMER-96

<400> SEQUENCE: 133
gttgagttcc acctccgact tcacccacct caatggaggg catggt                  46

<210> SEQ ID NO 134
<211> LENGTH: 44
<212> TYPE: DNA
<213> ORGANISM: Artificial Sequence
<220> FEATURE:
<223> OTHER INFORMATION: PRIMER-97

<400> SEQUENCE: 134
```

```
gtcacatgaa gtacaacaga gccagcaaag atatgtctaa agct            44
```

<210> SEQ ID NO 135
<211> LENGTH: 45
<212> TYPE: DNA
<213> ORGANISM: Artificial Sequence
<220> FEATURE:
<223> OTHER INFORMATION: PRIMER-98

<400> SEQUENCE: 135

```
agctttagac atatctttgc tggctctgtt gtacttcatg tgact           45
```

<210> SEQ ID NO 136
<211> LENGTH: 44
<212> TYPE: DNA
<213> ORGANISM: Artificial Sequence
<220> FEATURE:
<223> OTHER INFORMATION: PRIMER-99

<400> SEQUENCE: 136

```
gtcacatgaa gtacaacaga gacagcaaag atatgtctaa agct            44
```

<210> SEQ ID NO 137
<211> LENGTH: 45
<212> TYPE: DNA
<213> ORGANISM: Artificial Sequence
<220> FEATURE:
<223> OTHER INFORMATION: PRIMER-100

<400> SEQUENCE: 137

```
agctttagac atatctttgc tgtctctgtt gtacttcatg tgact           45
```

<210> SEQ ID NO 138
<211> LENGTH: 45
<212> TYPE: DNA
<213> ORGANISM: Artificial Sequence
<220> FEATURE:
<223> OTHER INFORMATION: PRIMER-101

<400> SEQUENCE: 138

```
cttgtcaggt ggggccaccg ccgtcttgtt gaaggatggc atgac           45
```

<210> SEQ ID NO 139
<211> LENGTH: 45
<212> TYPE: DNA
<213> ORGANISM: Artificial Sequence
<220> FEATURE:
<223> OTHER INFORMATION: PRIMER-102

<400> SEQUENCE: 139

```
gtcatgccat ccttcaacaa gacggcggtg gccccacctg acaag           45
```

<210> SEQ ID NO 140
<211> LENGTH: 30
<212> TYPE: DNA
<213> ORGANISM: Artificial Sequence
<220> FEATURE:
<223> OTHER INFORMATION: PRIMER-103

<400> SEQUENCE: 140

```
caggtggggc caccgacgtc ttgttgaagg                            30
```

<210> SEQ ID NO 141
<211> LENGTH: 30
<212> TYPE: DNA
<213> ORGANISM: Artificial Sequence

```
<220> FEATURE:
<223> OTHER INFORMATION: PRIMER-104

<400> SEQUENCE: 141
ccttcaacaa gacgtcggtg gccccacctg                                    30

<210> SEQ ID NO 142
<211> LENGTH: 45
<212> TYPE: DNA
<213> ORGANISM: Artificial Sequence
<220> FEATURE:
<223> OTHER INFORMATION: PRIMER-105

<400> SEQUENCE: 142
cttgtcaggt ggggccaccg aagtcttgtt gaaggatggc atgac                   45

<210> SEQ ID NO 143
<211> LENGTH: 45
<212> TYPE: DNA
<213> ORGANISM: Artificial Sequence
<220> FEATURE:
<223> OTHER INFORMATION: PRIMER-106

<400> SEQUENCE: 143
gtcatgccat ccttcaacaa gacttcggtg gccccacctg acaag                   45

<210> SEQ ID NO 144
<211> LENGTH: 33
<212> TYPE: DNA
<213> ORGANISM: Artificial Sequence
<220> FEATURE:
<223> OTHER INFORMATION: PRIMER-107

<400> SEQUENCE: 144
gtcaagagtc acatgaagtt caacagatcc agc                                33

<210> SEQ ID NO 145
<211> LENGTH: 33
<212> TYPE: DNA
<213> ORGANISM: Artificial Sequence
<220> FEATURE:
<223> OTHER INFORMATION: PRIMER-108

<400> SEQUENCE: 145
gctggatctg ttgaacttca tgtgactctt gac                                33

<210> SEQ ID NO 146
<211> LENGTH: 33
<212> TYPE: DNA
<213> ORGANISM: Artificial Sequence
<220> FEATURE:
<223> OTHER INFORMATION: PRIMER-109

<400> SEQUENCE: 146
gtcaagagtc acatgaagga caacagatcc agc                                33

<210> SEQ ID NO 147
<211> LENGTH: 33
<212> TYPE: DNA
<213> ORGANISM: Artificial Sequence
<220> FEATURE:
<223> OTHER INFORMATION: PRIMER-110

<400> SEQUENCE: 147
gctggatctg ttgtccttca tgtgactctt gac                                33
```

```
<210> SEQ ID NO 148
<211> LENGTH: 33
<212> TYPE: DNA
<213> ORGANISM: Artificial Sequence
<220> FEATURE:
<223> OTHER INFORMATION: PRIMER-111

<400> SEQUENCE: 148
gtcaagagtc acatgaagga aaacagatcc agc                                33

<210> SEQ ID NO 149
<211> LENGTH: 33
<212> TYPE: DNA
<213> ORGANISM: Artificial Sequence
<220> FEATURE:
<223> OTHER INFORMATION: PRIMER-112

<400> SEQUENCE: 149
gctggatctg ttttccttca tgtgactctt gac                                33

<210> SEQ ID NO 150
<211> LENGTH: 45
<212> TYPE: DNA
<213> ORGANISM: Artificial Sequence
<220> FEATURE:
<223> OTHER INFORMATION: PRIMER-113

<400> SEQUENCE: 150
gtcaagagtc acatgaaggc aacagatcc agcaaagata tgtct                    45

<210> SEQ ID NO 151
<211> LENGTH: 45
<212> TYPE: DNA
<213> ORGANISM: Artificial Sequence
<220> FEATURE:
<223> OTHER INFORMATION: PRIMER-114

<400> SEQUENCE: 151
agacatatct ttgctggatc tgttggcctt catgtgactc ttgac                   45
```